United States Patent [19]

Sakiyama et al.

[11] Patent Number: 4,989,582
[45] Date of Patent: Feb. 5, 1991

[54] WINDING TYPE ENDOSCOPE APPARATUS

[75] Inventors: Katsunori Sakiyama, Hachioji; Tomoaki Sato, Higashiyamato; Teruo Eino, Hachioji, all of Japan

[73] Assignee: Olympus Optical Co., Ltd., Tokyo, Japan

[21] Appl. No.: 369,589

[22] Filed: Jun. 21, 1989

Related U.S. Application Data

[63] Continuation-in-part of Ser. No. 146,982, Jan. 20, 1988, abandoned.

[30] Foreign Application Priority Data

| Jan. 20, 1987 | [JP] | Japan | 62-11009 |
| Jul. 6, 1987 | [JP] | Japan | 62-104075 |
| Jul. 31, 1987 | [JP] | Japan | 62-118366 |
| Dec. 17, 1987 | [JP] | Japan | 62-322606 |
| Jul. 5, 1988 | [JP] | Japan | 63-168170 |

[51] Int. Cl.⁵ .......................................... A61B 1/00
[52] U.S. Cl. ........................................... 128/6; 358/98
[58] Field of Search .................. 128/4, 6; 358/98

[56] References Cited

U.S. PATENT DOCUMENTS 4,607,925 8/1986 Kamigaichi et al.

FOREIGN PATENT DOCUMENTS

| 56-75133 | 6/1981 | Japan . |
| 56-164688 | 12/1981 | Japan . |
| 61-75315 | 4/1986 | Japan . |
| 62-9307 | 1/1987 | Japan . |

OTHER PUBLICATIONS

Publication of Furukawa Optical Fiber System, No Publication Date on Document.

Primary Examiner—William H. Grieb
Attorney, Agent, or Firm—Armstrong, Nikaido, Marmelstein, Kubovcik & Murray

[57] ABSTRACT

This endoscope apparatus is provided with an elongate flexible insertable part; a winding unit with a supporting structure having a winding member connected with the insertable part at the base end for winding up and housing the insertable part; an illuminating device for emitting an illuminating light for the endoscope; and an observing device for producing an image of an object to be observed. An external apparatus forming one or both of the illuminating device and observing device is provided separately from the winding member. A flexible connecting means is extended axially out of the side of the winding member and operatively connects the insertable part to the external apparatus.

54 Claims, 57 Drawing Sheets

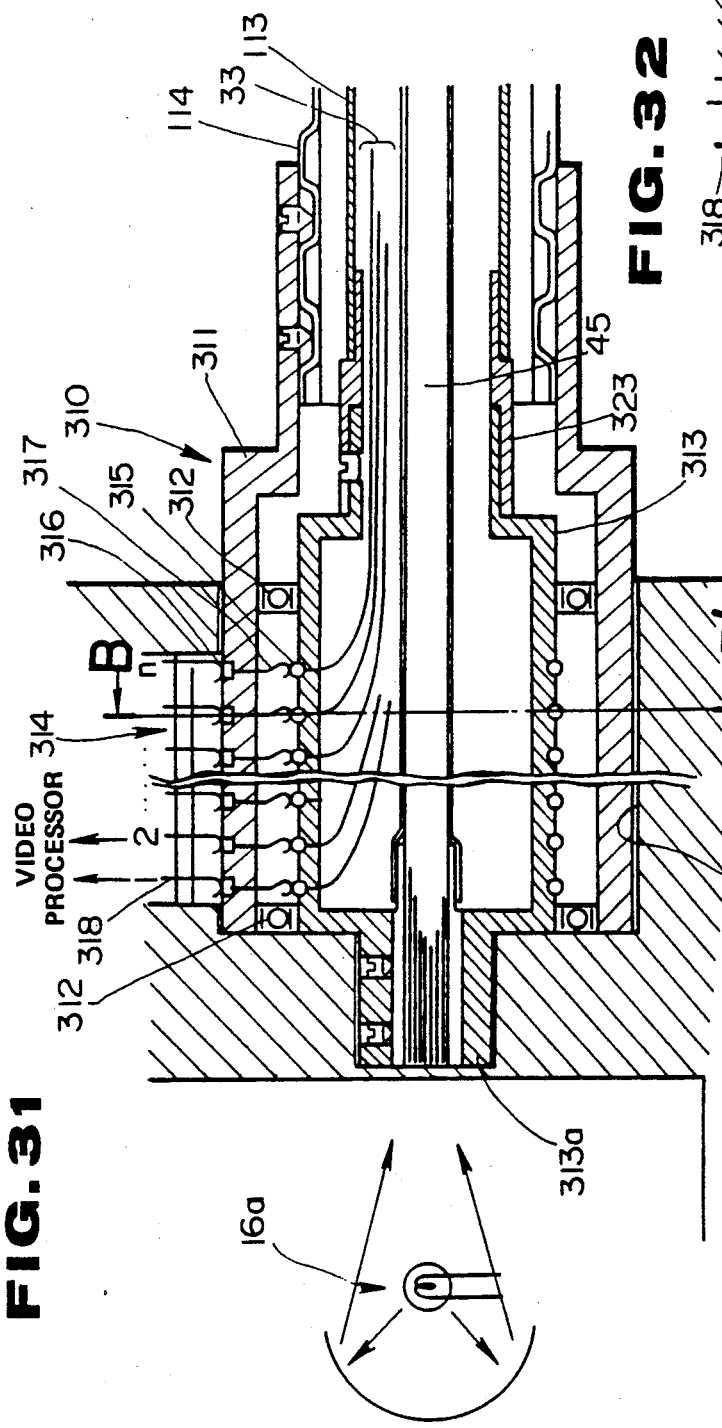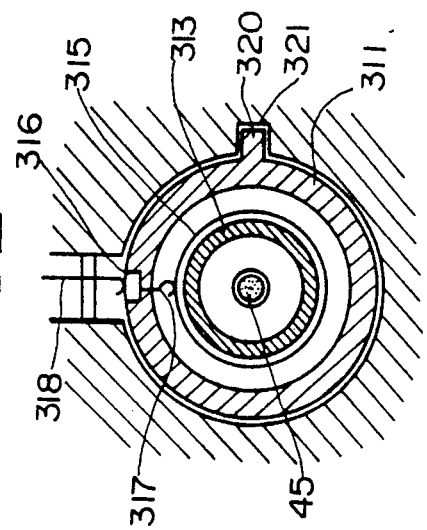

CONTROL CIRCUIT

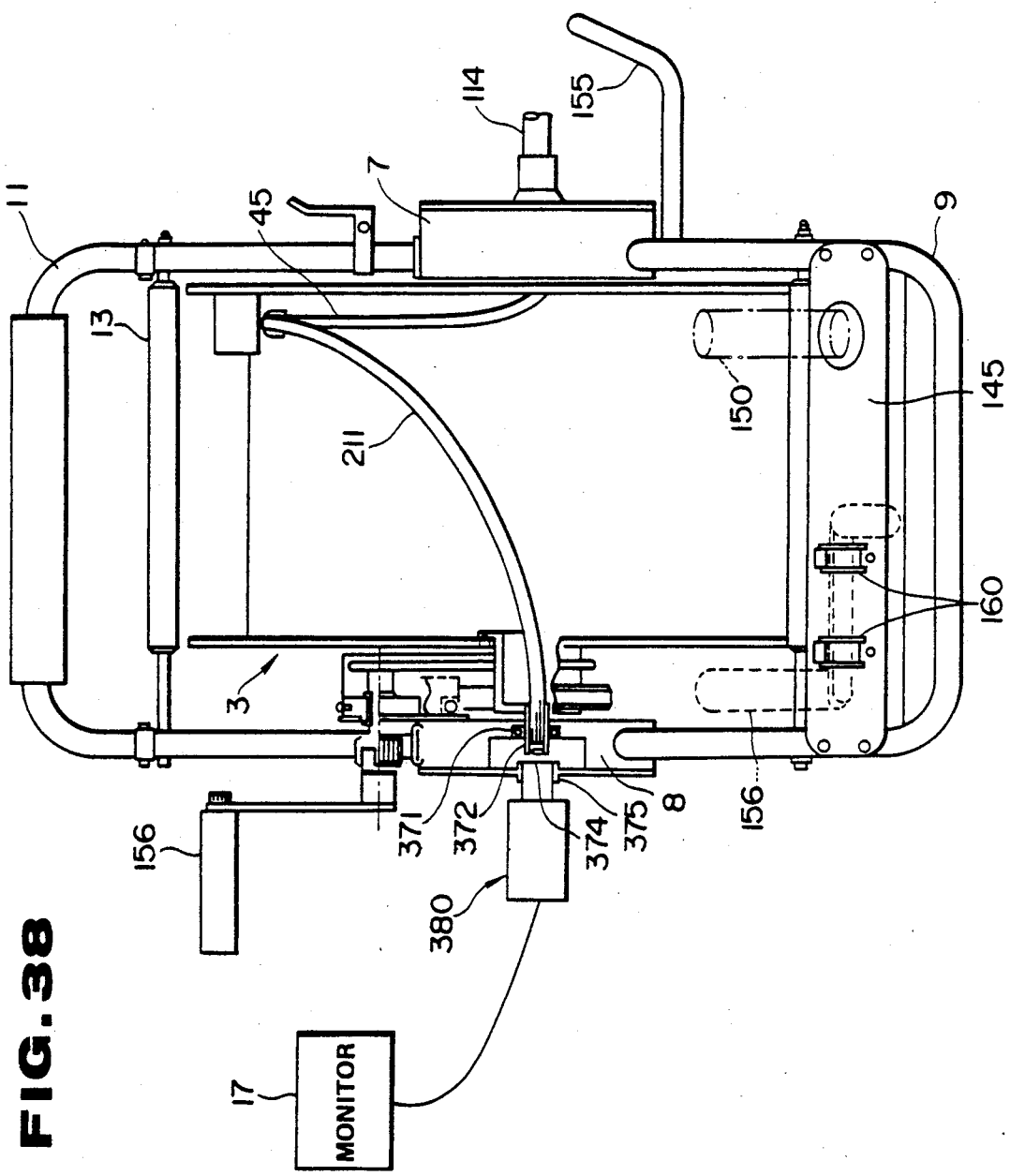

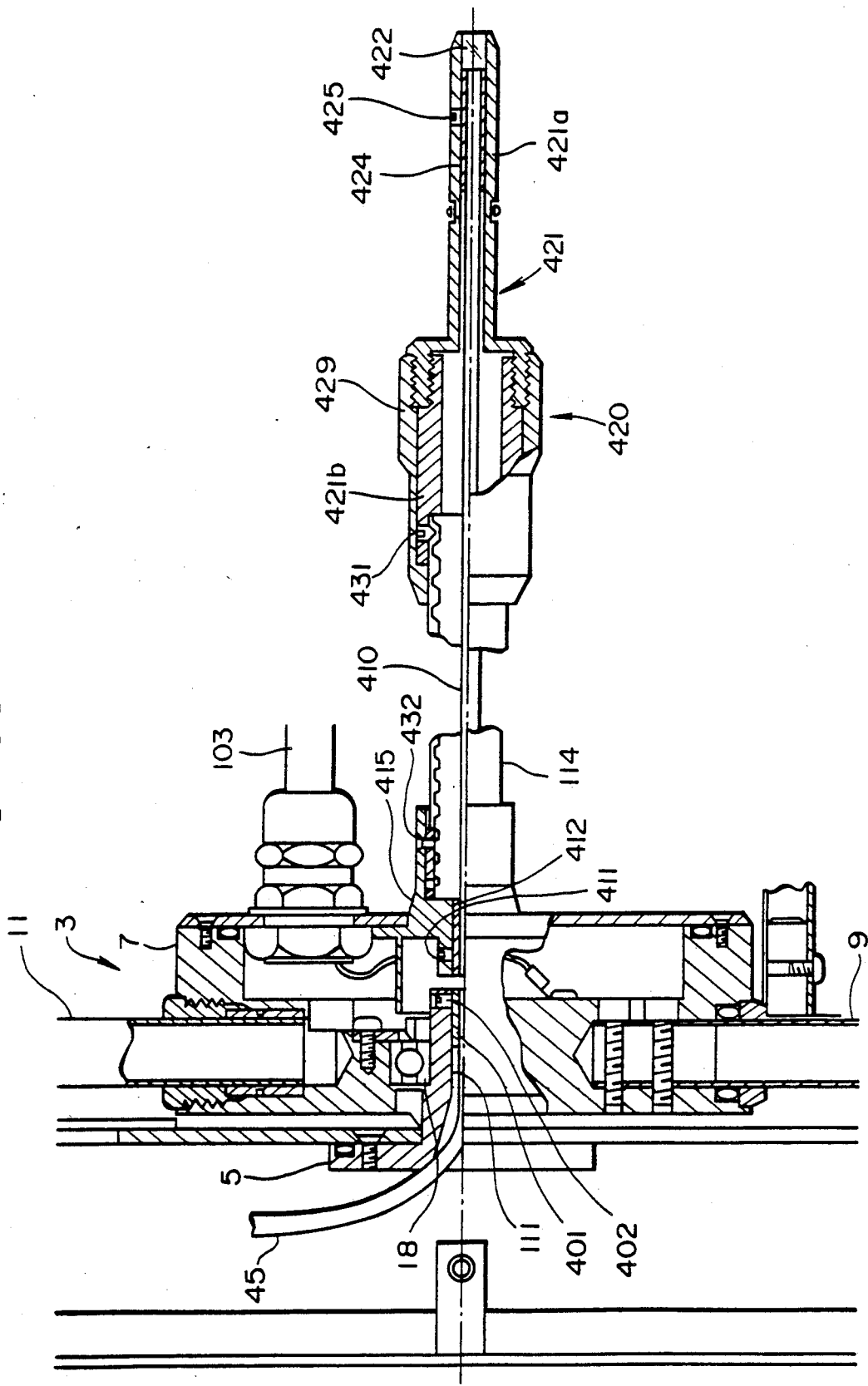

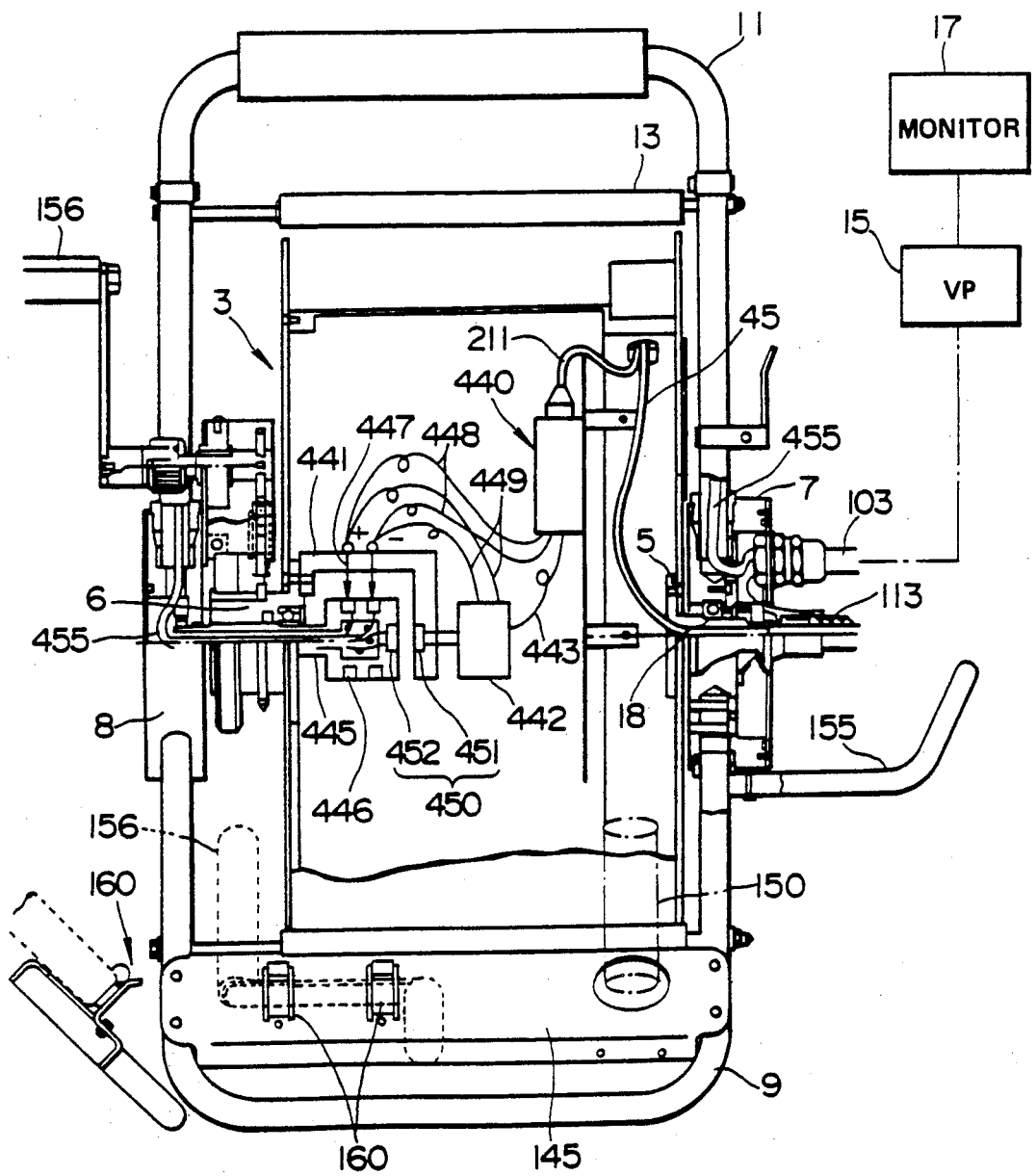

VERTICAL SYNCHRONOUS SIGNAL PART
HORIZONTAL SYNCHRONOUS SIGNAL PART
LUMINANCE & COLOR SIGNAL PART

WINDING TYPE ENDOSCOPE APPARATUS

This is a continuation-in-part application of U.S. Patent Application Ser. No. 146,982 filed on Jan. 20, 1988.

BACKGROUND OF THE INVENTION

1. Field of the Invention

This invention relates to an endoscope apparatus wherein the insertable part can be housed as wound up on a drum.

2. Related Art Statement

Recently, there has been extensively utilized a medical endoscope whereby organs within a body cavity can be observed by inserting an elongate insertable part into the body cavity or various treatments can be made as required by using treating instruments inserted through a treating instrument channel. Also, in the industrial field, there has been extensively utilized an industrial endoscope whereby the interior of a boiler, turbine, engine or chemical plant can be observed or inspected.

There is such industrial endoscope as, for example, a Borehole Scope System (trade name) made by Furukawa Electric Industrial Company, Ltd., Japan wherein an illuminating light is transmitted to the tip of a long insertable part by using a light guide of light conducting fibers to inspect a long pipe or the like, and the above mentioned insertable part can be housed as wound up on a drum. In such apparatus, a light source is fitted on a drum rotating shaft on the drum integrally with a frame of the drum and the optical axis of the light source and the optical axis of the light guide of fibers are made to coincide with each other to make the light of the above mentioned light source enter the light guide.

An illuminating apparatus provided with a fiber bundle windable on a drum is disclosed in the publication of a Japanese utility model application laid open No. 9307/1987. However, in this illuminating apparatus, too, the light source is housed within the drum.

However, there are problems that, if the drum and light source are made integral with each other so as to be inseparable in use, the drum will be so large and heavy as to make it difficult to carry, position and operate it and that, as the light source can not be set in any desired position, the utility of the light source will be low.

Also, in the conventional drum, as the insertable is wound up on the outer periphery of the drum, if an insertable part having little flexibility is wound up on a drum of a small diameter, the bending rigidity will be so high that the wound insertable part will expand to have a large diameter. Generally, a long endoscope is used to inspect a pipe or the like and is inserted by pushing in the insertable part. The longer the insertable part, the farther the inserting operating point from the tip of the insertable part. Due to the frictional resistance of the tip, the insertable part will buckle and will become difficult to insert. Therefore, the longer the insertable part, the more rigid the insertable part must be made.

Therefore, in the conventional drum, the longer the insertable part and the lower the flexibility, the larger the diameter of the drum must be and therefore the weight and lack of portability are problems.

Shown in the following are three examples of such apparatus wherein the insertable part can be wound up on a drum and an imaging means is provided.

The first example is an apparatus disclosed in the publication of a Japanese patent application laid open No. 164688/1981. As shown in FIG. 66, this apparatus has an image guide 1101 as an elongate insertable part and a drum for winding up this image guide and an objective lens 1103 is provided on the tip of the above mentioned image guide 1101 so that an object image formed by the objective lens 1103 may be transmitted into the drum 1102 by the image guide 1101 and may be imaged by a television camera 1105 provided within this drum 1102 and the image imaged by this television camera 1105 may be displayed in a monitor television 1106.

However, in this prior art example, the image guide is used, is a bundle of 10,000 to 30,000 fibers and has therefore a problem that the resolution is low. Also, as the image attenuated through the image guide is imaged by the television camera, there is a problem that the sensitivity will be low.

Therefore, such imaging apparatus as is shown in FIG. 67 is considered as the second example.

The apparatus of this second example has a cable 1111 as an elongate insertable part and a drum on which the cable 1111 can be wound up and a television camera 1112 is provided in the tip part of the above mentioned cable 1111. The above mentioned cable 1111 is led into the drum 1102 and is then extended out of the side of the drum 1102. This cable 1111 contains a current source line 1113 for feeding a current source for operating the above mentioned television camera 1112 and a signal line 1115 for delivering a video signal which is an output of the television camera 1112. The above mentioned current source line 1113 is connected to a current source unit 1114 outside the drum 1102 and the signal line 1115 is connected to a monitor television 1106 outside the drum 1102. The above mentioned television camera 1112 is formed as shown in FIG. 68. That is to say, the television camera 1112 has an objective lens 1107, a (solid state) imaging device 1108 arranged in the image forming position of this objective lens 1107 and a signal circuit part 1109 for operating this imaging device 1108 and outputting a video signal.

In this apparatus of the second example, an object is imaged directly by the television camera, 200,000 to 300,000 pixels are used in the television camera and are several tens times as many as in the image guide and therefore the resolution is high. However, there is a problem that the television camera 1112 has the signal circuit part 1109 and is therefore so large in size as not to be insertable into a fine tube or the like.

The third example is shown in the publication of a Japanese patent application laid open No. 75315/1986. As shown in FIG. 69, this apparatus is provided with an elongate insertable part 1121 and a tip part 1122 containing only an objective lens, imaging device and supersmall electric parts is provided at the tip of this insertable part 1121. A camera controlling part 1152, light source part 1153 and monitor part 1154 are contained in a unit body 1151 which is not rotated of a drum unit. By the way, the insertable part 1121 is to be wound up on a rotatable rotary part 1156 provided on the outer peripheral part of the above mentioned unit body 1151.

In this apparatus, as the unit body 1151 is a part which is not rotated, a signal must be transmitted between the rotary part 1151 and unit body 1151. In the specification of the Japanese patent application laid open No. 75315/1986, as shown in FIG. 70, an electric signal is to be transmitted between the rotary part 1156 and unit body 1151 through a curled cord 1159. However, there is a problem that the durability of the curled cord is low. A slip ring must be used.

An example of the structure of the above mentioned slip ring is shown in FIG. 71. In this slip ring 1133, a plurality of concentric circular electrodes 1143 are arranged on a plate 1142 not rotated together with a fixed shaft 1141 and electric wires $U_1$, $U_2$, $U_{18}$ are connected to the respective electrodes 1143 and are connected to the unit body 1151. On the other hand, brush-like electrodes 1146 are provided to rotate and move together with a rotating cover 1145 and are in contact respectively with the above mentioned electrodes 1143. The respective brush-like electrodes 1143 are contacted with the imaging device. As illustrated, the above mentioned electrodes 1143 and 1146 are made, for example, 18 pairs respectively corresponding to signals $t_1$ to $t_{18}$. The details of these signals $t_1$ to $t_2$ are as illustrated. Among them, $\phi R$, $\phi H_4$, $\phi H_3$, $\phi H_2$, $\phi H_1$, $\phi V_4$, $\phi V_3$, $\phi V_2$ and $\phi V_1$ are driving pulses required to operate the imaging device and PT, $V_{sub}$ and $V_{DD}$ are direct current voltages required to also operate the imaging device. $V_{out}$ and $D_{MY}$ are video signals output from the imaging device and delivered to a camera controlling unit 1152. $G_1$ and $G_2$ are earthing lines. The total of these necessary signal lines will be 16 poles even if options to be used for future expansion are excepted.

Thus, as in the apparatus of the third example, if the imaging device and signal circuit part are separated from each other, very many signal lines will have to be connected between them. Therefore, the slip ring 1133 will become large and very expensive. Further, the above mentioned pulses to operating the imaging device are of high frequencies and, if they are led to such exposed conductors as the poles 1143 and 1146, electromagnetic waves will be radiated in the space and will be likely to affect nearby televisions, radios and wireless instruments.

If the slip ring is between the imaging device and signal processing circuit, the noise mixed in by the slip ring will be amplified and the S/N ratio will be reduced.

OBJECTS AND SUMMARY OF THE INVENTION

An object of the present invention is to provide an endoscope wherein the insertable part can be housed as wound up on a winding member, the winding member can be made light and small and the portability, workability and operability can be increased.

Another object of the present invention is to provide an endoscope apparatus wherein the insertable part can be housed as wound up on a winding member and the space for housing the winding unit can be made small.

A further object of the present invention is to provide an endoscope apparatus wherein the insertable part can be housed as wound up on a winding member, a long insertable part having low flexibility can be housed, the winding unit can be made small and light and the portability can be increased.

Another further object of the present invention is to provide an endoscope apparatus wherein the insertable part can be wound up and housed, it is not necessary to use a multipole slip ring which is large, expensive and detrimental, the insertable part can be made small at the tip and a favorable video image high in resolution can be obtained.

Further, another object of the present invention is to provide an endoscope apparatus wherein the insertable part can be wound up and housed on a winding member and noise can be reduced.

The endoscope apparatus of the present invention comprises an elongate insertable part having an illuminating window and an observing window in the tip part, a winding unit having a winding member fitted with the above mentioned insertable part at the base end and capable of winding up and housing the above mentioned insertable part and a supporting part rotatably supporting the winding member, an illuminating means for emitting an illuminating light from the above mentioned illuminating window and an observing means for making an object observable by receiving the light from the object incident from the above mentioned observing window. An external apparatus forming at least one of the above mentioned illuminating means and observing means is provided separately from the above mentioned winding member and a lead-out means forming at least one of the above mentioned illuminating means and observing means, extended in the axial direction out of the side of the above mentioned winding member and connected to the above mentioned external apparatus is provided.

Also, the endoscope apparatus comprises an insertable part having an observing window in the tip part, a winding member capable of winding up and housing the above mentioned insertable part, an imaging means provided in the tip part of the above mentioned insertable part, for receiving the light from an object incident from the observing window and imaging the object image, and a video processor including a driving circuit for feeding driving pulses to the above mentioned imaging means and a signal processing circuit for processing the picture image signal output from the above mentioned imaging means to be a video signal. At least the driving circuit may be fitted to the winding member so as to rotate together with this winding member, and/or the above mentioned signal processing circuit may be fitted in at least in part to the winding member.

The other features and advantages of the present invention will become apparent enough with the following explanation.

BRIEF DESCRIPTION OF THE DRAWINGS

FIG. 1 is a perspective view showing an entire endoscope apparatus.

FIG. 2 is an explanatory view showing a drum interior and light source connector.

FIG. 3 is an explanatory view showing schematically the construction of an endoscope apparatus.

FIG. 4 is a block diagram showing the formation of a video processor.

FIG. 5 is a block diagram showing the formation of a processing circuit.

FIG. 6 is a sectional view showing the tip part of an insertable part.

FIG. 7 is a sectional view of a drum.

FIG. 8 is a side view of a drum as partly sectioned.

FIG. 9 is a sectional view of the side of a drum shown as magnified.

FIG. 10 is a sectional view of a light source connector.

FIG. 11 is a magnified sectional view of the part A in FIG. 10.

FIG. 12 is a perspective view showing an entire endoscope apparatus.

FIG. 13 is an explanatory view showing the formation of an endoscope apparatus.

FIG. 14 is an explanatory view showing the formation of an endoscope apparatus.

FIG. 15 is a sectional view showing an optical fiber light guide extending out of a drum.

FIG. 16 is a sectional view of a light source connector.

FIG. 17 is an explanatory view showing a modification of an optical fiber light guide extending out of a drum.

FIG. 20 is a perspective view showing an entire endoscope apparatus.

FIG. 21 is an explanatory view showing schematically the structure of an endoscope apparatus.

FIG. 22 is a sectional view of a drum.

FIG. 23 is an explanatory view showing schematically the structure of an endoscope apparatus.

FIG. 24 is a sectional view showing the tip part of an insertable part.

FIG. 25 is a sectional view of a drum.

FIG. 26 is a perspective view showing an entire

FIG. 27 is an explanatory view showing schematically the structure of an endoscope.

FIGS. 28 to 32 relate to the ninth embodiment of the present invention.

FIG. 28 is a perspective view showing an entire endoscope apparatus.

FIG. 29 is an explanatory view showing schematically the structure of an endoscope apparatus.

FIG. 30 is a sectional view of a drum.

FIG. 31 is a sectional view of a light source connector.

FIG. 32 is a sectional view on line B—B' in FIG. 31.

FIG. 33 is an explanatory view showing schematically the structure of an endoscope.

FIG. 34 is a sectional view of a light source connector.

FIG. 35 is a sectional view on line C—C' in FIG. 34.

FIG. 36 is a block diagram showing a video processor.

FIG. 37 is a block diagram showing a processing circuit.

FIGS. 38 to 40 relate to the eleventh embodiment of the present invention.

FIG. 38 is a sectional view of a drum.

FIG. 39 is an explanatory view showing a still camera.

FIG. 40 is an explanatory view showing a displaying apparatus.

FIG. 41 is a sectional view showing a light fiber guide extending out of a drum in the twelfth embodiment of the present invention.

FIG. 42 is a sectional view of a drum in the thirteenth embodiment of the present invention.

FIG. 43 is a perspective view showing an endoscope apparatus being carried.

FIG. 44 is a sectional view showing the vicinity of a roller.

FIG. 46 is an explanatory view showing schematically the structure of an endoscope apparatus.

FIG. 47 is a sectional view of a drum.

FIG. 49 is an explanatory view showing the structure of an endoscope apparatus.

FIG. 50 is an explanatory view showing the tip part of an insertable part.

FIG. 51 is a block diagram showing the formation of a signal circuit part.

FIG. 52 is an explanatory view showing a signal circuit part fitting part.

FIG. 53 is an explanatory view showing a slip ring and rotary transformer in a modification of this embodiment.

FIG. 54 is a perspective view of a rotary transformer.

FIG. 55 is a sectional view of a rotary transformer.

FIG. 58 is an explanatory view showing the structure of an endoscope apparatus.

FIG. 59 is a block diagram showing the formation of a signal circuit part.

FIG. 60 is a block diagram showing the structure of a signal processing apparatus.

FIG. 61 is an explanatory view showing the structure of an endoscope apparatus.

FIG. 62 is a block diagram showing the formation of a signal circuit part.

FIG. 64 is a block diagram showing the structure of a picture image processing apparatus.

FIG. 66 is an explanatory view showing the first example of a winding type imaging apparatus.

FIG. 67 is an explanatory view showing the second example of a winding type imaging apparatus.

FIG. 68 is an explanatory view showing the structure of the tip part of the apparatus in FIG. 67.

FIG. 69 is a perspective view showing the third example of a winding type imaging apparatus.

FIG. 70 is an explanatory view showing the drum interior of the apparatus in FIG. 69.

FIG. 71 is an explanatory view showing an example of a slip ring.

DETAILED DESCRIPTION OF PREFERRED EMBODIMENTS

FIGS. 1 to 11 show the first embodiment of the present invention.

Figure 1:
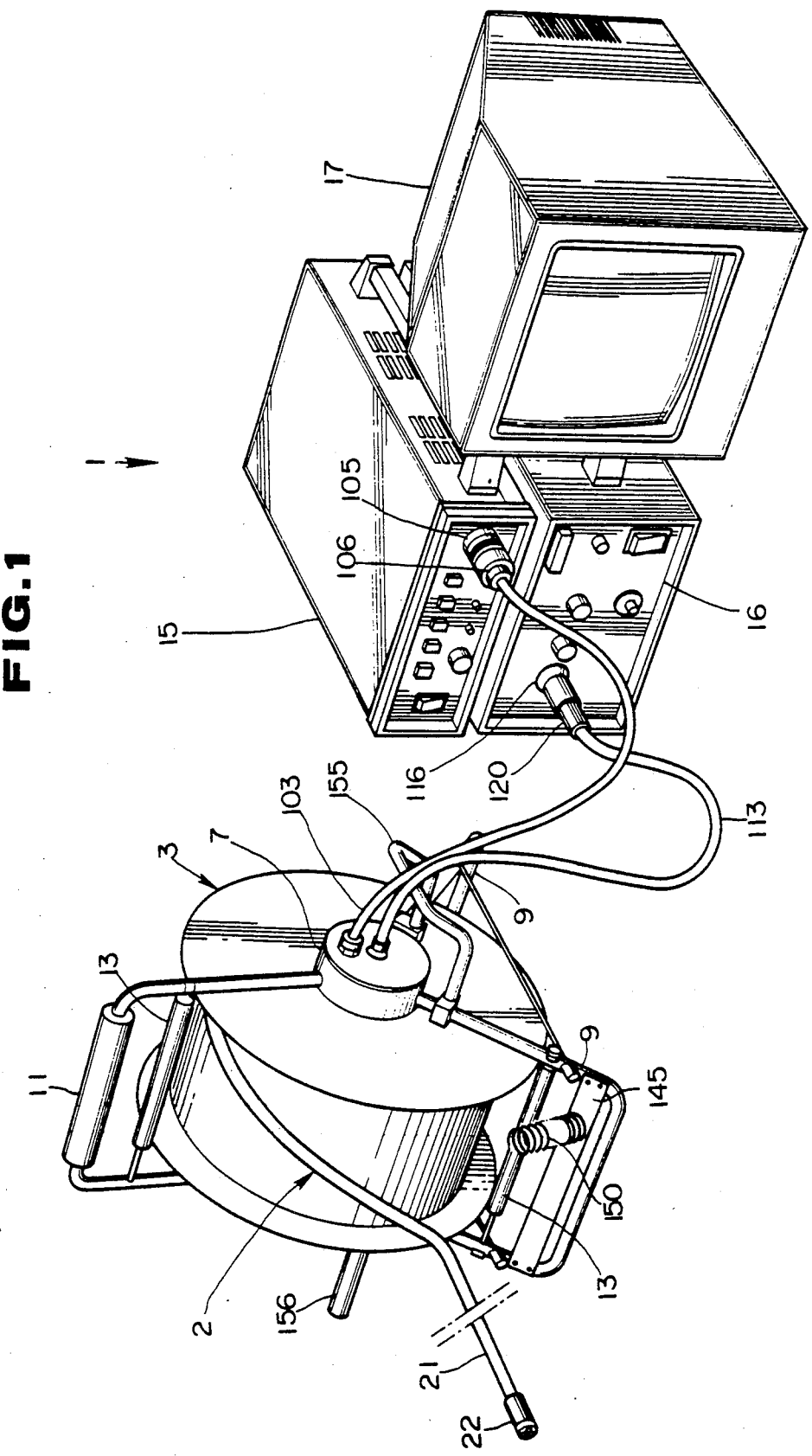
FIGS. 1 to 11 relate to the first embodiment of the present invention.

As shown in FIG. 1, an endoscope apparatus 1 is provided with an elongate flexible (endoscope) insertable part 2 which is fixed at its base end to a drum 3 so as to be housed as wound up on this drum 3. The endoscope apparatus is provided also with a video processor 15, light source apparatus 16 and monitor 17 separately from the above mentioned drum.

Figure 2:
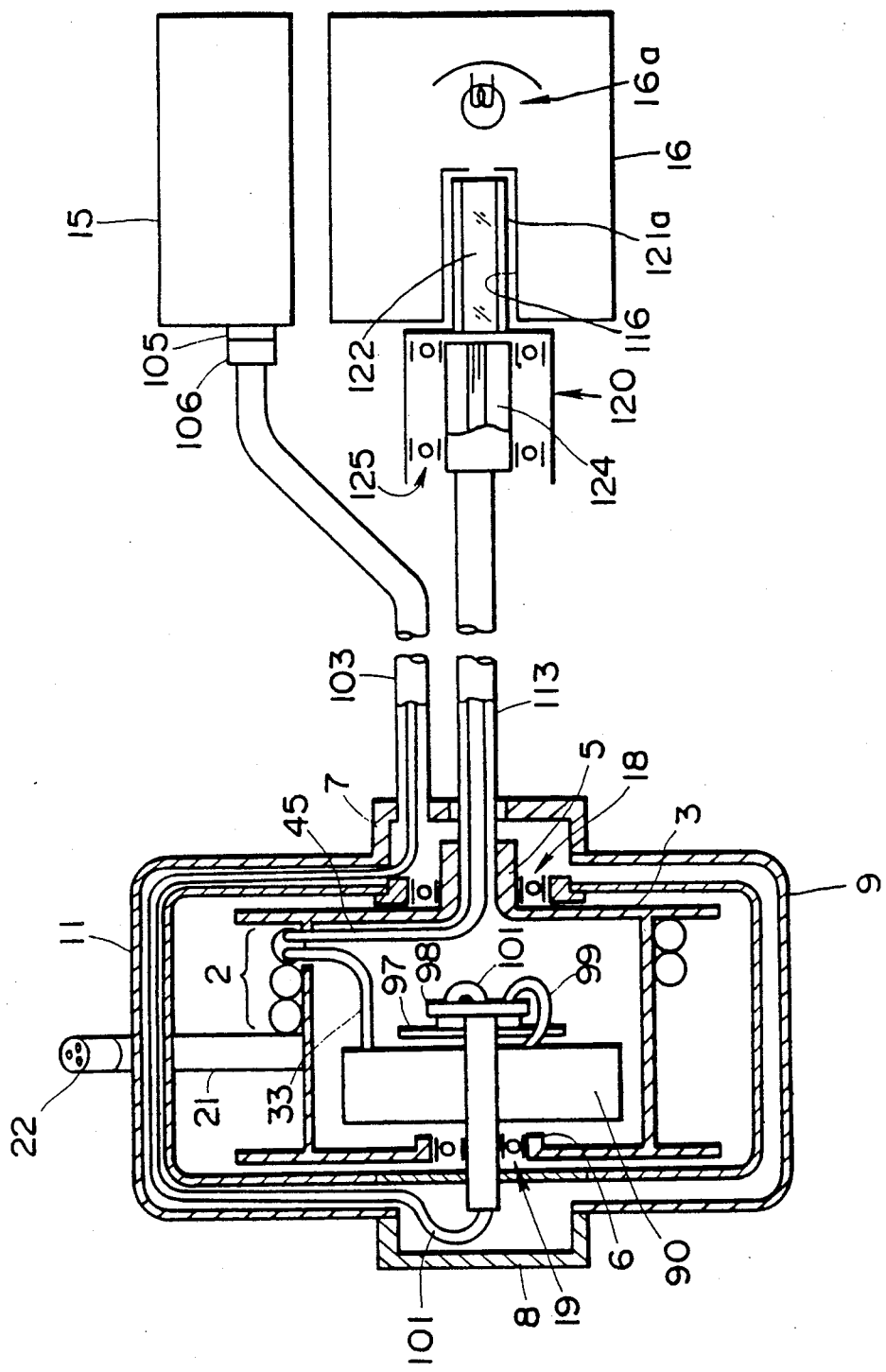
Figure 3:
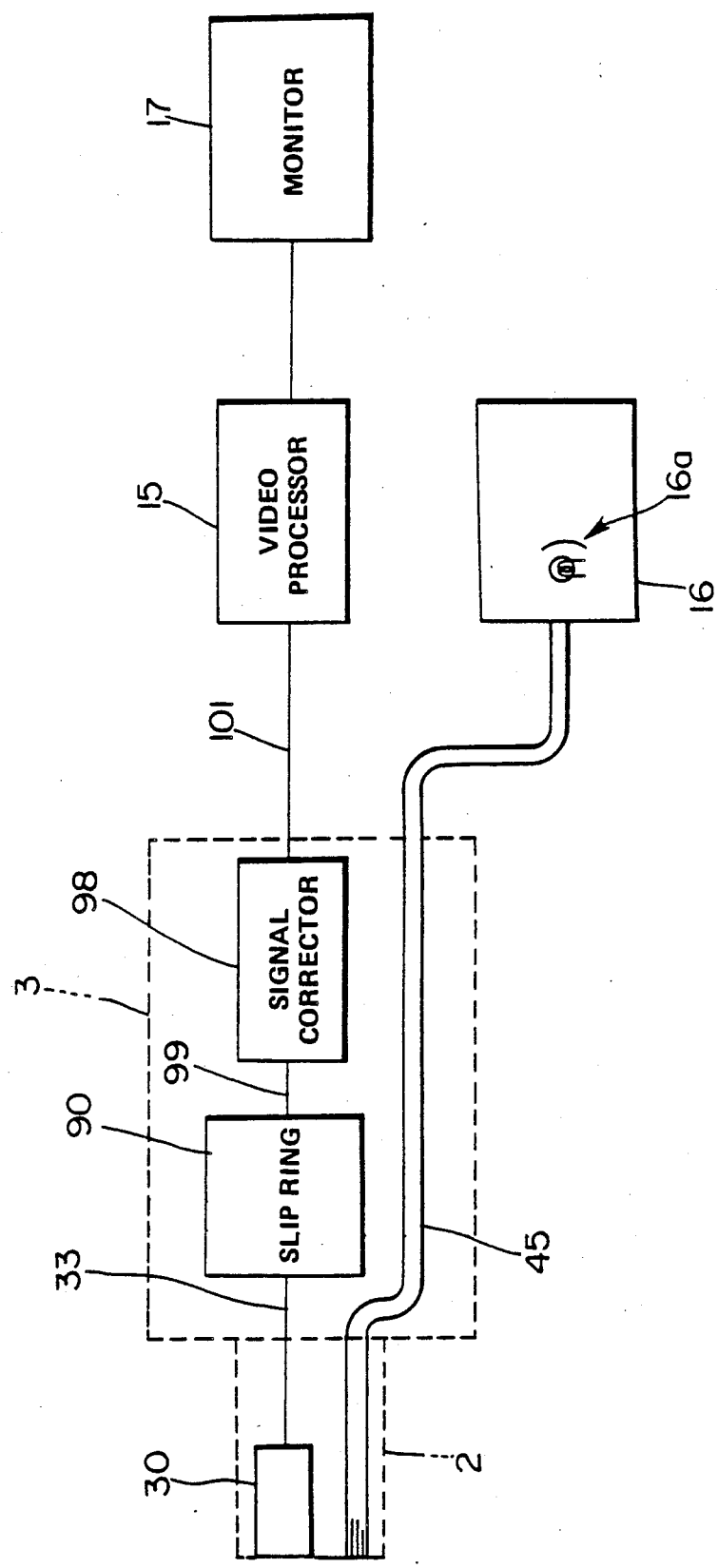
Figure 7:
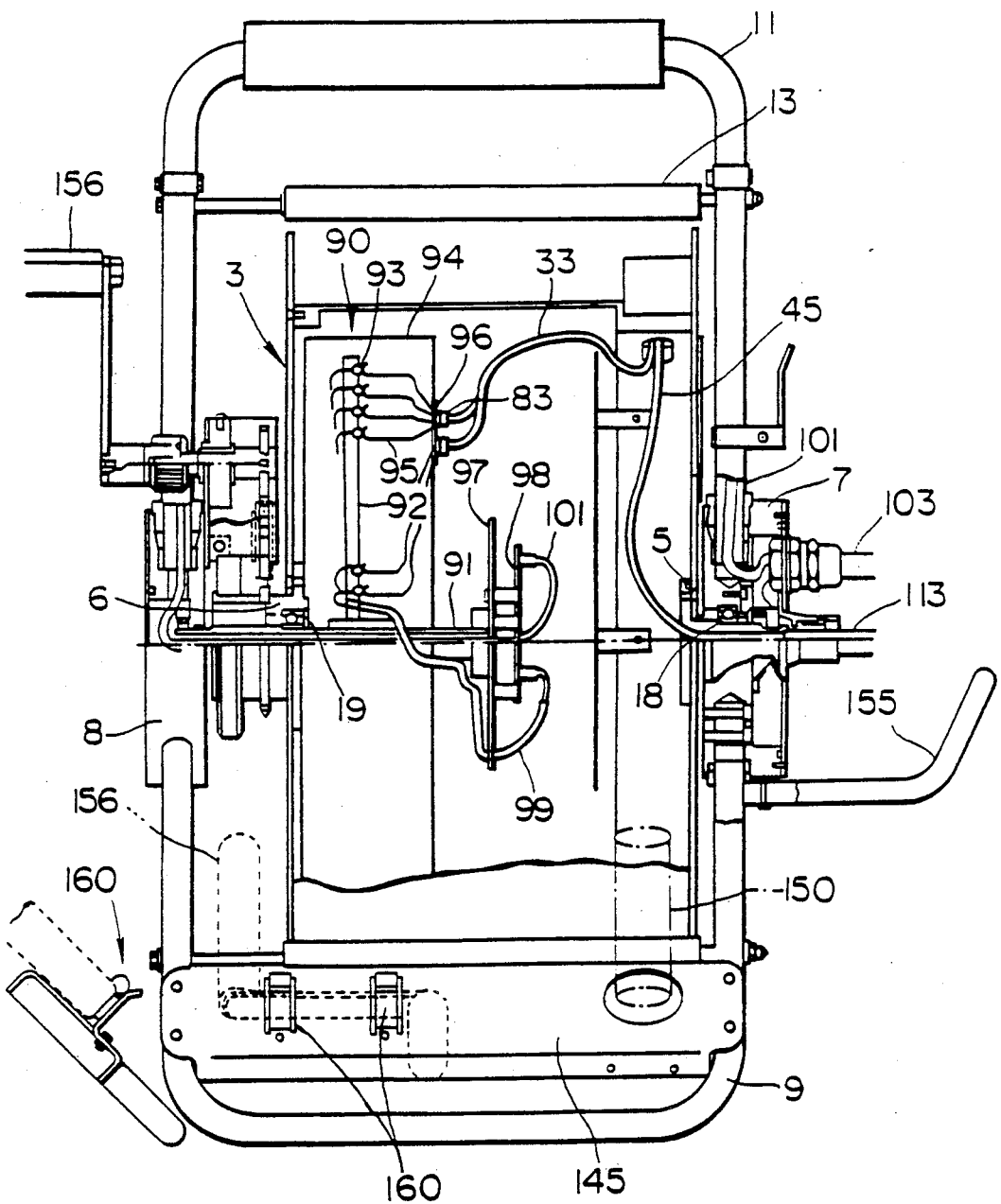

As shown in FIGS. 2 and 7, the above mentioned drum 3 is provided at both ends in the rotary axial direction with cylindrical rotary shafts 5 and 6 which are rotatably supported respectively by bearing parts 7 and 8 through bearings 18 and 19. Leg-like frames 9 rotatably supporting the above mentioned drum 3 are provided on the lower side between the above mentioned bearing parts 7 and 8. A handle 11 for carrying the above mentioned drum 3 is provided on the upper side between the above mentioned bearing parts 7 and 8 and is formed of a pipe.

Rollers 13 are rotatably fitted respectively to the above mentioned frames 9 and handle 11 so as to be opposed to the peripheral surface of the drum 3. The above mentioned insertable part 2 is inserted between the peripheral surface of the above mentioned drum 3 and the above mentioned rollers 13 so as to be wound up on the drum 3 and to be limited by the above mentioned rollers 13 in the amount of expansion in the outer peripheral direction of the wound insertable part.

Figure 6:
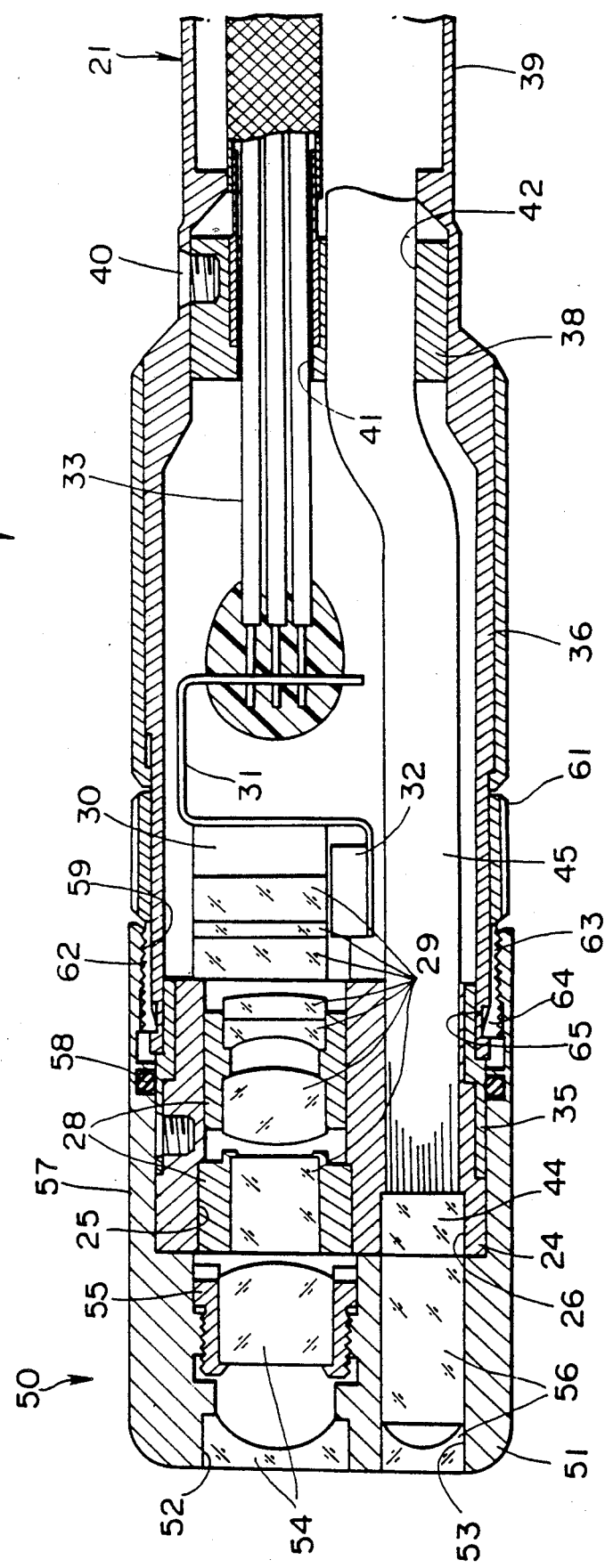

On the other hand, the above mentioned insertable part 2 is formed by connecting a rigid tip part 22 to the tip of a flexible pipe having a desired amount of flexibility. The above mentioned tip part 22 is formed as shown in FIG. 6.

That is to say, the above mentioned tip part 22 is provided with a rigid tip body 24 in which an observing hole 25 and illuminating hole 26 are formed in the lengthwise direction of the insertable part 2. A part of an objective lens system 29 held by a lens frame 28 is fitted in the above mentioned observing hole and the other parts of the objective lens system 29 are bonded to the rear end part of the above mentioned tip body 24. A solid state imaging device 301 is secured to the rear end surface of the above mentioned objective lens system 29 and is fixed on a flexible substrate 31 on which an electronic part 32 is fitted. Signal lines 33 are connected to the rear end part of the above mentioned flexible substrate 31, are inserted through the above mentioned flexible pipe 21 and are extended out of the base end of the insertable part 2.

A cylindrical cover member 36 is connected to the rear end part of the above mentioned tip body 24 through a connecting ring 35 and contains the above mentioned solid state imaging device 30 and flexible substrate 31. A columnar fixing member 38 is fixed to the rear end part of this cover member 36 and has an outer cover 39 of the above mentioned flexible pipe 21 fixed in the tip part, for example, with a screw 40. A signal line inserting hole 41 and light guide inserting hole 42 are formed through the above mentioned fixing member 38. The above mentioned signal lines 33 are inserted and fixed through the above mentioned signal line inserting hole 41.

A light distributing lens 44 is fitted in the above mentioned illuminating hole 26. A light guide 45 of fibers is connected to the rear end of the light distributing lens 44, is inserted through the light guide inserting hole 42 of the above mentioned fixing member 38, is further inserted through the above mentioned flexible pipe 21 and is extended out of the base end of the insertable part 2.

A tip adapter 50 is fitted to the tip side of the above mentioned tip body 24 and is provided with a substantially columnar adapter body 51 in which an observing hole 52 and illuminating hole 53 are formed in the lengthwise direction of the insertable part 2 in the positions corresponding respectively to the observing hole 25 and illuminating hole 26 of the above mentioned tip body 24. A lens system 54 forming an image forming optical system together with the above mentioned objective lens system 29 is fitted in the above mentioned observing hole 52. A part of this lens system 54 is held by a lens frame 55 screwed in the above mentioned observing hole 52 so as to be free to advance and retreat. The focusing of the lens system can be adjusted by advancing and retreating the above mentioned lens frame 55. By the way, the above mentioned lens system 54 can vary, for example, the field area and visual field. A light distributing lens system 56 is fitted in the above mentioned illuminating hole 53.

The above mentioned adapter body 51 is formed to be cylindrical on the rear end and is externally fitted at the cylindrical part 57 on the above mentioned tip body 24. An 0-ring 58 is interposed between the above mentioned cylindrical part 57 and tip body 24. A female screw thread 59 is formed in the rear end part of the above mentioned cylindrical part 57. On the other hand, a connecting ring 61 is rotatably loosely fitted on the outer peripheral part of the above mentioned cover member 36. A male screw thread 62 screwed with the above mentioned female screw thread 59 is formed on the outer peripheral surface of the front part of the above mentioned connecting ring 61. A plurality of slits 63 are formed in the lengthwise direction in the front part of the connecting ring 61 on which this male screw thread 62 is formed. An inward projecting projection 64 is formed in the front end part of the connecting ring 61 and is engaged in a recess 65 formed on the outer peripheral part of the above mentioned cover member 36 so that, when the male screw thread 62 of the connecting ring 61 is screwed with the female screw thread 59 of the above mentioned adapter body 51, the above mentioned tip adapter 50 will be fixed to the tip body 24.

Figure 8:
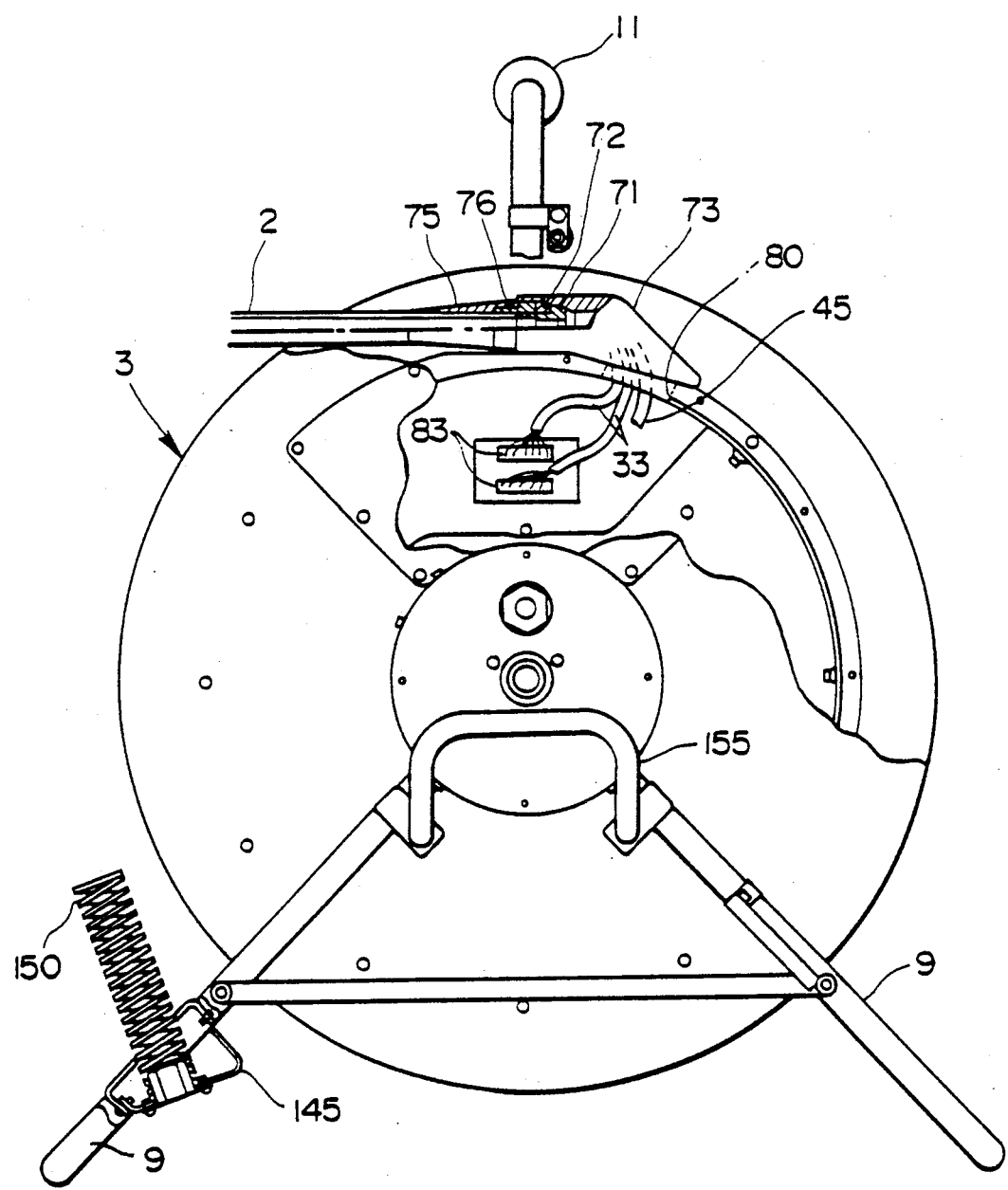

The above mentioned insertable part 2 is formed in the base part as shown in FIG. 8.

That is to say, a substantially tubular mouthpiece 71 is connected to the rear end part of the flexible pipe 21 of the insertable part 2. This mouthpiece 71 is formed to be large in the diameter on the rear end on the outer peripheral part and has a mouthpiece retainer 72 loosely fitted on the small diameter part on the front end. A male screw thread is formed on the outer peripheral part of this mouthpiece retainer 72 An insertable part holder 73 is externally fitted to the above mentioned mouthpiece 71. A female screw thread to be screwed with the male screw thread of the above mentioned mouthpiece retainer 72 is formed on the front end side of this insertable part holder 73. The above mentioned mouthpiece 71 is held by the mouthpiece retainer 72 and insertable part holder 73. By the way, an 0-ring not illustrated is interposed between the above mentioned mouthpiece 71 and insertable part holder 73. A substantially cylindrical buckling preventing member 75 is externally fitted on the insertable part 2 on the front side of the above mentioned insertable part holder 73. A ring-like connecting member 76 is fixed to the rear end part of this buckling preventing member 75. A male screw thread to be screwed with the female screw thread of the above mentioned insertable part holder is formed on the outer peripheral part of this connecting member 76. The above mentioned buckling preventing member 75 is connected and fixed to the above mentioned insertable part holder 73 by screwing the male screw thread with the female screw thread.

Now, as shown in FIG. 8, an insertable part fitting hole 80 is formed in the peripheral part of the above mentioned drum 3. The above mentioned insertable part holder 73 is to be fixed with respect to the above mentioned drum 3 so as to cover the above mentioned insertable part fitting hole 80.

A path communicating with an internal cavity of the above mentioned insertable part 2 is formed in the above mentioned insertable part holder 73 and is bent and formed so as to communicate with the insertable part fitting hole 8 of the above mentioned drum 3.

Figure 10:
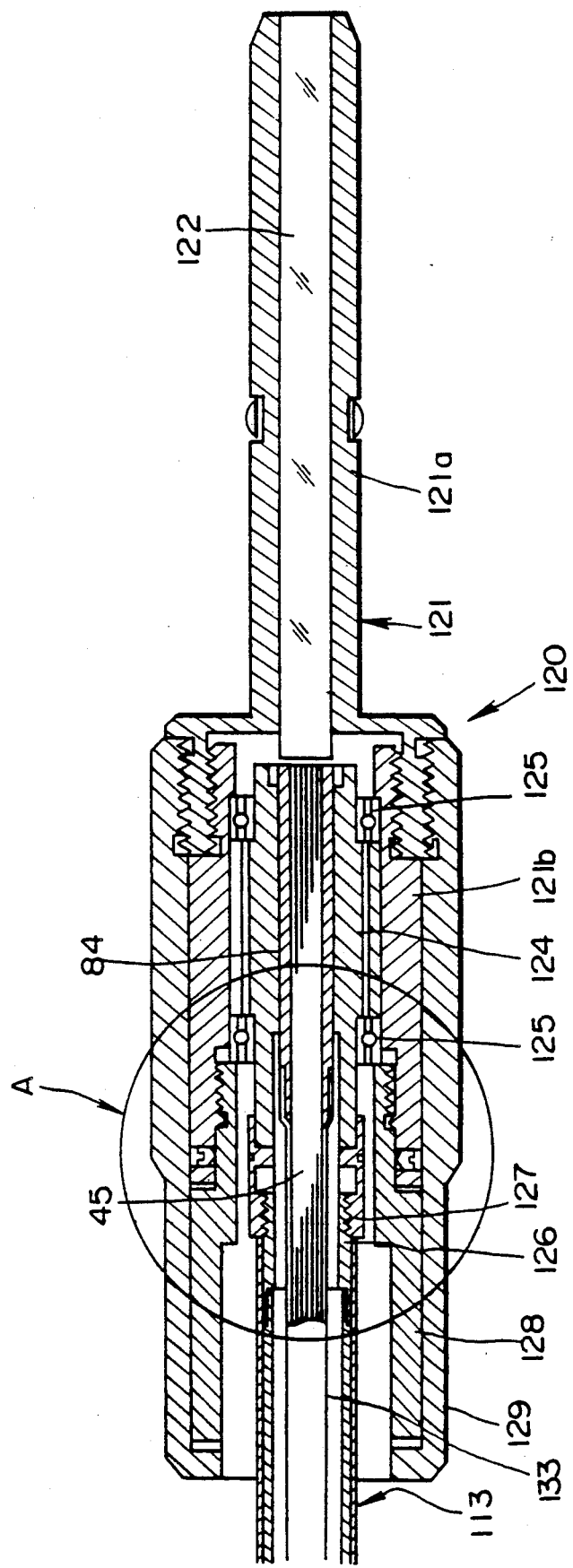

As shown in FIG. 8, the signal lines 33 and optical fiber light guide 45 inserted through the above mentioned insertable part 2 pass through the path in the above mentioned insertable part holder 73, are extended out of this insertable part holder 73, are inserted through the insertable part fitting hole 80 in the above mentioned drum 3 and are led into this drum 3. The above mentioned signal lines 33 are fitted at the base ends with plugs 83. The above mentioned optical fiber light guide 45 is fitted at the base end with a tip pipe as shown in FIG. 10.

As shown in FIG. 7, a slip ring (rotary electric contact) 90 is provided within the above mentioned drum 3 and is provided with a fixed shaft 91 fixed to the bearing part 8, a disc-like fixed plate 92 fixed to this fixed shaft 91, fixed rings 93 provided on this fixed plate 92, a rotor 94 rotating together with the drum 3 with the above mentioned fixed shaft 91 as a center, slip ring brushes 95 in sliding contact with the above mentioned fixed rings 93 and receptacles 96 provided on the side of the above mentioned rotor 94 and connected to the above mentioned slip ring brushes 95. The plugs S3 provided at the base ends of the above mentioned signal lines 33 are connected to the above mentioned receptacles 96. A terminal plate 97 is fitted to the above mentioned fixed shaft 91 and is provided with a signal correcting circuit 98 for shaping the waveform or the like. Signal lines 99 connected to the above mentioned fixed rings 93 are connected to the above mentioned signal correcting circuit 98. A signal line 101 is connected to the above mentioned signal correcting circuit 98, is inserted through the hollow part of the above mentioned fixed shaft 91, is extended out of the side of the drum 3, is inserted through the hollow part of the handle 11 from one bearing part 8 and is led into the other bearing part 7. A signal cable 103 is connected to the side of this bearing part 7. The above mentioned signal line 101 is inserted through this signal cable 103. A connector 106 removably connectable to a connector receptacle 105 of the video processor 15 is provided at the tip of this signal cable 103. The above mentioned signal line 101 is connected to this connector 106.

Thus, the solid state imaging device 30 provided in the tip part 22 of the insertable part 20 is to be connected to the above mentioned video processor 15 through the signal the signal lines 33, plugs 83, receptacles 96, slip ring brushes 95, fixed rings 93, signal lines 99, signal correcting circuit 98, signal line 101, connector 106 and connector receptacle 105 and is driven by a driver within the above mentioned video processor 15. The output signal is processed to be a video signal by the above mentioned video processor 15. The video signal produced by this video processor is input into the monitor 17 in which an observed image is displayed.

Figure 9:
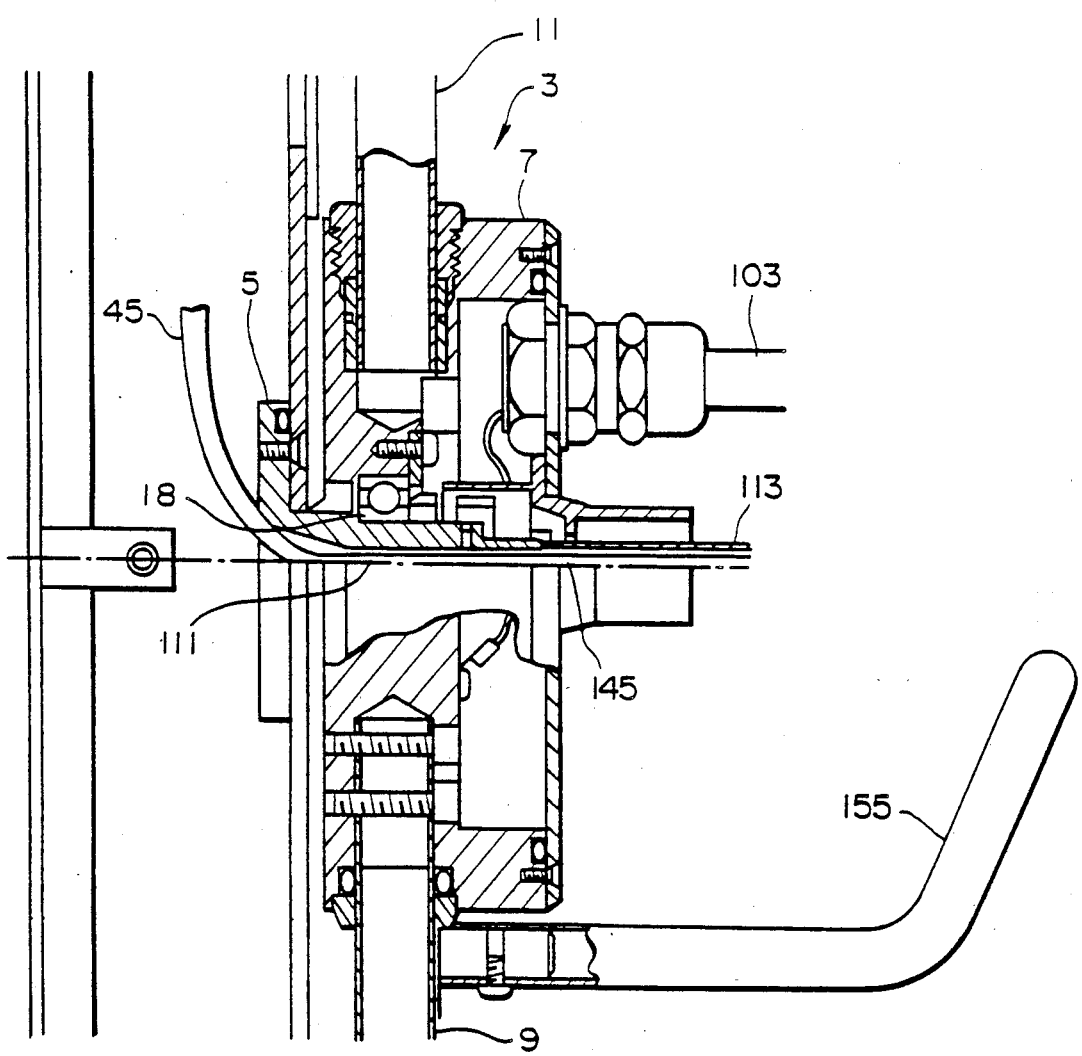

On the other hand, as shown in FIGS. 2, 7 and 9, the fiber light guide 45 led into the above mentioned drum 3 is inserted through a center hole 111 of the rotary shaft part 5 and is extended in the rotary axial direction out of the bearing part 7 fitted with the above mentioned signal cable 103.

A flexible connecting cable 113 is connected at the base end by a nut 145 to the middle of the side of the above mentioned rotary shaft part 5 and the above mentioned light guide 45 is inserted through this connecting cable 113. A light source connector 120 removably connectable to a connector receptacle 116 of the light source apparatus 16 is provided at the tip of the above mentioned connecting cable 113. The connecting cable 113 may also be covered with a flexible hose 114 as described hereinafter with respect to FIGS. 14 and 15.

Figure 11:
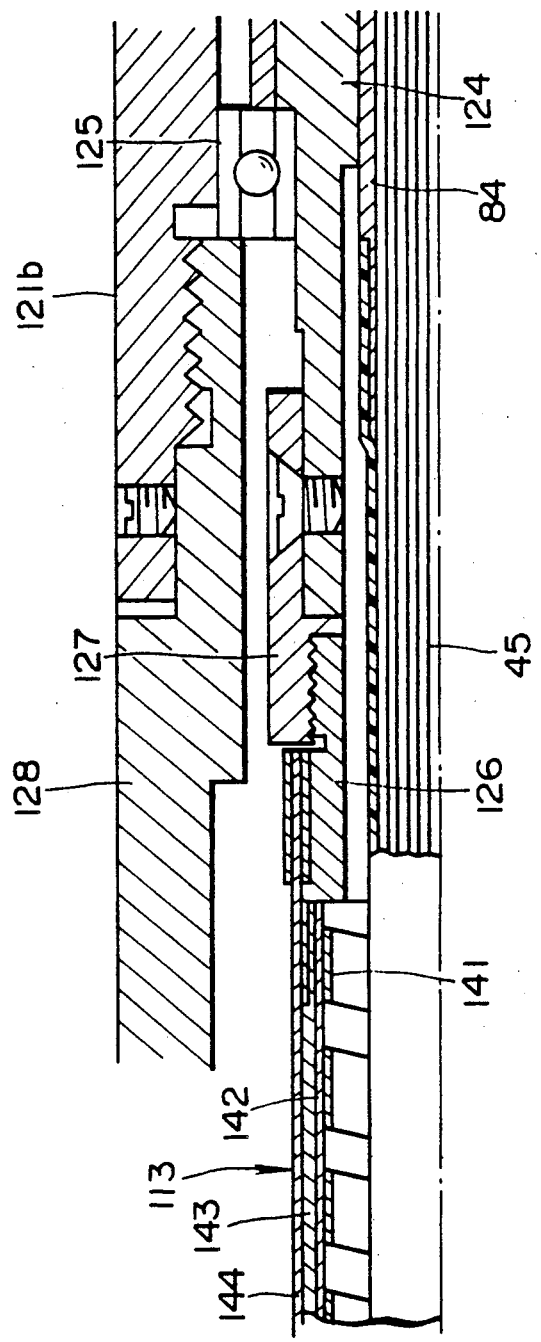

The above mentioned light source connector 120 is formed as shown in FIGS. 10 and 11.

The light source connector 120 is provided with a connector body 121 comprising a cylindrical small diameter part 121a on the tip side and a cylindrical large diameter part 1221b. A columnar rod lens 122 formed of a single fiber having a core and covering is contained and fixed within the above mentioned small diameter part 121a. On the other hand, the light guide 45 is inserted and arranged in the end part within the above mentioned large diameter part 121b opposite the rear end part of the above mentioned rod lens 122 so that the optical axes may coincide with each other. This light guide 45 is projected at the end out of the end of the above mentioned connecting cable 113 and is fixed to a rotary mouthpiece 124 through the tip pipe 84. This rotary mouthpiece 124 is rotatably held within the above mentioned large diameter part 121b through bearings 125. The above mentioned connecting cable 113 is fitted at the end with a connecting mouthpiece 126 which is connected and fixed to the rear end of the above mentioned rotary mouthpiece 124 through a connecting ring 127. Therefore, the above mentioned light guide 45 and connecting cable 113 are rotatable with respect to the above mentioned connector body 121 and rotate with the rotation of the drum 3.

A tube body 128 is connected and fixed to the rear end of the above mentioned connector body 121. The light guide 45 held by the above mentioned bearings 125 and rotary mouthpiece 124 is prevented by this body 128 from being pulled out. A tubular cover member 129 is screwed to the large diameter part 121b of the above mentioned connector body 121 and the outer peripheral part of the tube body 128.

By the way, as shown in FIG. 11, the above mentioned connecting cable 113 is formed, for example, of a spiral tube 141, net tube 142 and double cover tube 143, in that order from inside.

As shown in FIG. 2, the small diameter part 121a of the above mentioned connector body 121 is inserted into the connector receptacle 116 so that the tip surface of the rod lens 122 within this small diameter part 121a may be opposed to a lamp 16a within the light source apparatus. The above mentioned light guide 45 and connecting cable 113 are rotatable with respect to the above mentioned connector body 121 and are therefore rotatably connected to the above mentioned light source 16.

In this embodiment, as shown in FIG. 1 and others, a holder fitting plate 145 is provided on one frame 9 and is fitted with a tip holder 150 holding and protecting the tip part 22 of the insertable part 2 at such time as of housing the insertable part 2. This tip holder 150 may be a coil spring as shown in FIG. 8 or may be a pipe or the like. The material may be a metal, plastics or the like. The tip part 22 can be protected by being inserted into the above mentioned tip holder 150 made of a coil spring or pipe and therefore can be protected from a shock from outside.

As shown in FIG. 1 and others, a guard 155 for protecting the above mentioned signal cable 103 and connecting cable 113 is provided between the sides of the frames 9 on the side on which the above mentioned signal cable 103 and connecting cable 113 are extended out.

An insertable part winding foldable handle 156 connected to the side of the drum 3 to rotate the drum 3 is provided on the side opposite the side out of which the above mentioned signal cable 103 and connecting cable 113 are extended. A handle holder 160 housing the above mentioned insertable part winding handle 156 is provided below the above mentioned drum 3.

Figure 4:
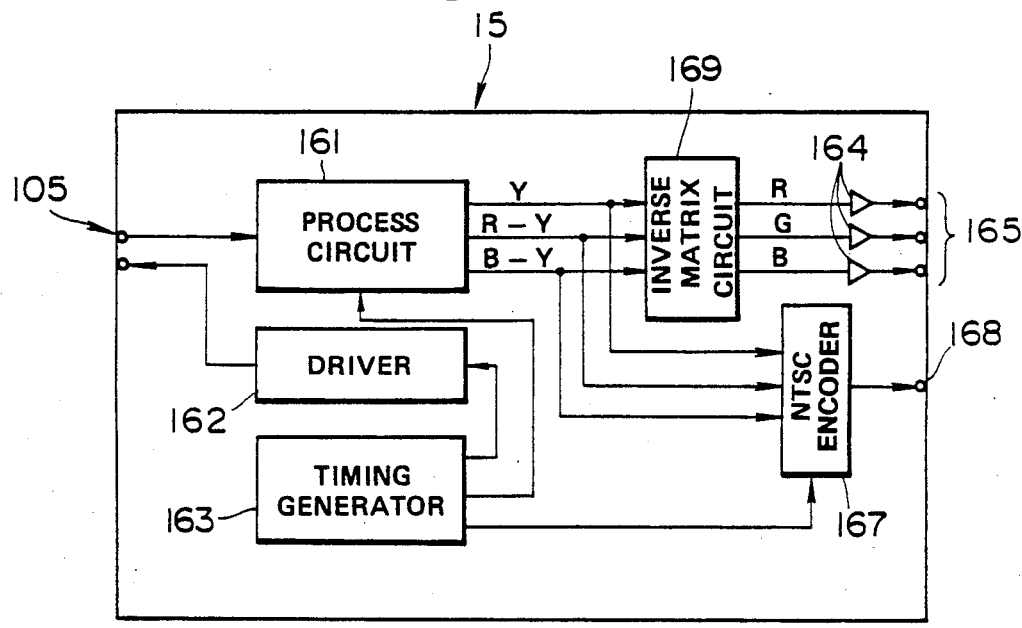

Now, the above mentioned video processor 15 is formed, for example, as shown in FIG. 4.

That is to say, in the case of using a synchronous type color imaging system, the above mentioned video processor 15 is provided with a processing circuit 161 for processing the output signal of the solid state imaging device 30 to be a video signal and a driver 162 for applying driving pulses to the above mentioned solid state imaging device 30 both of which are connected to the connector receptacle 105. The output signal of the solid state imaging device 30 driven and read out by the above mentioned driver 162 is amplified by a pre-amplifier and is then input into the above mentioned processing circuit 161 and, for example, a luminance signal y and color difference signals R-Y and B-Y are output. The above mentioned luminance signal Y and color difference signals R-Y and B-Y are input into an NTSC encoder 167, are converted to an NTSC system composite video signal which is output out of an NTSC output terminal 168. Also, the above mentioned luminance signal Y and color difference signals R-Y and B-Y are input into an inverse matrix circuit 169 and are converted to color signals R, G and B which are output out of a three-primary color output terminal 165 through drivers 164. By the way, the above mentioned processing circuit 161, driver 162 and NTSC encoder 167 are controlled in timing by a timing generator 163. By the way, as shown in FIG. 5, a color filter array 171 in which color filters transmitting respectively such color lights as of red (R), green (G) and blue (B) are arranged in the form of a mosaic or the like is provided on the front surface of the above mentioned solid state imaging device 30.

Figure 5:
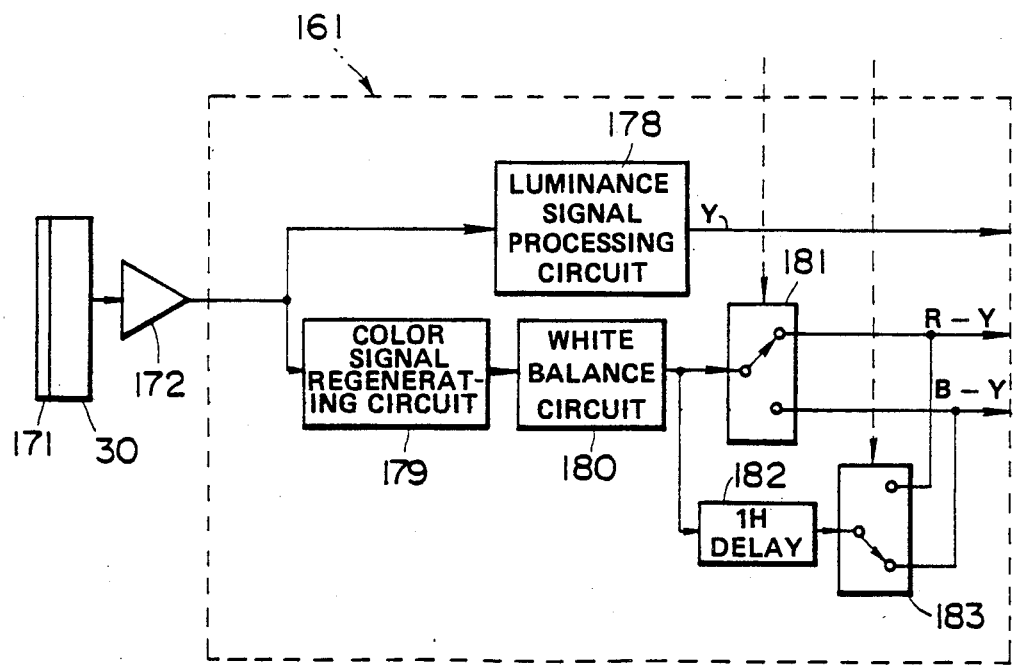

The above mentioned processing circuit 161 is formed as shown, for example, in FIG. 5.

That is to say, the output signal of the solid state imaging device 30 amplified by the pre-amplifier 172 is input into a luminance signal processing circuit 178 and a luminance signal Y is produced in this luminance signal processing circuit 178. Also, the output signal of the above mentioned solid state imaging device 30 is input into a color signal regenerating circuit 179 and color difference signals R-Y and B-Y are produced in time series in each horizontal line. These color difference signals R-Y and B-Y are compensated in white balance in a white balance circuit 180, are input directly into an analogue switch 181 on one hand and are delayed by one horizontal line by a 1H delaying line 182 and input into an analogue switch 183 on the other hand. The color difference signals R-Y and B-Y are obtained from the above mentioned analogue switches 181 and 183 switched by the switching signal of the timing generator 163.

The operation of this embodiment shall be explained in the following.

In using the endoscope apparatus 1 of this embodiment, the light source connector 120 provided at the tip of the connecting cable 113 is connected to the connector receptacle 116 of the light source apparatus 16 and the connector 106 provided at the tip of the signal cable 103 is connected to the connector receptacle 105 of the video processor 15. When the lamp 16a of the above mentioned light source apparatus 16 is lighted, the illuminating light emitted from this lamp 16a will be incident upon the entrance end of the light guide 45 through the rod lens 122 of the above mentioned light source connector 120. This illuminating light is led to the tip part 22 by the connecting cable 113, drum 3 and light guide 45 inserted through the insertable part 2, is emitted from the exit end of this light guide 45 and is radiated onto an object through the light distributing lens 44 and light distributing lens system 56. The returning light from the object by this illuminating light is made to form an image by the image forming optical system consisting of the lens system 54 and objective lens system 29 and is imaged by the solid state imaging device 30. The output signal of this solid state imaging device 30 is input into the above mentioned video processor 15 through the signal line 33, plug 83, receptacle 96, slip ring brushes 95, fixed rings 93, signal lines 99, signal correcting circuit 98, signal line 101, connector 106 and connector receptacle 105 and is processed to be a video signal. The video signal produced by this video processor 15 is input into the monitor 17 in which the observed image is displayed.

By rotating the drum 3, the insertable part 2 can be payed out or wound up and housed. When the above mentioned drum 3 is rotated, the parts extended out of the side of the drum 3 of the connecting cable 113 connected to the rotary shaft part 5 of this drum and the light guide 45 inserted through this connecting cable 113 will be also rotated. The above mentioned connecting cable 113 and light guide 45 are connected to the rotary mouthpiece 124 rotatable with respect to the light source apparatus 16 in the above mentioned light source connector 120. Therefore, the torque of the above mentioned drum 3 will be transmitted to the above mentioned rotary mouthpiece 24 by the above mentioned connecting cable 113 and this rotary mouthpiece will rotate following the rotation of the above mentioned drum 3. Therefore, the entrance end of the above mentioned light guide 45 will also rotate following the rotation of the above mentioned drum 3 and therefore this light guide 45 will not be twisted to be broken.

According to this embodiment, as the drum 3, light source apparatus 16 and video processor 15 are separately provided, each of the drum 3, light source apparatus 16 and video processor 15 will be small and light and the ability to carry and position it will be improved. Also, as the light source apparatus 16 and video processor 15 can be set in any place, the operability of the light source apparatus 16 and video processor will be improved.

If the form of the small diameter part 121a on the tip side of the light source connector 120 is made to conform to the standard of an existing light source apparatus, the existing light source will be also able to be utilized.

In the case of obtaining a color picture image, for example, by a field sequential system, such various light sources as a light source wherein the illuminating light is emitted as switched to red (R), green (G) or blue (B) and a light source wherein a light in another wavelength range than of a visible light is emitted can be utilized.

Further, according to this embodiment, as the light guide 45 can be led to the light source apparatus 16 without being cut off on the way and the light is conducted by the conducting elements, there will be no loss of the light amount conducted.

Also, in this embodiment, the connecting cable 113 through which the light guide 45 is inserted and the signal cable 103 through which the signal line 101 is inserted are led out of the end on the same side of the drum 3. Therefore, as compared with the case that the connecting cable 113 and signal cable 103 are led out respectively from both ends of the drum 3, the drum 3 housing space can be made smaller.

Further, the above mentioned connecting cable 113 and signal cable 103 are not in the way in carrying the drum 3 and the portability is improved.

In using the apparatus, as shown in FIG. 1, the light source apparatus 16 and video processor 15 can be arranged, for example, as overlapped on one side of the drum 3 and the operability is improved.

Figure 12:
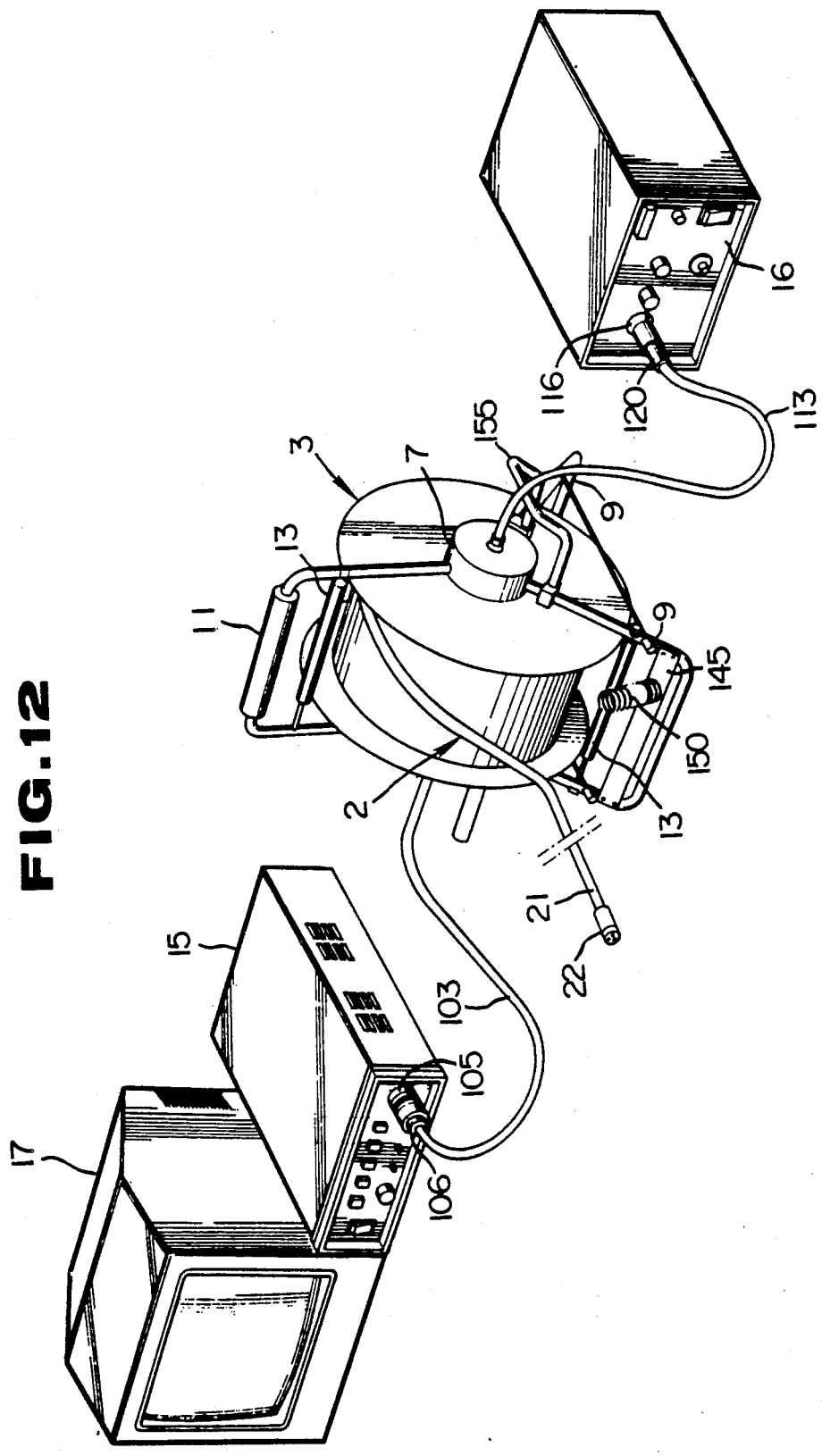
FIGS. 12 and 13 relate to the second embodiment of the present invention.
Figure 13:
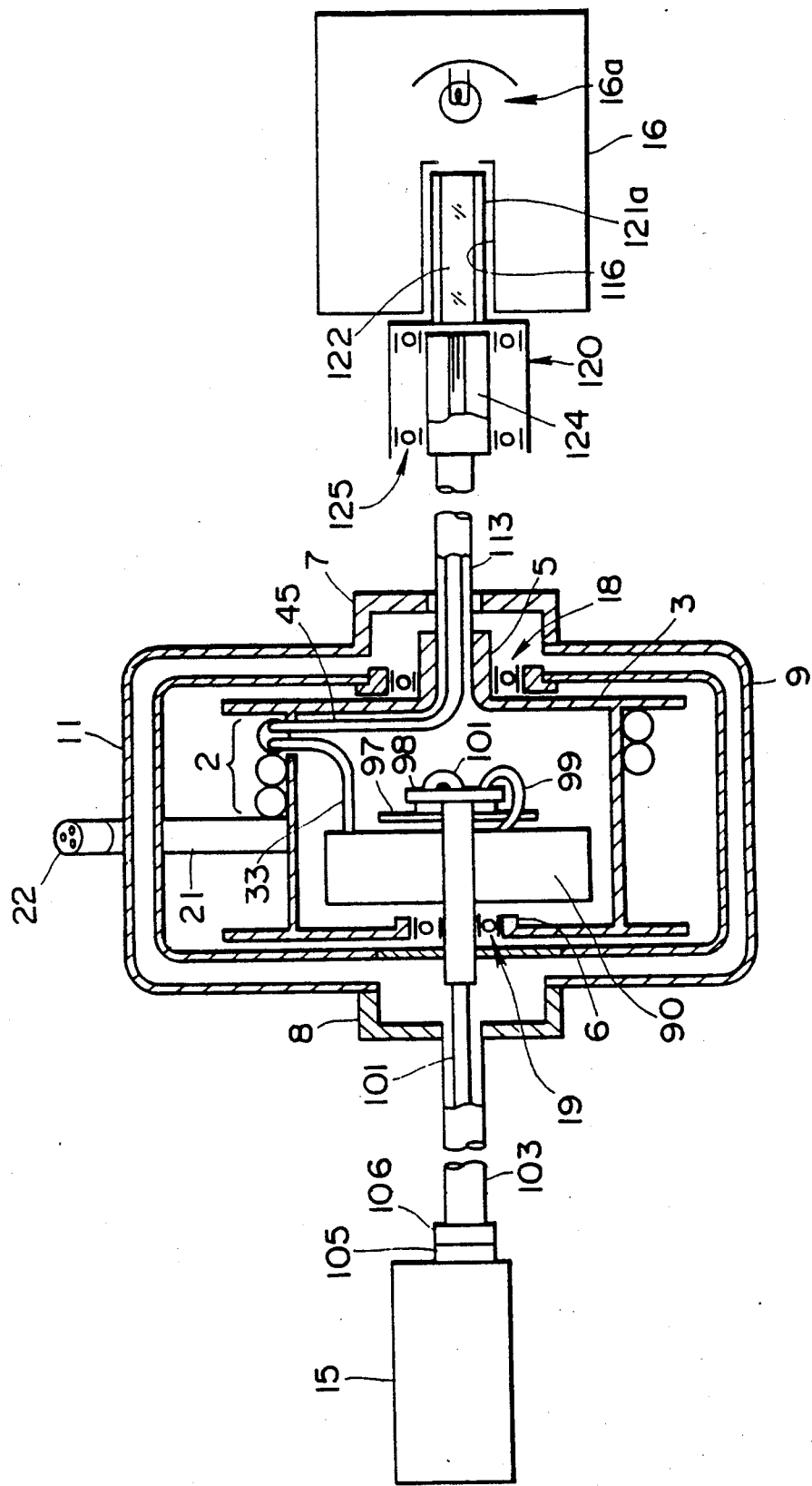

FIGS. 12 and 13 show the second embodiment of the present invention.

In this embodiment, as shown in FIG. 13, the signal line 101 connected to the signal correcting circuit 98 is inserted through the hollow part of the fixed shaft 91, is extended out of the side of the drum 3 and is led out of the bearing part 8 without passing through the handle 11.

Therefore, in this embodiment, the connecting cable 113 through which the light guide 445 is inserted and the signal cable 103 through which the signal line 101 is inserted are led respectively out of both ends of the drum 3.

The construction and operation of other elements are the same as in the first embodiment.

The effects of this embodiment are the same as of the first embodiment except the effect that the connecting cable 113 and signal cable 103 are led out of the end on the same side of the drum 3.

FIGS. 14 to 17 show the third embodiment of the present invention.

Figure 14:
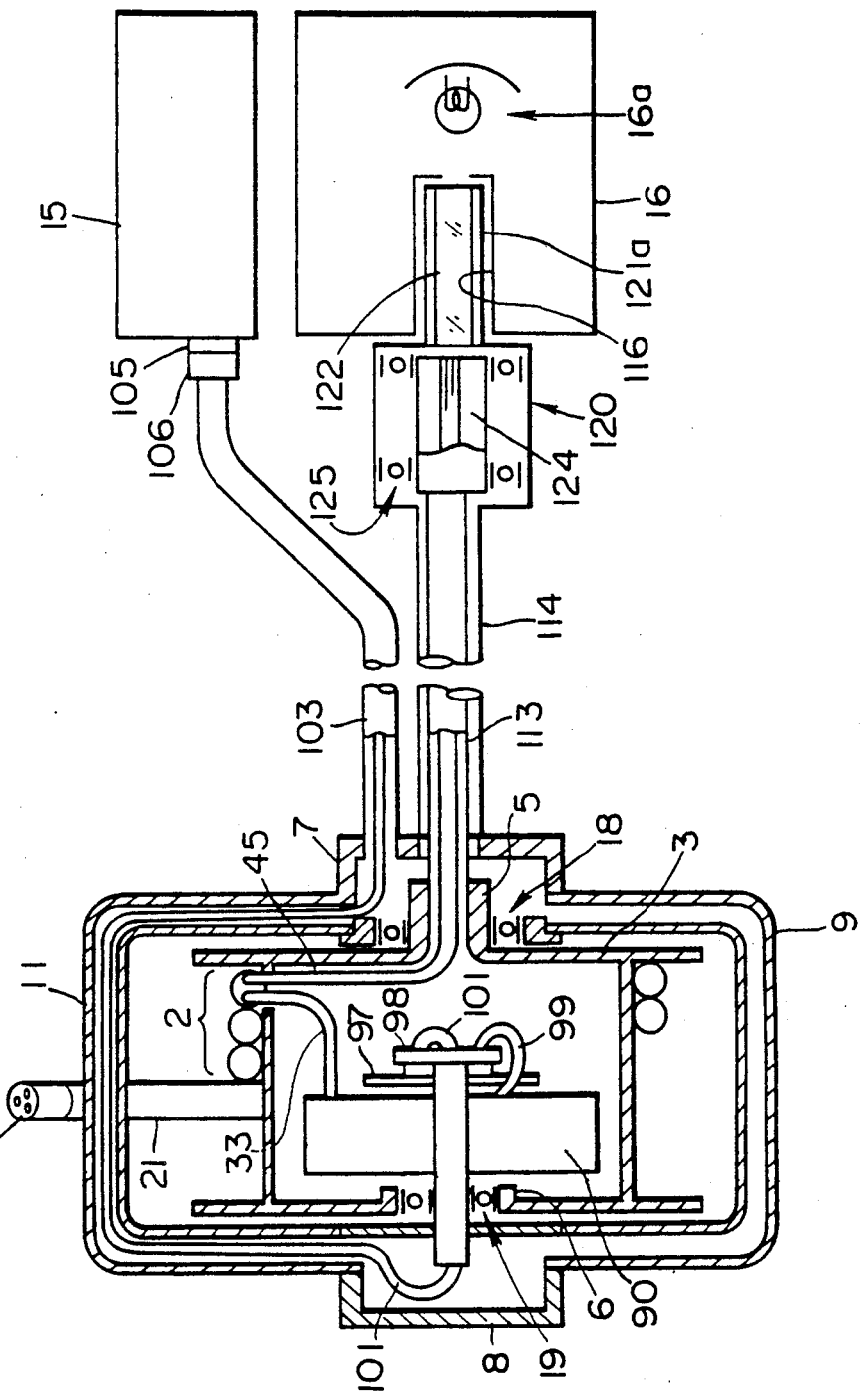
FIGS. 14 to 17 relate to the third embodiment of the present invention.
Figure 15:
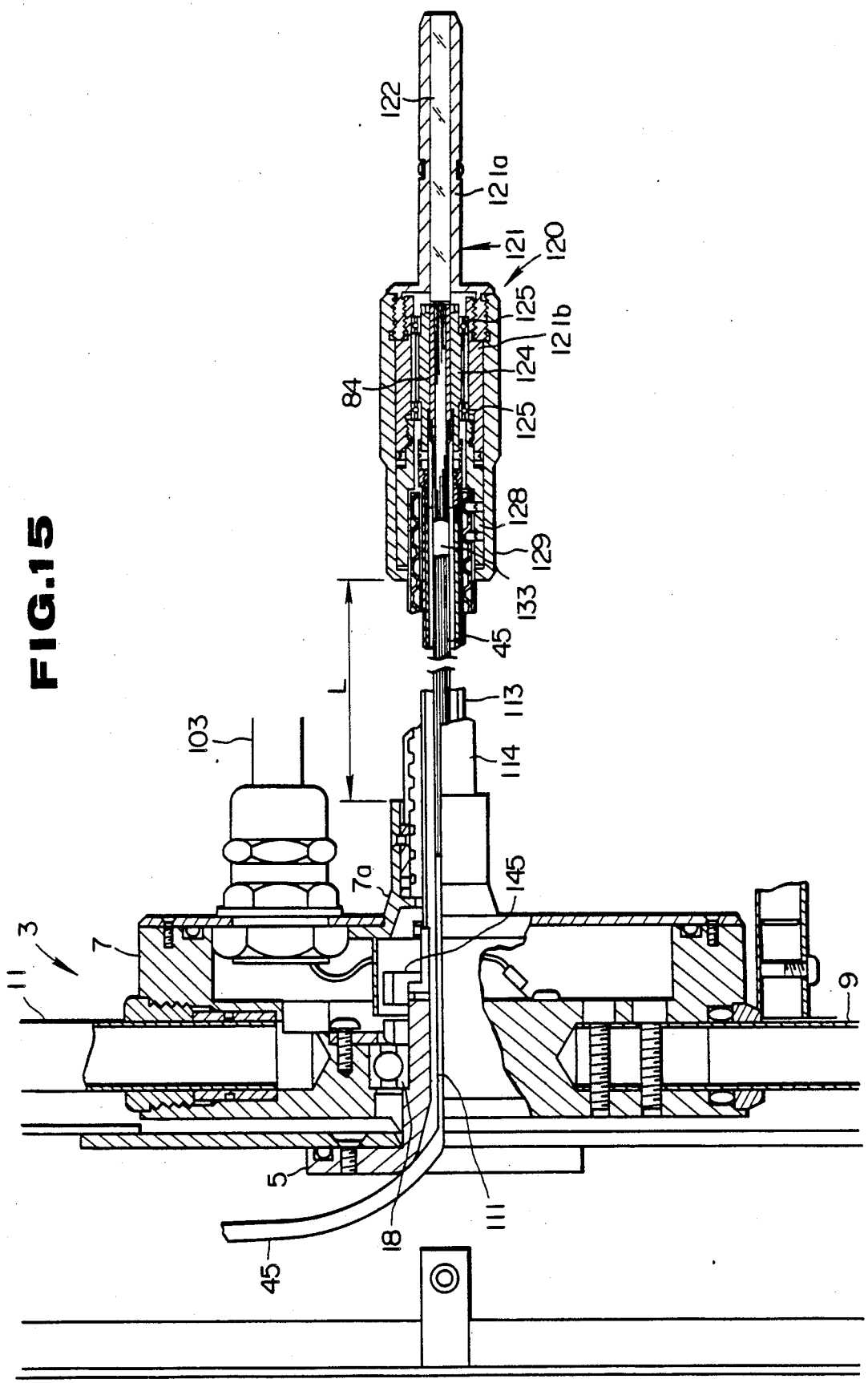

In this embodiment, as shown in FIGS. 14 and 15, the connecting cable 113 is covered on the outer periphery with a flexible hose 114. The above mentioned hose 114 is fixed and connected at one end to the tube body 128 of the light source connector 120, for example, with screws 130 as shown in FIG. 16 and at the other end to the housing 7a of the bearing part 7 fixed to the frame 9, for example, with screws as shown in FIG. 15 so as not to rotate even if the drum 3 rotates.

Figure 16:
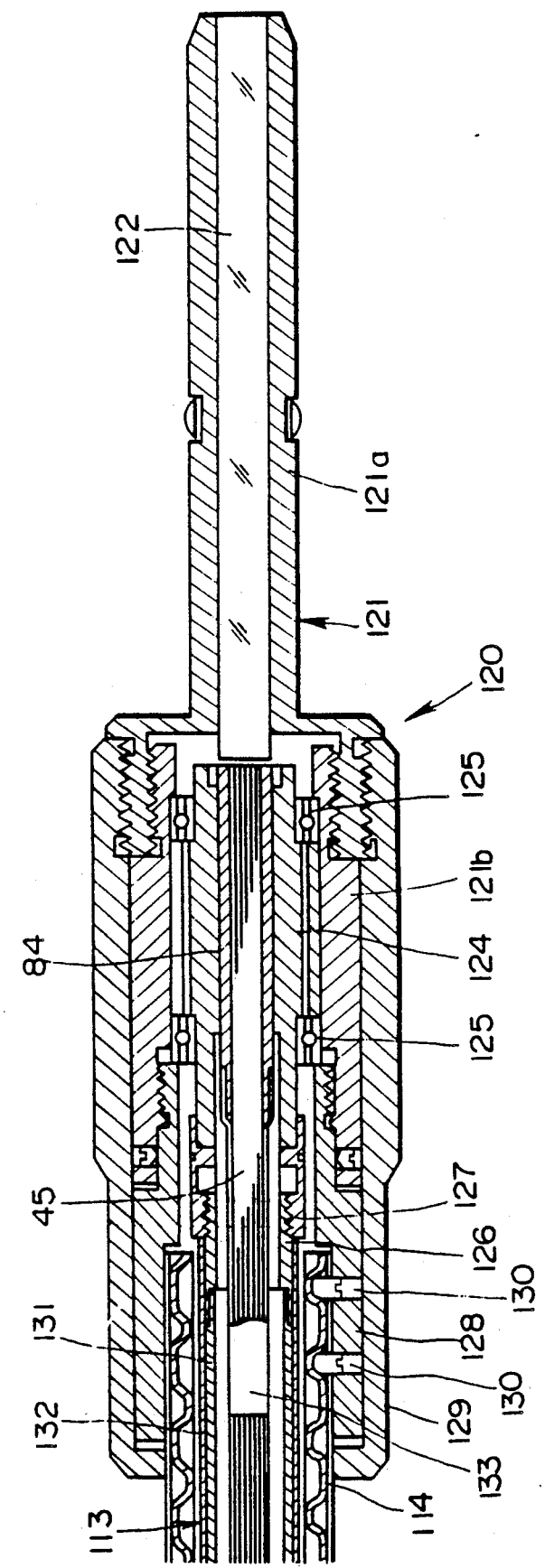

In this embodiment, as shown in FIG. 16, the above mentioned connecting cable 113 is formed of a urethane tube 131 and a net pipe 132 covering it on the outer periphery. The above mentioned light guide 45 is covered with such light guide fiber protecting tube as a silicone tube 133 on substantially all the parts but is not covered with such light guide fiber protecting tube as the above mentioned silicone tube 133 at least on a range in which the connecting cable 113 has a flexibility as shown by L in FIG. 15. Thus, as the light guide 45 is not covered with the protecting tube, even if the light guide 45 rotates while the connecting cable 113 is bent, the element lines of the internal light guide fibers will not be restricted in movement by the protecting tube. Therefore, the respective element lines will be freely displaced and will be kept so low in surface pressure when rubbed with each other as not to be damaged. Therefore, even if the light guide 45 rotates while bent, its life will be able to be kept long. The above mentioned light guide 45 is painted with such antifriction material as molybdenum.

Figure 17:
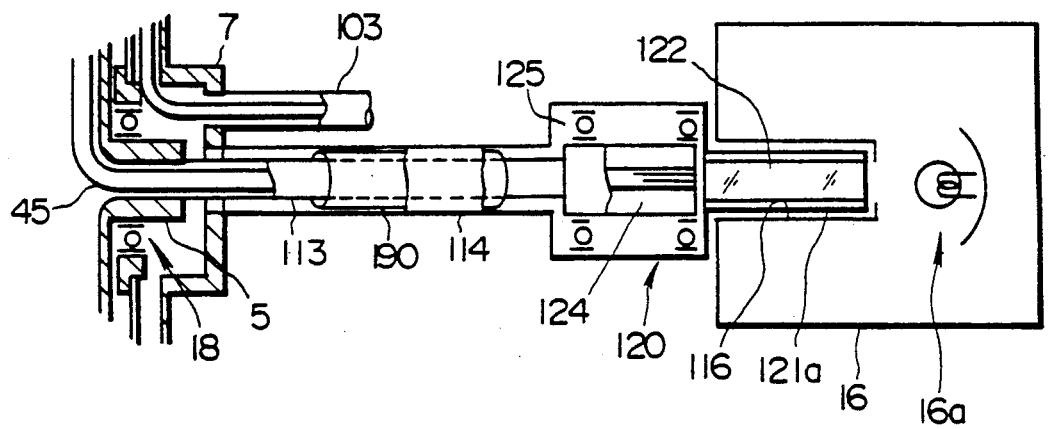

By the way, as shown in FIG. 17, a tube 190 for reducing friction may be interposed between the above mentioned hose 114 and connecting cable 113. Bearings or the like may be provided instead of this tube 190.

According to this embodiment, as the connecting cable 113 is not exposed out, the rotation will be smooth without being obstructed.

The construction, operation and effect of other elements of the apparatus are the same as in the first embodiment.

Figure 18:
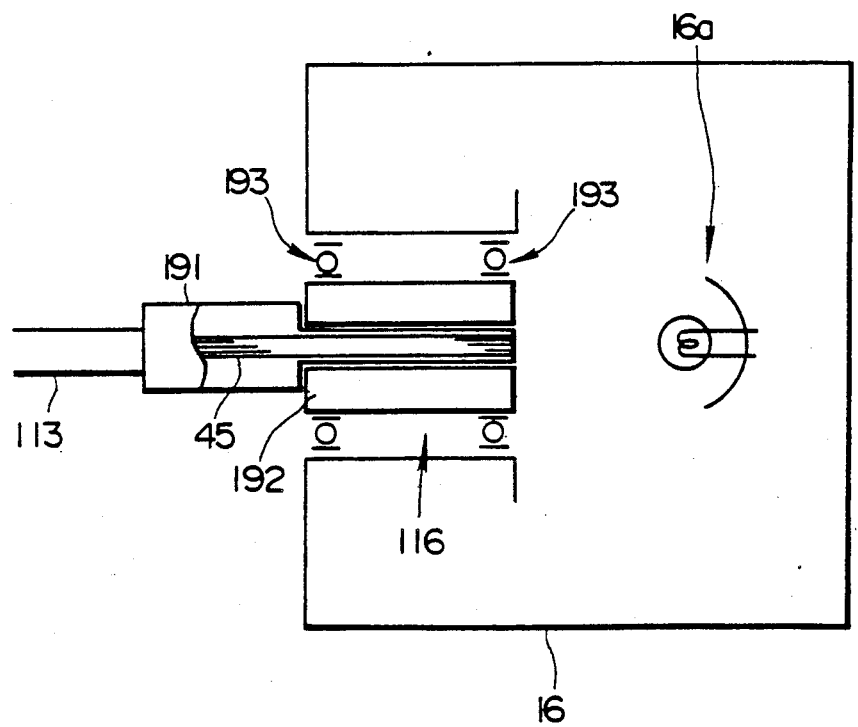
FIG. 18 is an explanatory view showing a light source apparatus and light source connector in the fourth embodiment of the present invention.

FIG. 18 shows the fourth embodiment of the present invention.

In this embodiment, the light guide 45 in the entrance end part and the connecting cable 113 in the end part are connected and fixed to a light source connector 191. On the other hand, the connector receptacle 116 of the light source apparatus 16 is provided with a connector receptacle body 192 supported rotatably with respect to the light source apparatus 16 through bearings 193. The above mentioned light source connector 191 can be inserted in and connected to the above mentioned connector receptacle body 192.

In this embodiment, the above mentioned connector 191 and connector receptacle body 192 rotate following the rotation of the drum 3.

The construction, operation and effect of other elements of the apparatus are the same as in the first embodiment.

Figure 19:
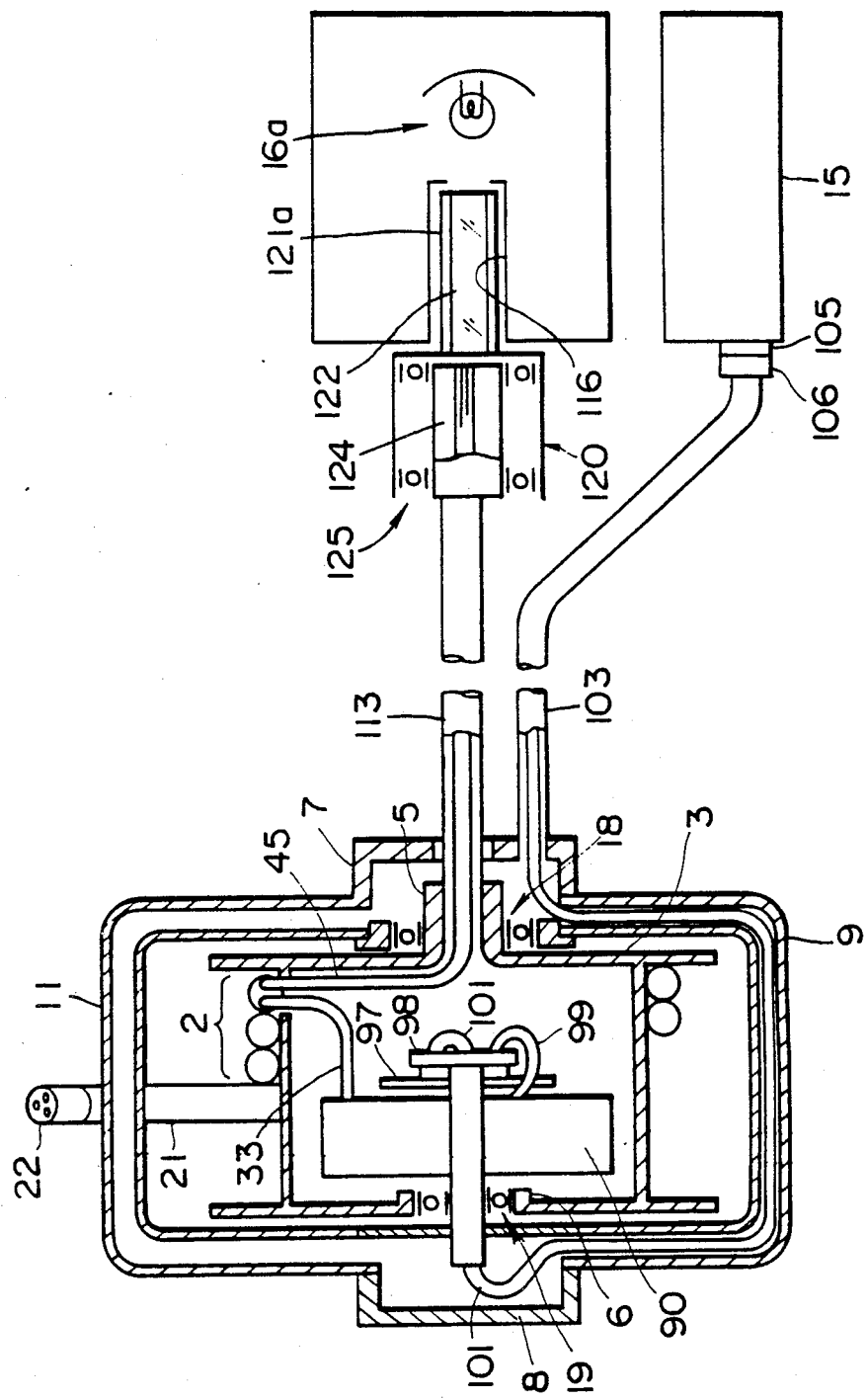
FIG. 19 is an explanatory view showing an endoscope apparatus of the fifth embodiment of the present invention.

FIG. 19 shows the fifth embodiment of the present invention.

In this embodiment, the signal line 101 is inserted through the frame 9 instead of the handle 11 and is led from the bearing part 8 on one side into the bearing part 7 on the other side.

The elements are the same as in the first embodiment.

Figure 20:
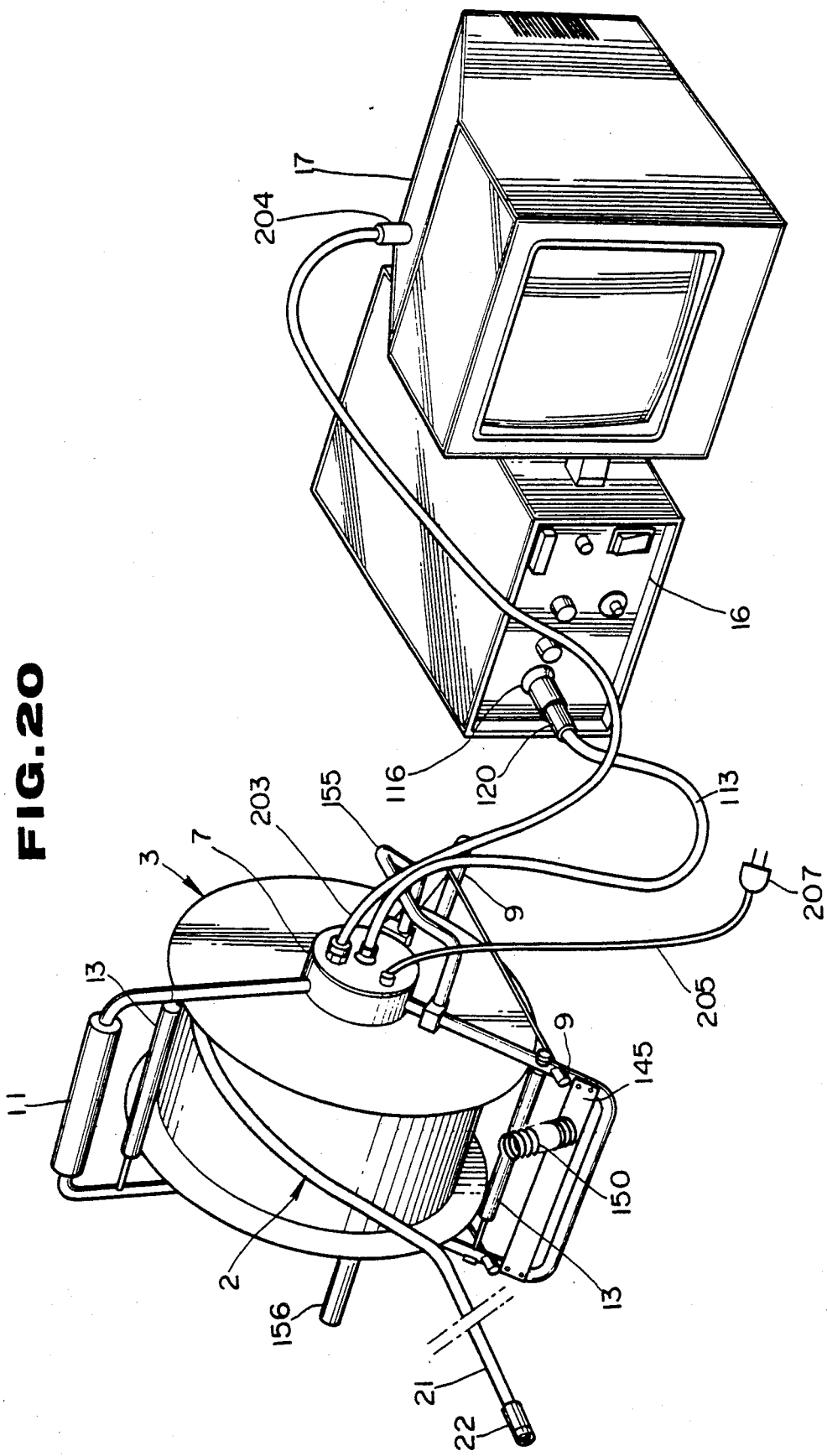
FIGS. 20 to 22 relate to the sixth embodiment of the present invention.
Figure 21:
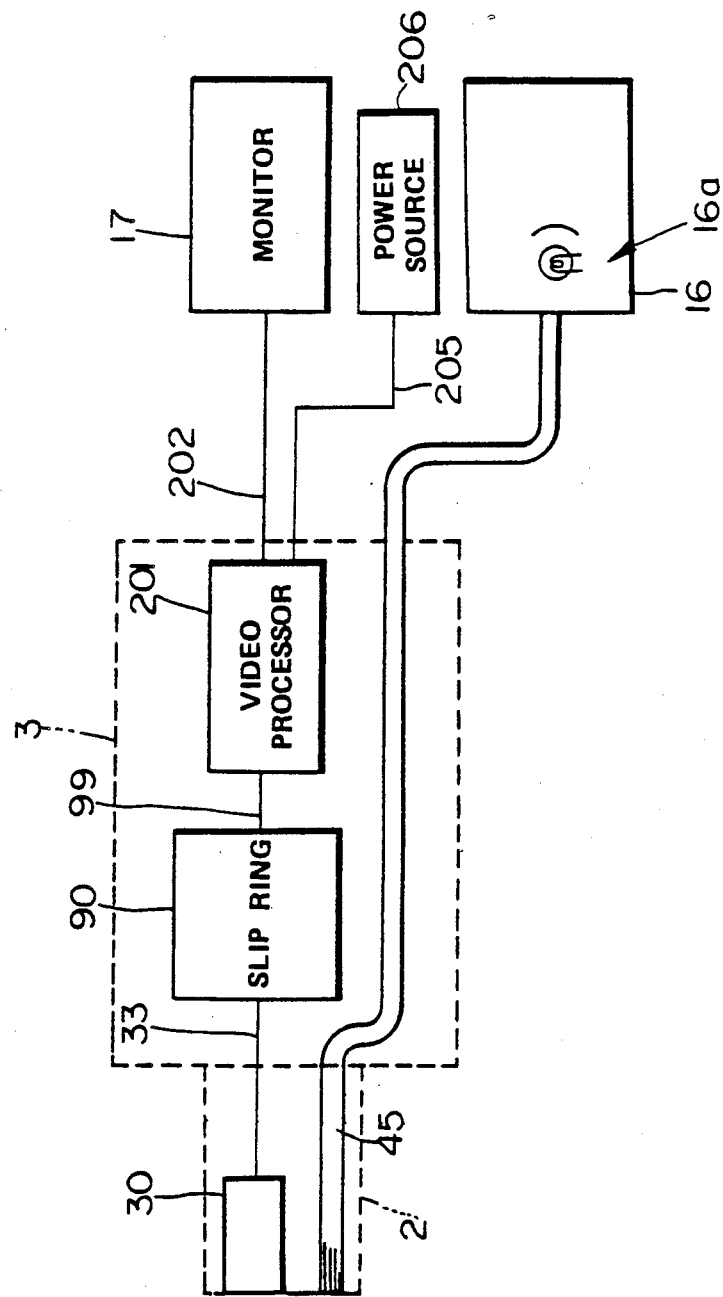
Figure 22:
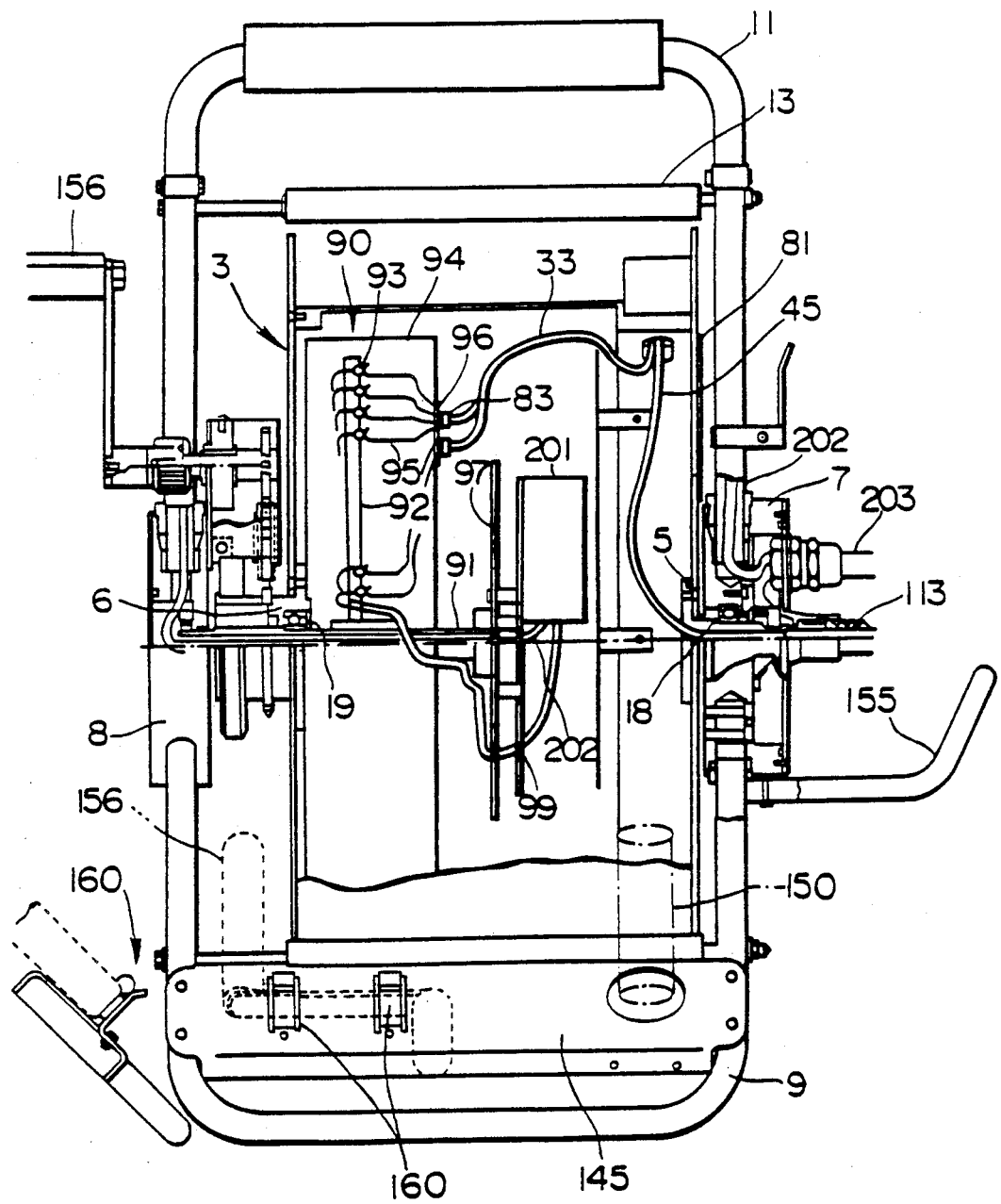

FIGS. 20 to 22 show the sixth embodiment of the present invention.

In this embodiment, a video processor 201 is provided within the drum 3.

As shown in FIG. 22, the above mentioned video processor 201 is fixed, for example to the terminal plate 97 fixed to the fixed shaft 91. The signal line 99 from the slip ring 90 is connected to this video processor 201. A signal line 202 led out of the above mentioned video processor 201 is inserted through the hollow part of the above mentioned fixed shaft 91, is led into the bearing part 7 on the other side through the handle 11 from the bearing part 8 on one side, is extended out of this bearing part 8 and is inserted through a video cable 203. This video cable 203 is provided in the end part with a connector 204 removably connectable to the monitor 17.

A current source cord 205 for feeding electric power to the above mentioned video processor 201 is extended out of the bearing part 7 of the above mentioned drum 3 and is provided in the end part with a plug 207 removably connectable to the current source 206.

By the way, the formation of the above mentioned video processor 201 is the same as of the video processor 15 shown, for example, in FIG. 4 and may include the signal correcting circuit 98.

In this embodiment, the output signal of the solid state imaging device 30 is processed to be a video signal by the above mentioned video processor 201, the video signal produced by this video processor 201 is input into the monitor 17 and an observed image is displayed in this monitor 17.

According to this embodiment, as the drum 3 and video processor 15 shown in the first to fifth embodiments are made integral, the portability of the endoscope system will improve.

By the way, in this embodiment, the electric positions of the slip ring 90 and video processor 201 may be replaced with each other. That is to say, the video processor 201 may be fixed to the drum 3 so as to rotate together with the drum 3, the signal line 33 may be connected to the video processor 201, the signal line from this video processor 201 may be connected to the slip ring 90 and the signal line from this slip ring 90 may be inserted through the video cable 203. Thus, the number of poles of the slip ring 90 can be decreased and generally the output signals of the video processor 201 are far less than the input signals.

By the way, the connecting cable 113 may be or need not be covered with the hose 114.

The elements are otherwise the same as of the first embodiment.

Figure 23:
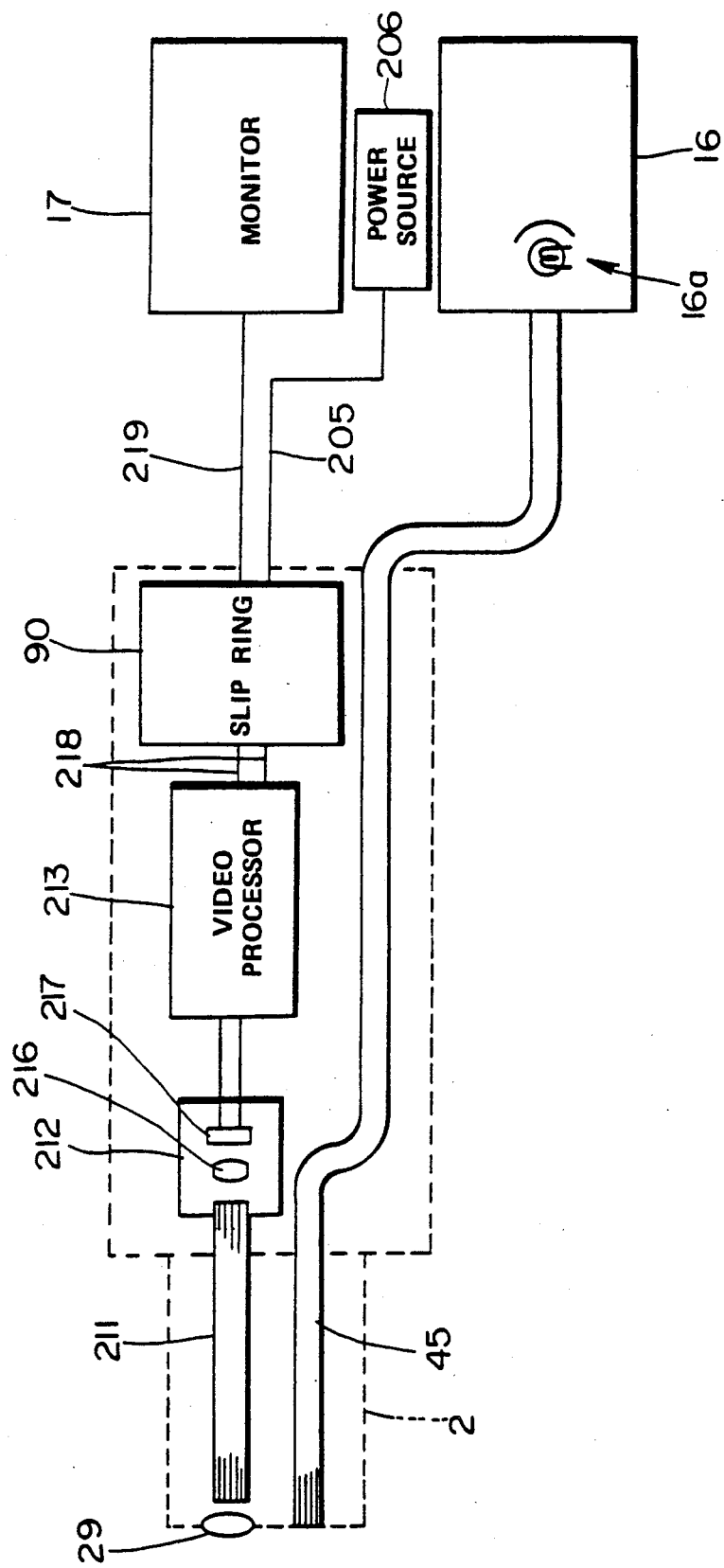
FIGS. 23 to 25 relate to the seventh embodiment of the present invention.
Figure 24:
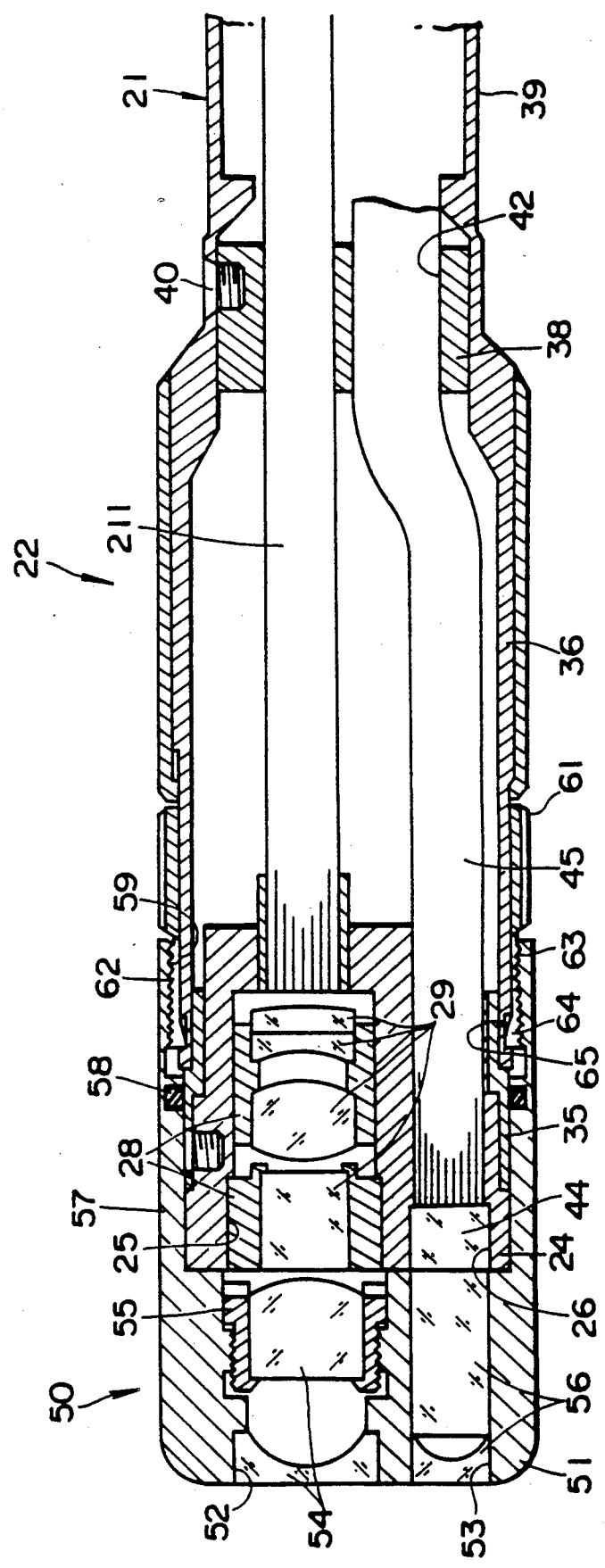
Figure 25:
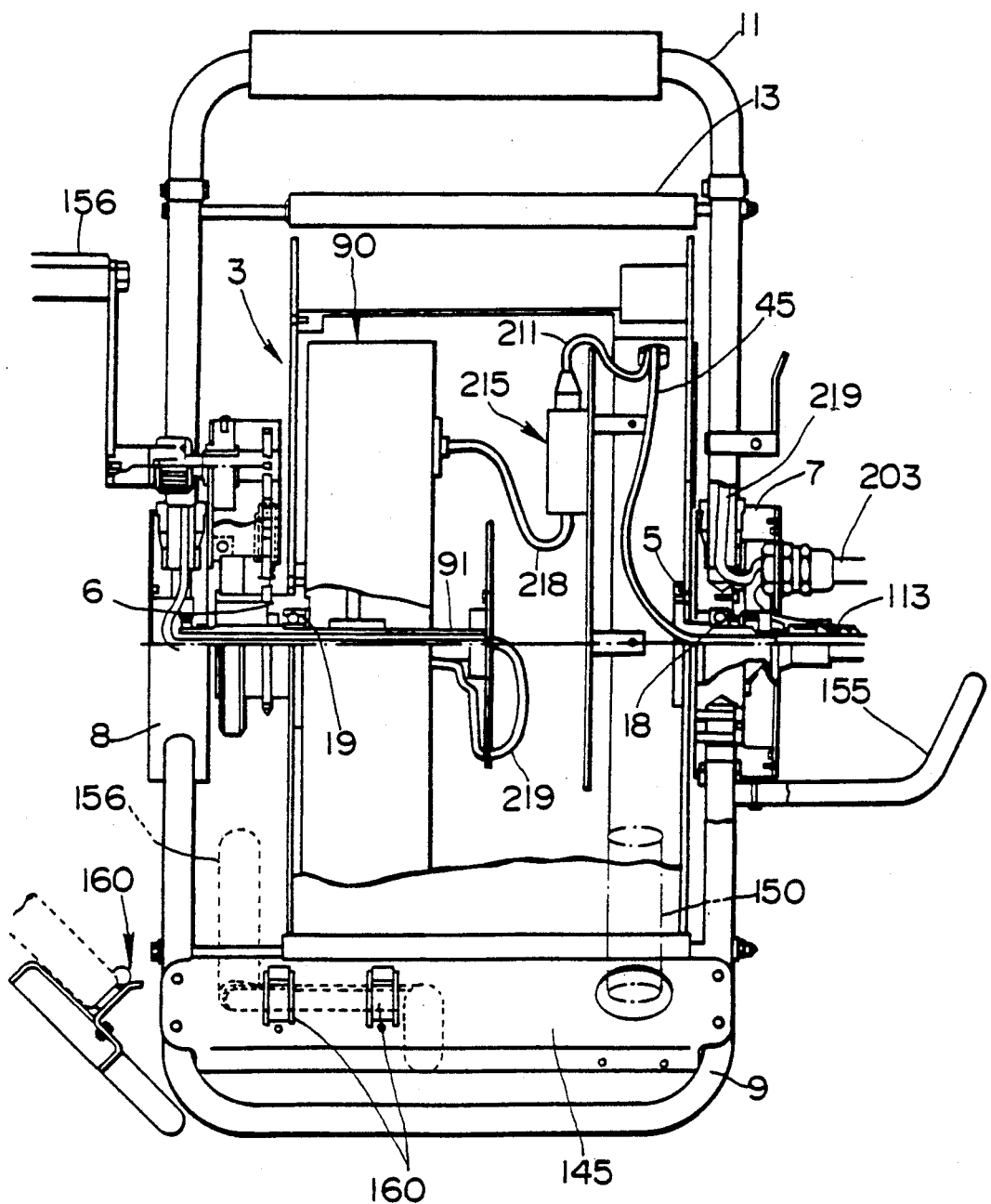

FIGS. 23 to 25 show the seventh embodiment of the present invention.

In this embodiment, as shown in FIG. 24, instead of the solid state imaging device 30, an image guide 211 of optical fibers is inserted through the insertable part 2, is arranged to have its tip surface in the image forming position of the objective lens system 29 and is led on the base end into the drum 3 as shown in FIG. 25. An imaging apparatus 215 in which a television camera 212 and video processor 213 fixed to the drum 3 are made integral so as to rotate together with this drum 3 is provided within this drum 3. The above mentioned image guide 211 is connected at its base end to the above mentioned television camera 212 so that an observed image formed by the above mentioned objective lens system 29 and transmitted by the image guide 211 may be imaged by the above mentioned television camera 212 which is provided, for example, with an image forming lens 216 forming an image of the light emitted from the exit end of the above mentioned image guide 211 and a solid state imaging device 217 arranged in the image forming position of this image forming lens 216. The above mentioned solid state imaging device 217 is driven by the above mentioned video processor 213 and the output signal of the solid state imaging device 217 is processed to be a video signal by the video processor 213. The formation of the above mentioned video processor 213 is the same as of the video processor 15 shown, for example, in FIG. 4.

A signal line 218 led out of the above mentioned video processor 213 is connected to the slip ring 90 and a signal line 219 led out of this slip ring 90 is inserted through the hollow part of the fixed shaft 91, is led into the bearing part 7 on the other side through the handle 11 from the bearing part 8 on one side and is inserted through the video cable 203 extended out of this bearing part 7. The above mentioned signal line 219 is connected to the monitor 17 through the connector 204. By the way, the appearance of this embodiment is as shown in FIG. 20 the same as in the sixth embodiment.

In this embodiment, the observed image formed by the objective lens system 29 and transmitted by the image guide 211 is imaged by the television camera 212, is processed to be a video signal by the video processor 213 and is displayed in the monitor 17.

According to this embodiment, as the image guide 211 is used without being provided with the solid state image device 30 in the tip part 21 of the insertable part 21, as compared with the case of using the solid state imaging device 30, there is an effect that the environment-proofness of the tip part 22 is higher.

The elements are the same as in the sixth embodiment.

Figure 26:
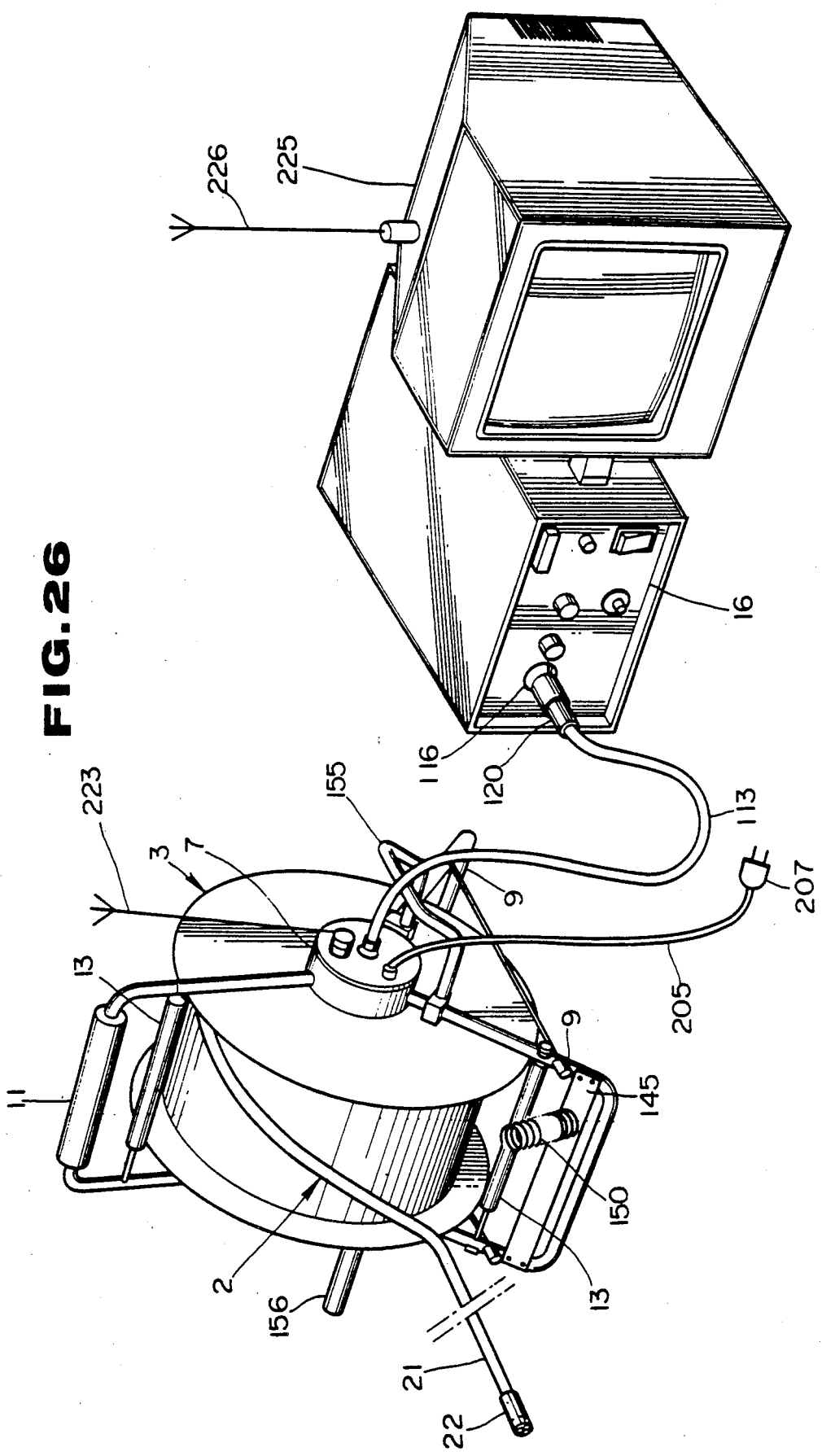
FIGS. 26 and 27 relate to the eighth embodiment of the present invention.
Figure 27:
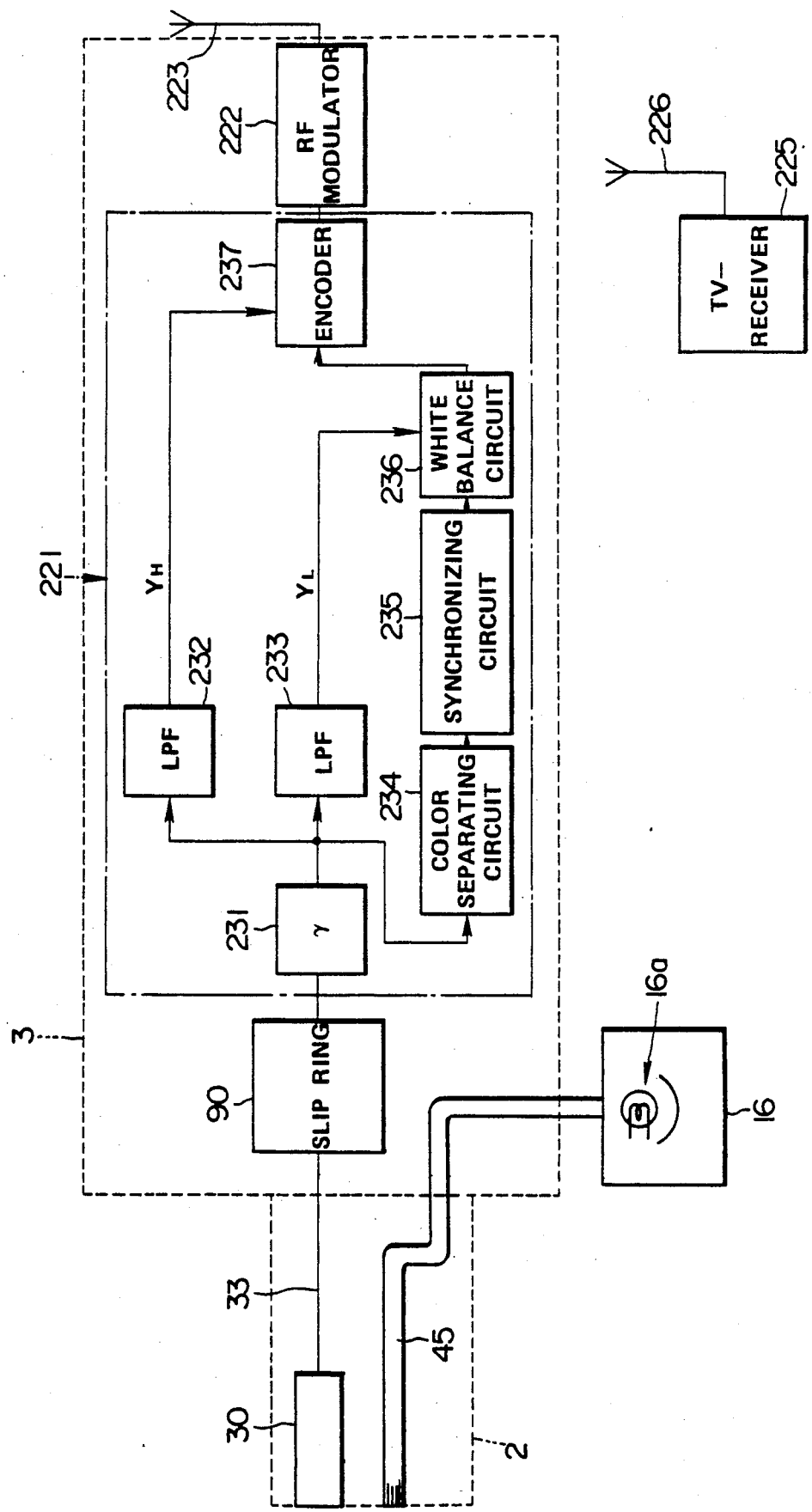
Figure 28:
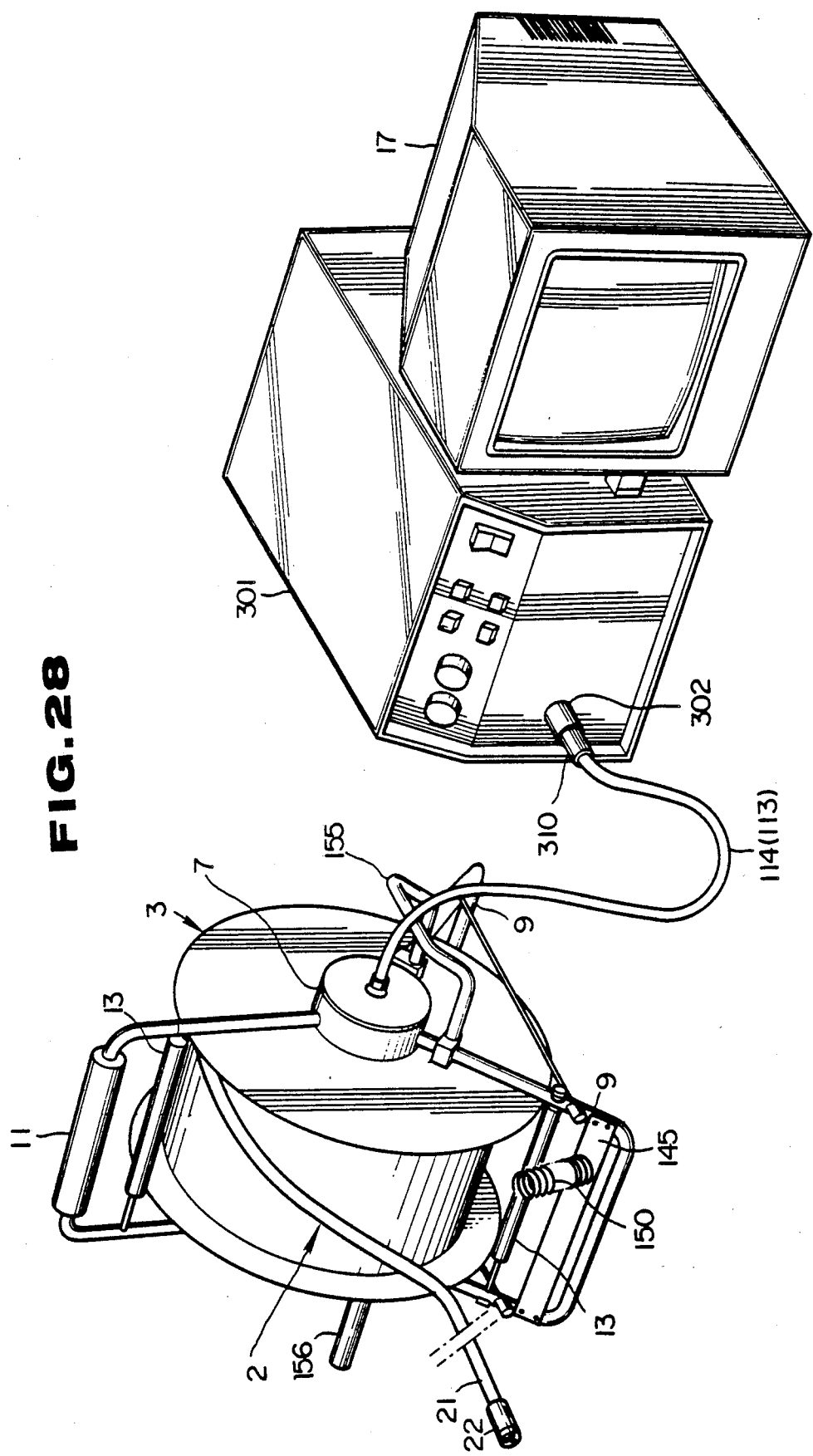
Figure 29:
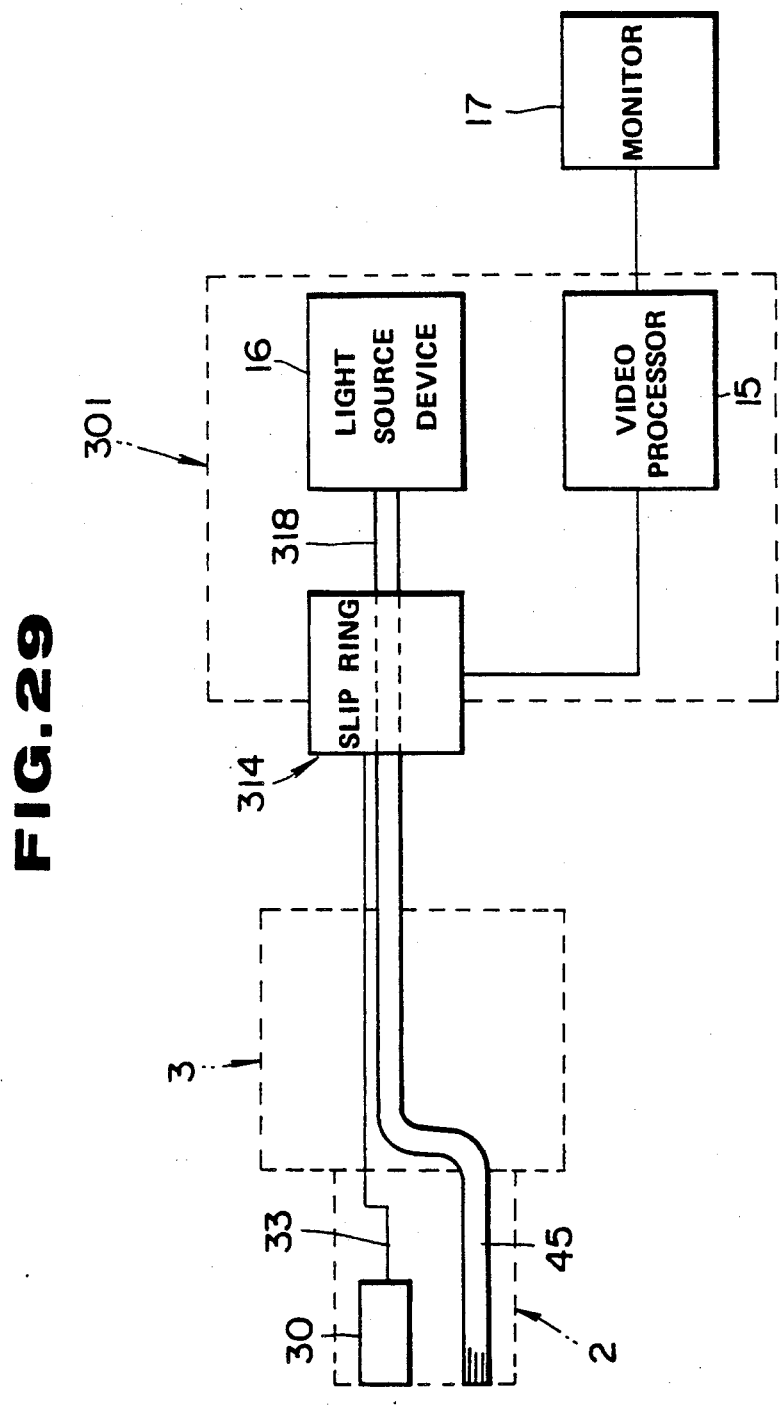

FIGS. 26 and 27 show the eighth embodiment of the present invention.

In this embodiment, the same as in the first to seventh embodiments, the light source apparatus 16 is provided separately from the drum 3 and the processing circuit 221 for processing the output signal of the solid state imaging device 30 so as to be a video signal is provided within the drum 3. By the way, in this embodiment, a synchronous system is used for the color imaging system. A color filter array in which color filters transmitting respectively red (R), green (G) and blue (B) colored lights are arranged in the form of a mosaic or the like is provided in front of the above mentioned solid state imaging device.

As shown in FIG. 27, the output signal of the above mentioned solid state imaging device 30 is input into the above mentioned processing circuit 221 through the signal line 33 and the slip ring 90 within the drum 3. A video signal is produced by this processing circuit 221, is converted to such high frequency wave as in the VHF band by an RF modulator 222 provided within the drum 3 and is emitted as an electric wave from an antenna 223 fitted to the drum 3 as shown in FIG. 26. This electric wave is received by an antenna 226, for example, of an ordinary television receiver 225 and is demodulated by this television receiver 225 and an observed image is displayed in this television receiver 225.

The above mentioned processing circuit 221 is formed as shown, for example, in FIG. 27.

That is to say, the output signal of the above mentioned solid state imaging device 30 is input into a $\gamma$-correcting circuit 231. The signal $\gamma$- corrected by this $\gamma$- correcting circuit 231 is input into a low-pass filter (LPF) 232 to obtain a luminance signal $Y_H$ of a side band, is input into a low-pass filter 233 to obtain a luminance signal $Y_L$ of a narrow band and is input into a color separating circuit 234 to separate a color difference signal component (or color signal component). The color difference signal (or color signal component) separated by the above mentioned color separating circuit 234 is converted to two color difference signals (or color signals) by a synchronizing circuit 235 and is adjusted in white balance in response to the level of the luminance signal $Y_L$ of the above mentioned narrow band by the white balance circuit. The luminance signal $Y_H$ of the above mentioned wide band and the color difference signal through the above mentioned white balance circuit 236 are input and mixed in an encoder 237 to produce a so-called composite video signal including such synchronous signal as, for example, of an NTSC system. This video signal is input into the above mentioned RF modulator 222.

Thus, in this embodiment, the video signal is transmitted and received by the electric wave between the endoscope apparatus provided with the drum 3 having the insertable part 2 having the solid state imaging device 30 and the processing circuit 221 and with the light source apparatus 16 separate from this drum 3 and the television receiver 225. Therefore, it is not necessary to wire the endoscope apparatus (drum 3) and television receiver 225 between them and the television receiver 225 can be freely arranged in any position.

Also, the television receiver 225 can be easily moved without pulling a long cable.

No cable between the endoscope apparatus (drum 3) and television receiver 225 is laid in the room or the like, is in the way in moving other devices and is likely to catch feet to break the cable and connector and to make the observation impossible.

Further, in housing and moving the endoscope apparatus, no long cable need be bundled and therefore such an operation is easy.

When an FM modulated wave is used to transmit and receive a video signal between the endoscope apparatus and television receiver 225, the external noise will hardly have an influence and the endoscope inspection will be improved in locations of high electronic interference such as within a factory.

By the way, as in the first embodiment, the video processor 15 may be provided separately from the drum 3 and signals may be transmitted and received between the drum 3 and video processor 15 or between the video processor 15 and monitor 17 by using electric waves. Also, as in the seventh embodiment, in imaging with the television camera 212, signals may be transmitted and received between the video processor 213 and monitor 17 by using electric waves.

The other elements are the same as in the first embodiment.

FIGS. 28 to 32 show the ninth embodiment of the present invention.

In this embodiment, a video analyzer 301 containing the light source apparatus 16 and video processor 15 is provided separately from the drum 3.

Figure 30:
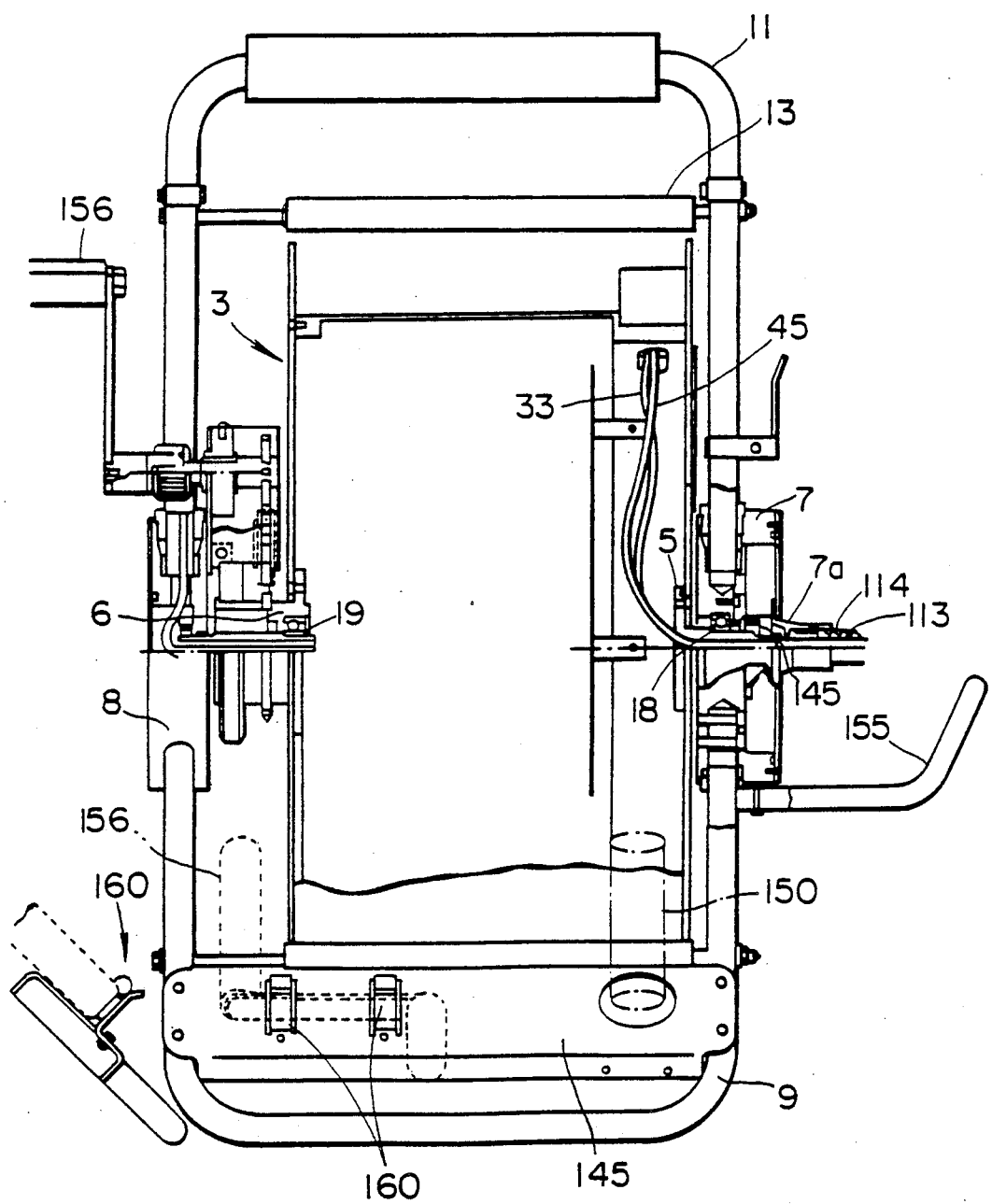

As shown in FIG. 30, the signal line 33 connected to the solid state imaging device 30 is led into the drum 3, is then inserted through the center hole 111 of the rotary shaft part 5 and is extended in the rotary shaft direction out of the above mentioned bearing part 7. The light guide 45 on the base end is led into the above mentioned drum 3, is then inserted through the center hole 111 of the above mentioned rotary shaft part 5 and is extended in the rotary shaft direction out of the above mentioned bearing part 7 together with the above mentioned signal line 33.

The above mentioned signal line 33 and light guide 45 in the parts extended out of the side of the above mentioned drum 3 are inserted through the flexible connecting cable 113. A light source connector 310 containing a slip ring and removably connectable to a connector receptacle 302 of the above mentioned video analyzer 301 is provided in the end parts of the above mentioned signal line 33, light guide 45 and connecting cable 113.

The above mentioned connecting cable 113 in the base end part is connected to the rotary shaft part 5 by a nut 145. Therefore, this connecting cable 113 rotates together with the rotation of the drum 3. The above mentioned connecting cable 113 is covered with the flexible hose 114 which is fixed and connected in the base end part to the housing 7a of the bearing part 7 fixed to the frame 9, for example, by screws. Therefore, even if the drum 3 rotates, this hose 114 will not rotate.

On the other hand, the above mentioned light source connector 310 is formed as shown in FIGS. 31 and 32.

That is to say, the light source connector 310 has a substantially tubular fixed member 311 and a substantially tubular rotary member 313 rotatably supporting through bearings 312 inside this fixed member 311. The above mentioned rotary member 313 has a small diameter part 313a at the tip. The light guide 45 is inserted in the entrance end part into this small diameter part 313a and is fixed, for example, by screws. When the light source connector 310 is inserted into the connector receptacle 302 of the video analyzer 301, the entrance end of the above mentioned light guide 45 will be opposed to the lamp 16a of the light source apparatus within the video analyzer 301 with the optical axes coinciding with each other.

The above mentioned rotary member 313 is provided on the outer periphery with a plurality (n) of rings 315 which form a slip ring assembly 314 and to which the above mentioned signal lines 33 are connected. The above mentioned fixed part 311 is provided with a plurality of terminals 316 corresponding to the above mentioned rings 315. Brushes 317 in contact with these terminals 316 are in electric contact with the above mentioned rings 315.

On the other hand, on the connector receptacle 302 side of the video analyzer 301, a plurality of contacts 318 corresponding to the above mentioned terminals 316 are provided to electrically contact the above mentioned terminals 316 and are connected to the video processor 15.

By the way, as shown in FIG. 32, the above mentioned fixed member 311 is provided on the outer periphery with a positioning pin 320 for positioning and rotation prevention to be engaged with a groove 321 in the connector receptacle 302.

The above mentioned connecting cable 113 is fixed to the above mentioned rotary member 313, for example, with a screw through the connecting ring 323. The above mentioned hose 114 is fixed to the above mentioned fixing member 311, for example, with screws.

Therefore, the signal line 33, light guide 45, connecting cable 113 and rotary member 313 will rotate together with the rotation of the drum 3 but the hose 114 and fixed member 311 will not rotate even if the drum 3 rotates.

The other elements of the apparatus are the same as in the first embodiment.

In this embodiment formed as in the above, when the light source connector 310 provided at the end of the connecting cable 113 is connected to the connector receptacle 302 of the video analyzer 301 and the lamp 16a of the light source apparatus 16 within this video analyzer 301 is lighted, the illuminating light from this lamp 16a will be incident upon the entrance end of the light guide 45. This illuminating light is led to the tip part 22 by the light guide 45 inserted through the connecting cable 113 and insertable part 2, is emitted from the exit end of the above mentioned light guide 45 and is radiated onto an object through the light distributing lens.

The returning light from the object by this illuminating light is made to form an image by the image forming optical system and is imaged by the solid state imaging device 30 which is connected to the video processor 15 within the video analyzer 301 through the signal line 33 and the slip ring 314 within the light source connector 310. The video signal from the above mentioned video processor 15 is input into the monitor 17 and an observed image is displayed in this monitor 17.

According to this embodiment, the drum 3 and video analyzer 301 can be connected with each other through one connecting cable 113 and the operability of the system is improved.

The other operations and effects are the same as in the first embodiment.

FIGS. 33 to 37 show the tenth embodiment of the present invention.

This embodiment is substantially the same as the ninth embodiment but the color imaging system is replaced with a synchronous system of a field sequential type.

Figure 33:
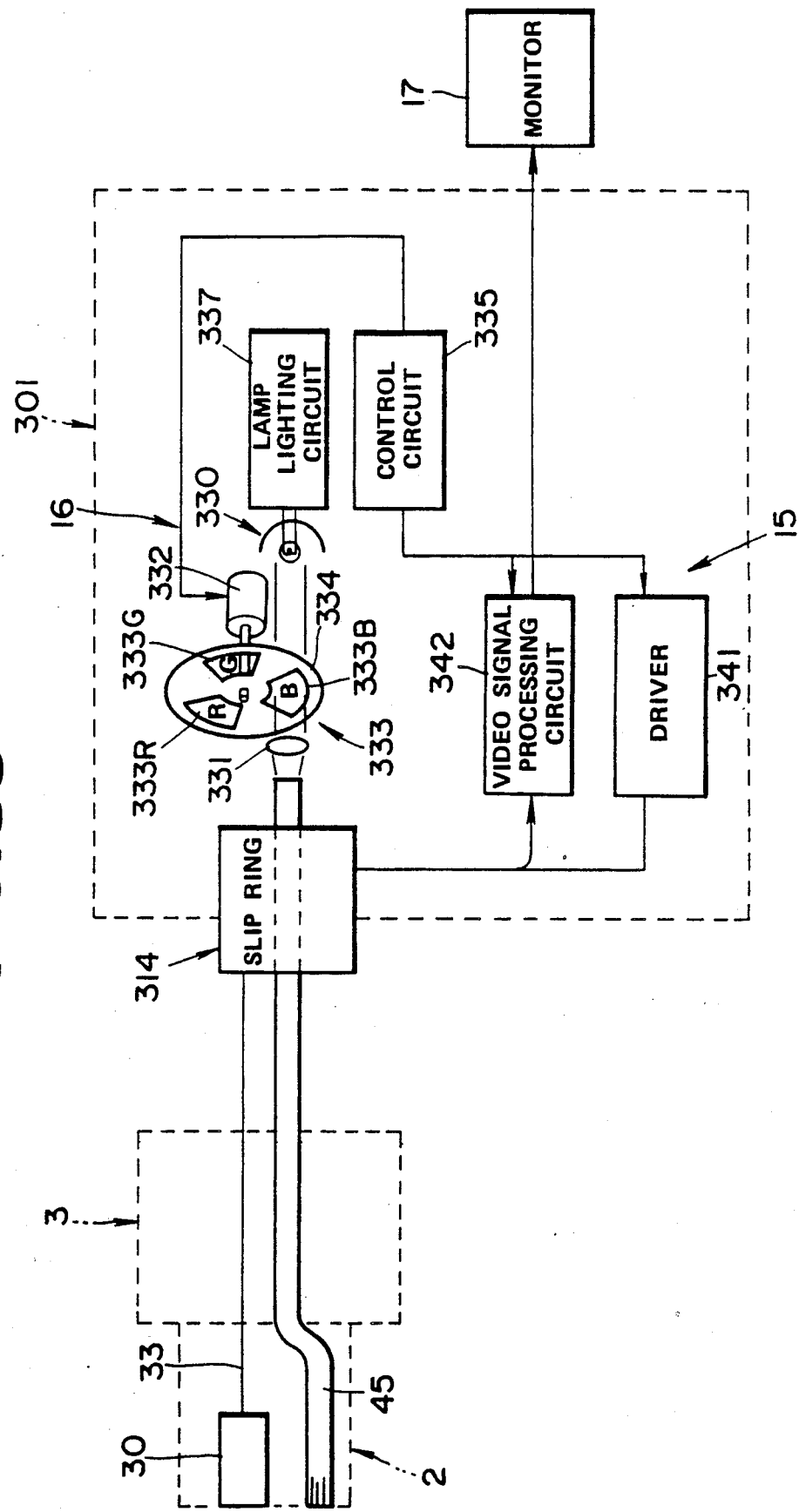
FIGS. 33 to 37 relate to the tenth embodiment of the present invention.
Figure 35:
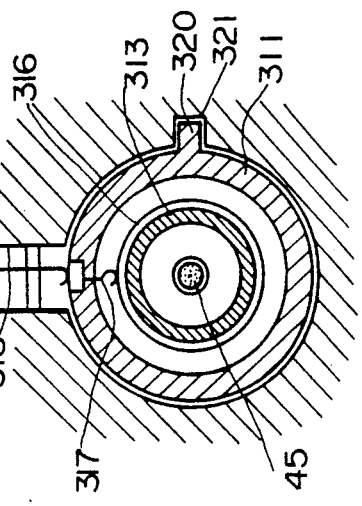
Figure 34:
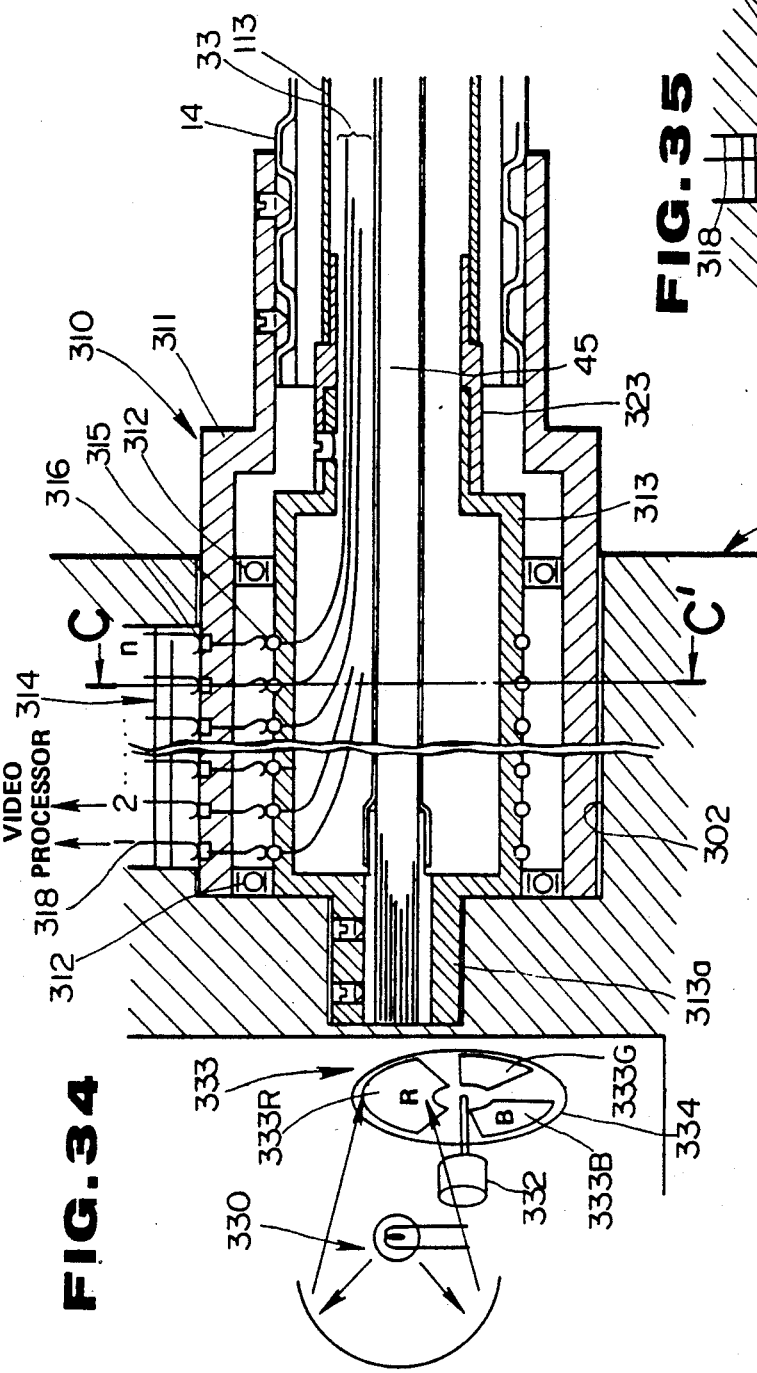

As shown in FIGS. 33 and 34, the light source apparatus 16 within the video analyzer 301 has a lamp 330 driven by a lamp lighting circuit 337 to emit a white light and a condenser lens 331 for condensing the light emitted from this lamp 330 and making the condensed light incident upon the entrance end of the light guide 45. A rotary filter 333 rotated and driven by a motor 332 is arranged on the illuminating light path between the above mentioned lamp 330 and condenser lens 331. In this rotary filter 333, three fan-like apertures are provided in the peripheral direction on a disc-like rotary plate 334 and a red transmitting filter 333R, green transmitting filter 333G and blue transmitting filter 333B are fitted to the respective apertures. The above mentioned motor 332 is controlled in rotation by a control circuit 335 provided within the video analyzer 301. The light emitted from the above mentioned lamp 330 is transmitted through the above mentioned rotary filter 333 and is separated into a time series of lights in the respective wavelength ranges of red, green and blue. These lights are incident upon the entrance end of the light guide 45 and these field sequential illuminating lights are radiated onto an object.

The video processor 15 within the video analyzer 301 has a driver 341 driving the solid state imaging device 30 and a video signal processing circuit 342 for processing the output signal of the above mentioned solid state imaging device so as to be a video signal, which are connected to the above mentioned solid state imaging device 30 through the signal line 33 and slip ring 314 within the light source connector 310. The output signal of the solid state imaging device 30 driven and read out by the above mentioned driver 341 is processed by the above mentioned video signal processing circuit 342 and the video signal produced by this video signal processing circuit 342 is input into the monitor 17 to color-display an observed image. By the way, the above mentioned driver 341 and video signal processing circuit 342 are controlled in time and the like by the above mentioned control circuit 335.

Figure 36:
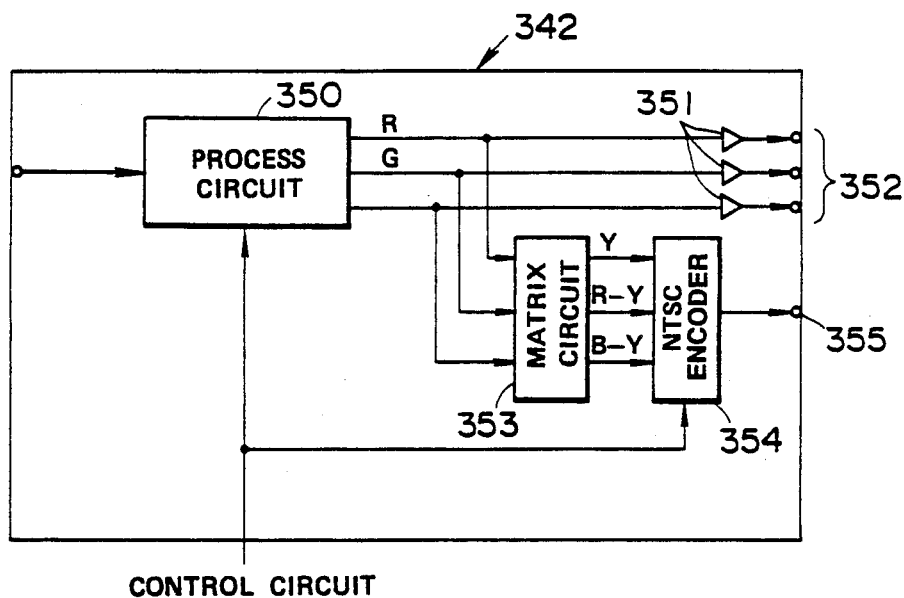

The above mentioned video signal processing circuit 342 is formed as shown, for example, in FIG. 36.

That is to say, the above mentioned video signal processing circuit 342 is provided with a processing circuit 350 for processing the output signal of the solid state imaging device 30 so as to be a video signal. The output signal of the above mentioned solid state imaging device 30 is amplified by a pre-amplifier 349 and is then input into the above mentioned processing circuit 350 and signals imaged respectively under field sequential lights, for example, of R, G and B are output as color signals R, G and B. The above mentioned respective color signals R, G and B are output as three primary color signals RGB respectively from three primary color output terminals 352 through drivers 351. Also, the above mentioned color signals R, G and B are transmitted through a matrix circuit 353 to produce a luminance signal Y and color difference signals R-Y and B-Y which are then input into an NTSC encoder 354 and are converted to a composite video signal of an NTSC system to be output from an NTSC output terminal 355. By the way, the above mentioned processing circuit 350 and NTSC encoder 353 are controlled in timing by the above mentioned control circuit 335.

Figure 37:
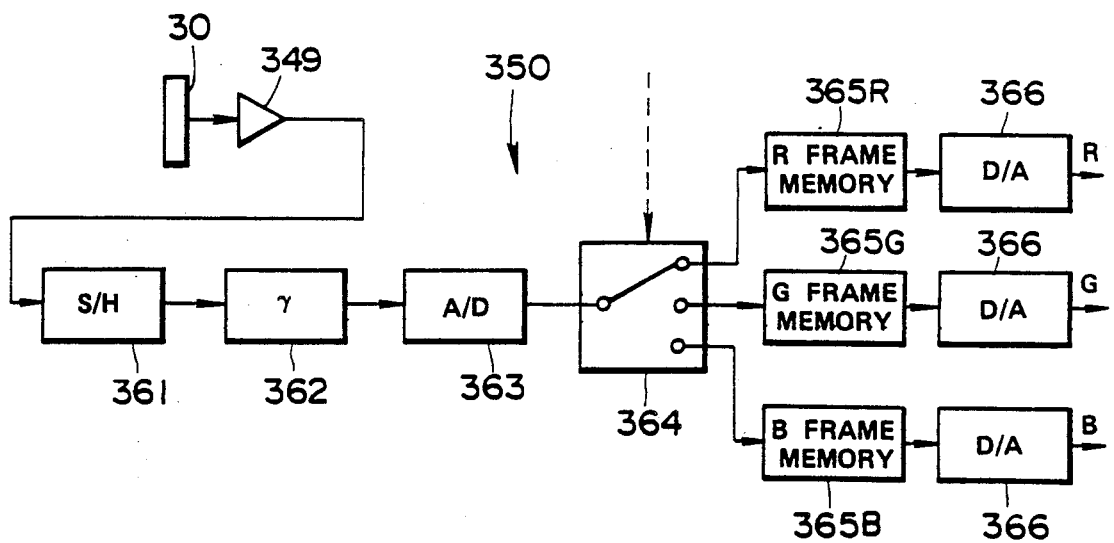

The above mentioned processing circuit 350 is formed as shown, for example, in FIG. 37.

That is to say, the output signal of the solid state imaging device 30 input through the pre-amplifier 349 is sample-held by the sample holding circuit 361, is then $\gamma$-corrected by the $\gamma$- correcting circuit 362 and is converted to a digital signal by an A/D converter 363. Through a multiplexer 364 switched by the signal of the above mentioned control circuit 335, the signals imaged under the field sequential lights of R, G and B are written respectively into an R frame memory 365R, G frame memory 365G and B frame memory 365B. These respective frame memories 365R, 365G and 365B are simultaneously read out, are converted respectively to analogue color signals R, G and B by D/A converters 366 and are output.

According to this embodiment, the size of the field sequential type solid state imaging device 30 to obtain the same resolution as in the synchronous type may be smaller (fewer pixels) than the size of the synchronous type solid state imaging device and the tip part 22 of the insertable part 2 can be made smaller.

The other elements of this embodiment are the same as in the ninth embodiment.

FIGS. 38 to 40 show the eleventh embodiment of the present invention.

In this embodiment, the same as in the seventh embodiment, the image guide 211 is inserted through the insertable part 2. A hollow rotary shaft part 372 supported rotatably by the bearing part 8 through a bearing 371 and rotating together with the rotation of the drum 3 is provided in one end part of the drum 3 and the above mentioned image guide 211 in the base end part is led into the drum 3 and is inserted in and fixed to the above mentioned rotary shaft part 372. An eyepiece 374 is fitted to the outside end of the hollow part of the above mentioned rotary shaft part 372 as opposed to the end surface of the above mentioned image guide 211 so that a naked eye observation may be made through this eyepiece 374.

A connecting part 375 fittable with an imaging apparatus 380 or the like is provided in the center of the side of the above mentioned bearing part 81. In this imaging apparatus 380, for example, as in the imaging apparatus 215 of the seventh embodiment, the television camera 212 and video processor 213 are made integral so that an observed image from the above mentioned eyepiece 374 may be provided. The video signal output from this imaging apparatus 380 is input into the monitor 17 to display the observed image.

The above mentioned connecting part 375 can be fitted with not only the above mentioned imaging apparatus 380 but also such still camera 382 as is shown in FIG. 39 and such viewing apparatus (also called a lecturescope) as is shown in FIG. 40. The above mentioned still camera 382 is provided with an image forming lens 383 forming the image of the light from the above mentioned eyepiece 374 and a film arranged in the image forming position of this image forming lens. The above mentioned viewing apparatus 390 is provided, for example, with a first eyepiece part 394 having a lens 391 for condensing the light from the above mentioned eyepiece 374, such light beam dividing means for dividing into two the light having passed through this lens 391 as, for example, a half-silvered mirror 392 and a first eyepiece 393 provided on the light path divided by this half-silvered mirror 392 and a second eyepiece part 399 having an image forming lens 396 and a second eyepiece 398 connected and provided through an image guide 397 on the other light path divided by the above mentioned half-silvered mirror 392 so that a naked eye observation may be simultaneously made with the first eyepiece part 394 and second eyepiece part 399. The above mentioned imaging apparatus 380 or still camera 382 may be connected to the first eyepiece part 394 or second eyepiece part 399 of the above mentioned viewing apparatus 390.

By the way, in this embodiment, the above mentioned light guide 211 in the base end part may be extended out of the side of the drum 3 to provide an eyepiece part or a connecting part connectable with a television camera or the like may be provided.

The other elements are the same as in the seventh embodiment.

FIG. 41 shows the twelfth embodiment of the present invention.

In this embodiment, the light guide 45, for example, in the first embodiment is divided on the side of the drum 3 so that the part extended out of the side of the drum 3 may not rotate.

A mouthpiece 401 is fitted to the base end part of the light guide 45, is inserted into the center hole 111 of the rotary shaft part 5 and is fixed to the shaft part 5 with a screw 402. A light guide 410 is connected coaxially opposite the end surface of the above mentioned light guide 45. A mouthpiece 411 is fitted to the end part of the light guide 410 on the side opposed to the above mentioned light guide 45 and is fixed with a screw 412 to a light guide fixing piece 415 fixed to the bearing part 7. Therefore, the light guide 45 rotates together with the drum 3 but, even if the drum 3 rotates, the light guide 410 will not rotate.

On the other hand, a light source connector 420 is provided in the other end part of the above mentioned light guide 410 and is provided with a substantially cylindrical connector body 421 consisting of a small diameter part 421 on the tip and a large diameter part 421b on the base end. A rod lens 422 is contained and fixed in the tip of the above mentioned small diameter part 421a. A mouthpiece 424 is fitted to the end part of the above mentioned light guide 410. The light guide 410 at this end part is inserted through the above mentioned small diameter part 421a so as to be opposed to the rear end surface of the above mentioned rod lens 422 and is fixed with a screw 425. The above mentioned light guide 410 is covered with the flexible hose 114 which is fixed in the respective end parts to the connector body 421 and light guide fixing piece 415 with screws 431 and 432.

The other elements are the same as in the first embodiment.

In this embodiment, the light emitted from the lamp 16a of the light source apparatus 16 is incident upon the light 410 through the rod lens 422, is emitted from the end part on the mouthpiece 411 of this light guide 410, is incident upon the end surface on the mouthpiece 401 of the light guide 45 opposed to the above mentioned light guide 45, is led to the tip part 22 by this light guide 45 and is radiated as an illuminating light onto an object.

According to this embodiment, as such rotary light guide as is shown in the first to eleventh embodiments is not required to be used, the structure of the light source connector 420 is simple. Also, as the light guide 410 does not rotate within the flexible hose 114, the durability of the light guide 410 is high.

By the way, also, in the second to eleventh embodiments, in the same manner, the light guide 45 may be divided on the side of the drum 3 and the part extended out of the side of the drum 3 may not be rotated.

FIG. 42 shows the thirteenth embodiment of the present invention.

In this embodiment, the same as, for example, in the seventh embodiment, the light is transmitted by a photocoupler as a means of transmitting the imaging signal from the rotary side to the fixed side in imaging with the imaging apparatus 440 the observed image transmitted by the image guide 211 of fibers.

A light emitting device 451 forming a photocoupler 450 is arranged in the rotation center part within the drum 3, is fixed to the drum 3 by a fixing member 441 and is driven by a driving circuit 442 into which the output signal of the above mentioned imaging apparatus 440 is input through a signal cable 443.

A light receiving device 452 forming the photocoupler 450 is arranged coaxially opposite the above mentioned light emitting device 451 and is fixed to a fixed shaft 445 fixed to the bearing part 8 so as not to rotate even if the drum 3 rotates. Slip ring 446 are provided on the periphery of the outer peripheral part of the above mentioned fixed shaft 445. Contacts 447 contacting these slip rings 446 are provided opposite the above mentioned slip rings 446 in the above mentioned fixing member 441. When the drum 3 rotates, the contacts 447 will rotate but will be always kept in contact with the slip rings 446 which are on the periphery of the fixed shaft 445. These slip rings 446 and contacts 447 are used to feed electric power to the above mentioned imaging apparatus 440 and driving circuit 442 through cables 448 and 449. An electric power feeding and signal transmitting cable 455 connected to the above mentioned slip rings 446 and light receiving device 452 is inserted through the signal cable 103 through the above mentioned fixed shaft 445 and handle 11 and is connected to the video processor 15.

In this embodiment, electric power is fed to the imaging apparatus 440 and driving circuit 442 through the slip rings 446, contacts 447 and cables 448. The observed image transmitted by the image guide 211 is imaged by the imaging apparatus 440. The output signal of this imaging apparatus 440 is input into the driving circuit 442 through the signal cable 443 and is converted to an optical signal by the light emitting device 451 driven by this driving circuit 442. The optical signal from this light emitting device 451 is received by the light receiving device 452 and is converted to an electric signal which is input into the video processor 15. The video signal from this video processor 15 is input into the monitor 17 and the observed image is displayed in this monitor.

According to this embodiment, the video signal which is a high frequency wave likely to be influenced by noise is transmitted without direct contact from the rotary side to the fixed side by using the photocoupler 450 and is therefore less likely to be influenced by noise than by using slip rings.

The other elements are the same as in the seventh embodiment.

Figure 43:
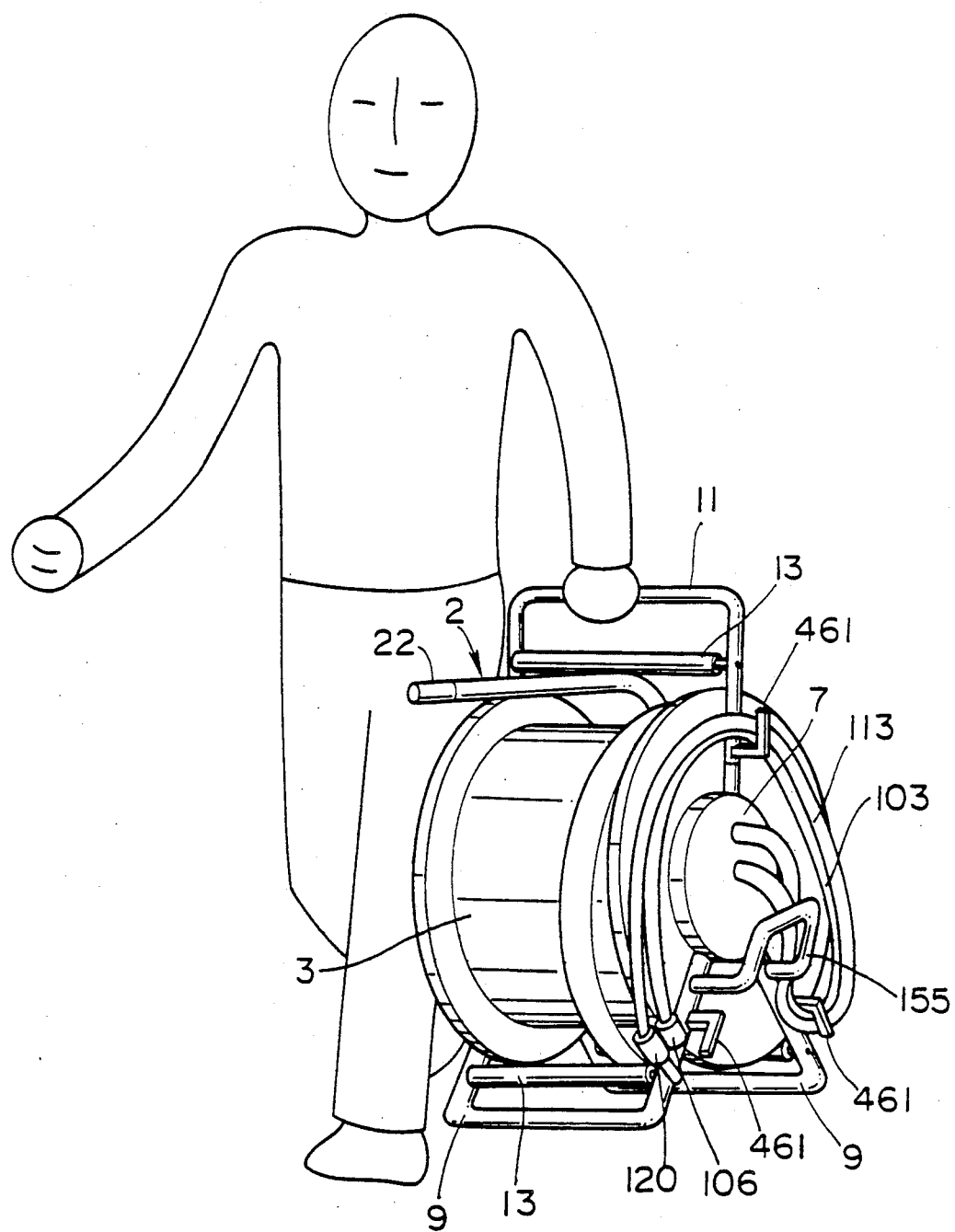
FIGS. 43 and 44 relate to the fourteenth embodiment of the present invention.
Figure 44:
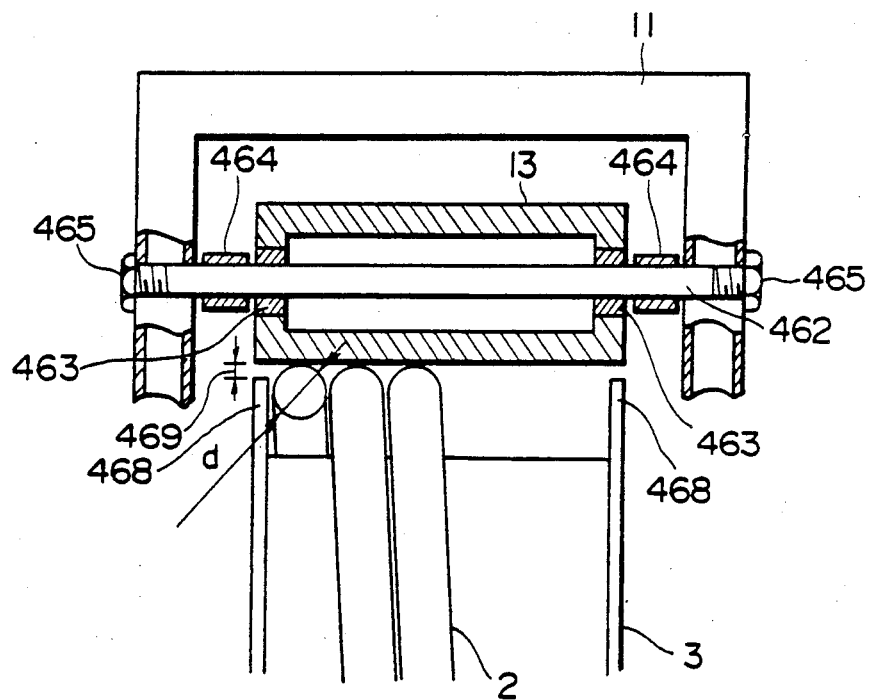

FIGS. 43 and 44 show the fourteenth embodiment of the present invention.

In this embodiment, the same as in the first embodiment, rollers 13 are rotatably fitted to the frames 9 and handles 11 so as to be opposed to the peripheral surface of the drum 3. As shown in FIG. 43, the insertable part 2 is inserted between the peripheral surface of the above mentioned drum 3 and the above mentioned rollers 13 and is wound up on the drum 3. By the way, it is preferable to provide at least three of the above mentioned rollers 13 so that the circle internally contacting the rollers 13, that is, the circle formed by the wound insertable part 2 may be limited to a single coil.

FIG. 44 shows the vicinity of the roller 13 fitted to the handle 11. As shown in this drawing, a shaft 462 is provided in a position opposed to the outer peripheral part of the drum 3 between both sides of the above mentioned handle 11 and is fitted rotatably with the roller 13. Male screw threads are formed on both end parts of the above mentioned shaft 462, pass through both side parts of the above mentioned handle 11 and are fixed to the handle 11 with nuts 465. Collars 464 are interposed between both end parts of the above mentioned roller 13 and the above mentioned handle so as to limit the axial movement of the roller 13. By the way, though not illustrated, in the same manner, the roller 13 fitted to the frame 9 is also rotatably fitted through bearings 463 to the shaft provided between both side parts of the frame 9. By the way, the bearings 463 are not always required and the roller 13 and shaft 462 may be in direct sliding contact with each other.

Flanges 468 for preventing the above mentioned insertable part 2 from dropping are provided on the outer peripheral sides of both end parts of the above mentioned drum 3. As shown in FIG. 44, the gap 469 between the above mentioned roller 13 and the flange 468 of the drum 3 is set to be smaller than the outside diameter d of the above mentioned insertable part 2 so as to prevent the insertable part 2 from dropping out of the drum 3.

As shown in FIG. 43, the above mentioned frame 9 and handle 11 are fitted respectively with cable housing hooks 461 for winding and housing the connecting cable 113 through which the light guide 45 is inserted and the signal cable in the end parts of the above mentioned connecting cable and signal cable.

Also, a guard 155 projecting outside the above mentioned cable housing hooks 461 is provided on the sides of the above mentioned frames 9 to protect the connecting cable 113 and signal cable 103 when these cables 113 and 103 are wound up and housed on the above mentioned cable housing hooks 461.

In this embodiment, the insertable part 2 is inserted between the outer peripheral part of the drum 3 and the above mentioned rollers 13 and is wound up and housed on the drum 3 so as to limit expansion in the outer peripheral direction of the insertable part 2 wound up by the above mentioned rollers 13. Therefore, even if the flexibility of the insertable part 2 is low, the wound insertable part 2 will not expand in the outer peripheral direction due to the bending rigidity of the insertable part 2. The diameter of the drum 3 can be made that much smaller, the insertable part 2 and drum unit including the drum 3 can be made small and light and the portability is improved.

In this embodiment, when the drum unit is not used, as shown in FIG. 43, the connecting cable 113 and signal cable 103 can be wound up and housed on the cable housing hooks 461. Therefore, when the drum 3 is carried or stored, the above mentioned connecting cable 113 and signal cable 103 will not be in the way. Thus, the portability is improved and the storing space can be made small.

Further, in this embodiment, as shown in FIG. 43, when the connecting cable 113 and signal cable 103 are wound up and housed on the above mentioned cable housing hooks 461, these cables 113 and 103 will be protected by the guard 155. A long endoscope is often used to inspect a pipe or the like in a plant. When the drum unit is carried, it will collide with the pipe or such structure as a pillar. According to this embodiment, in such collision, the connecting part particularly with the bearing part 7 of the connecting cable 113 and signal cable will be prevented from being broken. Further, when the drum unit falls down or the like, the connecting cable 113 and signal cable 103 will be protected.

By the way, in this embodiment, the roller 13 is used as a preventing member for preventing the expansion of the insertable part 2 but the preventing member for preventing the insertable part 2 from expanding in the outer peripheral direction may be not only the roller 13 but also a non-rotatable rod or the like.

The other elements are the same as in the first embodiment.

Figure 45:
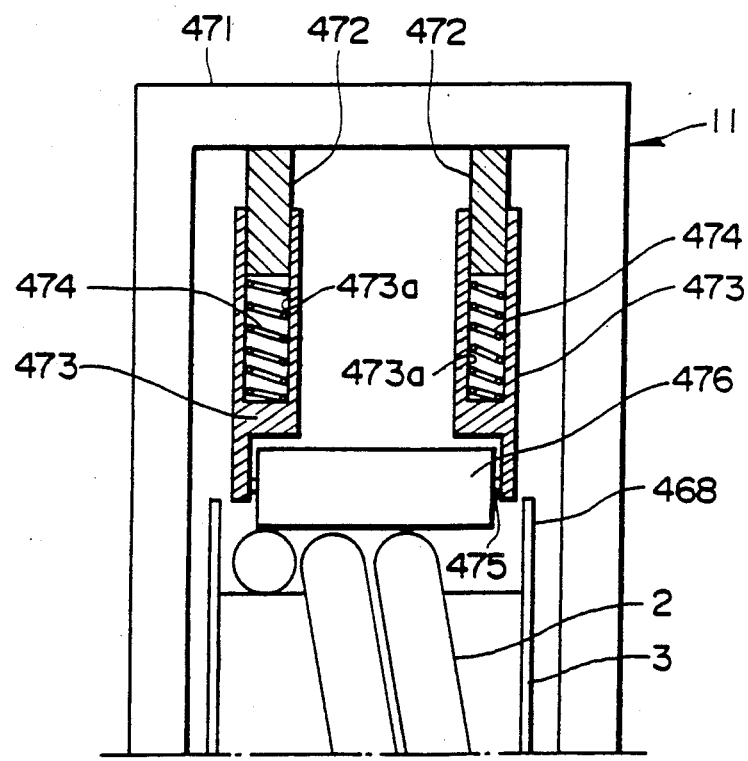
FIG. 45 is a partly sectioned view showing the vicinity of a roller in the fifteenth embodiment of the present invention.

FIG. 45 shows the fifteenth embodiment of the present invention.

In this embodiment, the roller provided as an expansion preventing member is pressed to the drum 3 side.

Two pressing rods 472 are fixed as directed toward the drum 3 inside the straight part 471 of the carrying handle 11 opposed to the outer periphery of the drum 3. Pressing cylinders 473 are slidably externally fitted respectively to the end parts on the drum 3 side of the pressing rods 472. A spring 474 urging the pressing cylinder 473 toward the drum 3 is contained within the hollow part 473a of this pressing cylinder 473. A shaft 475 is provided between the end Parts on the drum 3 side of the above mentioned pressing cylinders 473 and is fitted rotatably with a roller 476 so that the flexible insertable part 2 may be held between the above mentioned roller 476 and the outer periphery of the drum 3 and wound up on the drum 3.

By the way, though not illustrated, rollers pressed toward the drum 3 are also fitted respectively to the frames 9 in the same manner.

The other elements are the same as in the fourteenth embodiment.

According to this embodiment, the insertable part 2 can be better prevented from expanding in the outer peripheral direction and can be wound up on the drum 3.

By the way, in this embodiment, the roller 476 may be pressed not only by the spring 474 but also by rubber or any other elastic material.

The structure pressing the roller 476 toward the drum 3 may be not only the one shown in FIG. 45 but also the roller 476 fitted between pressing rods energized by the pressing cylinders or a roller fitted through plate springs between both side parts of the handle 11.

The roller 476 is used as a preventing member but the preventing member preventing the insertable part 2 from expanding in the outer peripheral direction may be not only the roller 476 but also a non-rotatable rod or the like.

The other elements are the same as in the fourteenth embodiment.

By the way, in the fourteenth embodiment, the preventing member may be not only the roller or rod but also a cylindrical member opposed to the substantially entire outer periphery of the drum 3.

By the way, the present invention is not limited to the above mentioned respective embodiments. For example, a small light source apparatus may be contained within the drum 3 and such signal processing means as a video processor may be separate from the drum 3.

The present invention can be applied to not only an industrial endoscope but also a medical endoscope.

As explained above, according to the first to fifteenth embodiments, in an endoscope apparatus wherein the insertable part can be wound up and housed on a drum, there are effects that the drum can be made light and small and the Portability, workability and operability can be improved.

Figure 46:
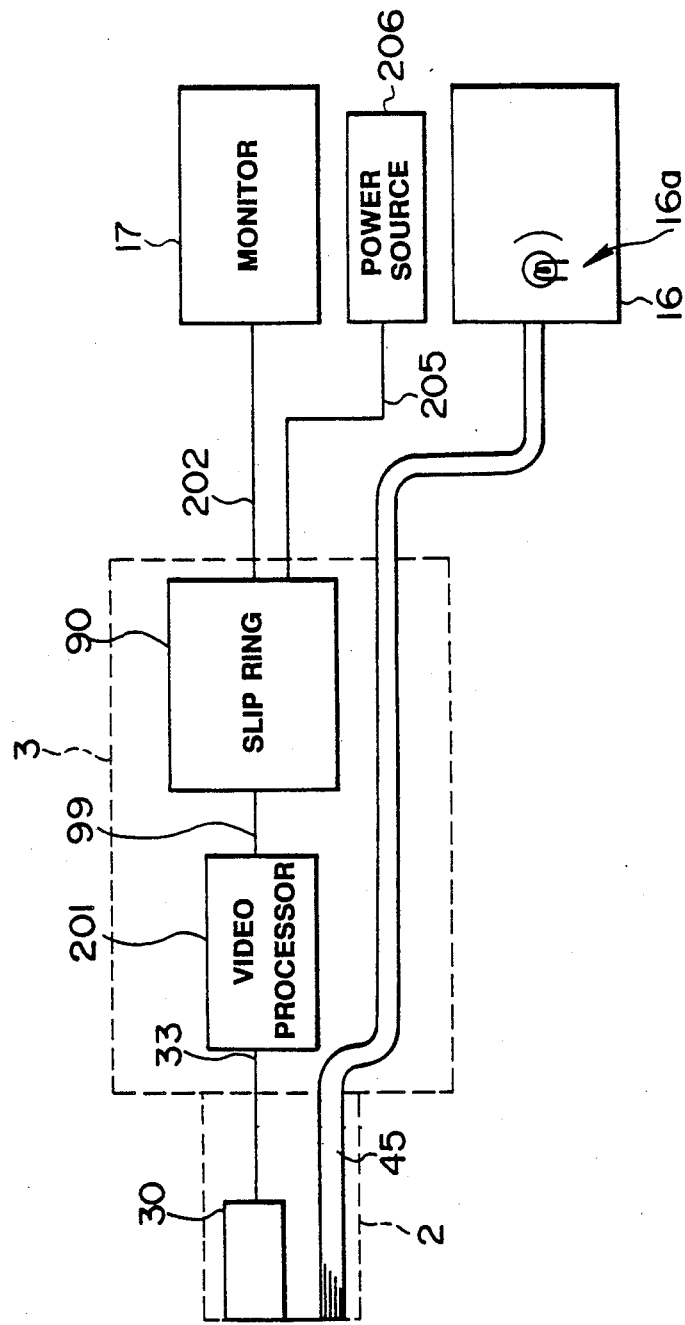
FIGS. 46 and 47 relate to the sixteenth embodiment of the present invention.
Figure 47:
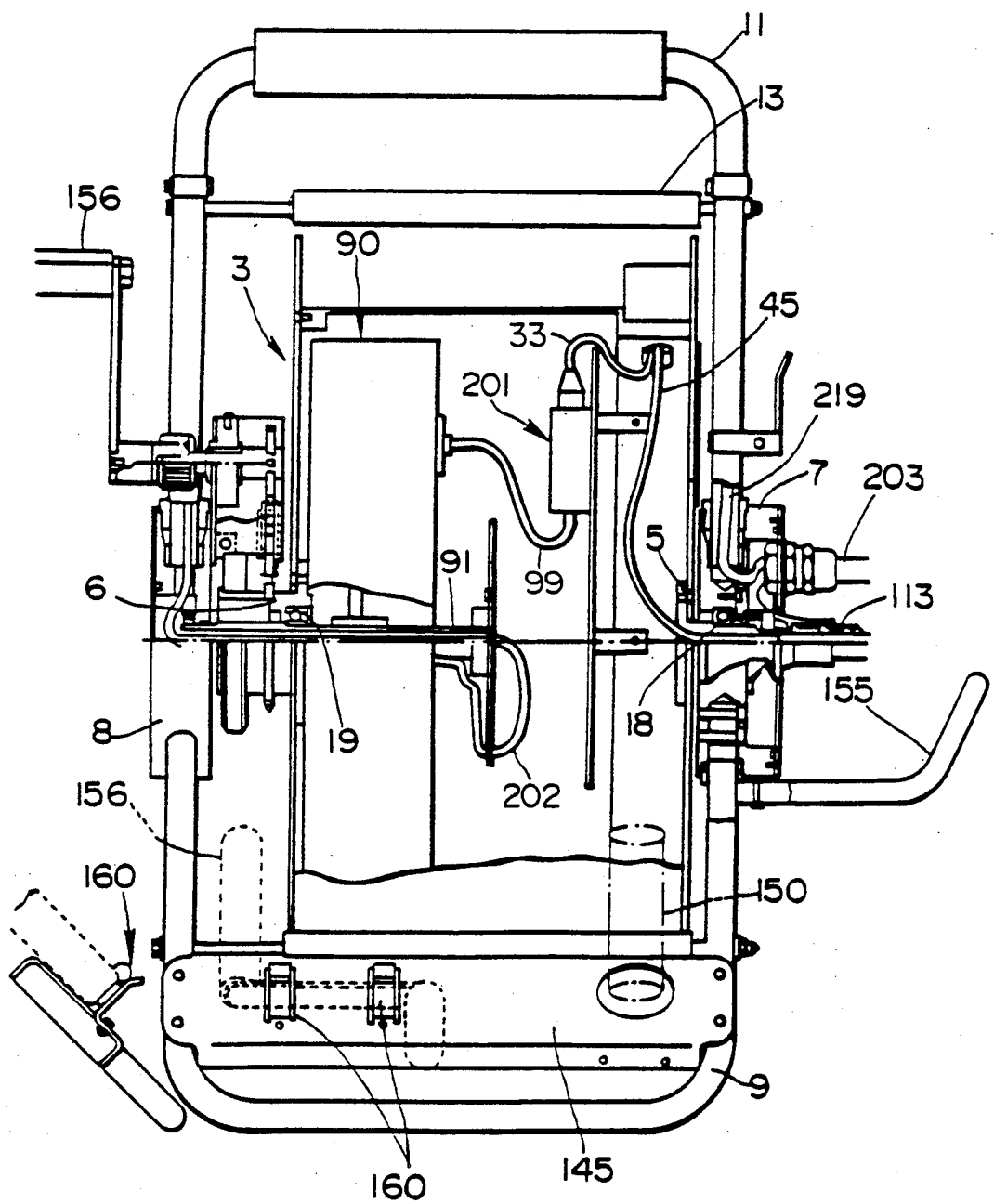

The sixteenth embodiment of the present invention is shown in FIGS. 46 and 47.

In this embodiment, the electric positions of the slip ring 90 and video processor 201 in the sixth embodiment are replaced with each other. That is to say, the video processor 201 is fixed to the drum 3 so as to rotate together with the drum 3, the signal line 33 is connected to the video processor 201, the signal line 99 from this video processor 201 is connected to the slip ring 90 and the signal line 202 from this slip ring 90 is inserted into the video cable 303 and is connected to the monitor 17. The current source cord 205 connected to the current source 206 is connected to the video processor 201 through the above mentioned slip ring 90.

The other elements are the same as in the sixth embodiment.

Generally, the output signals of the video processor 201 are far less in number than the signals between the video processor 201 and solid state imaging device 30, because the signals for driving the solid state imaging device 30 are many.

Therefore, in this embodiment, the poles of the slip ring 90 can be decreased.

The other elements are the same as in the first embodiment.

Figure 48:
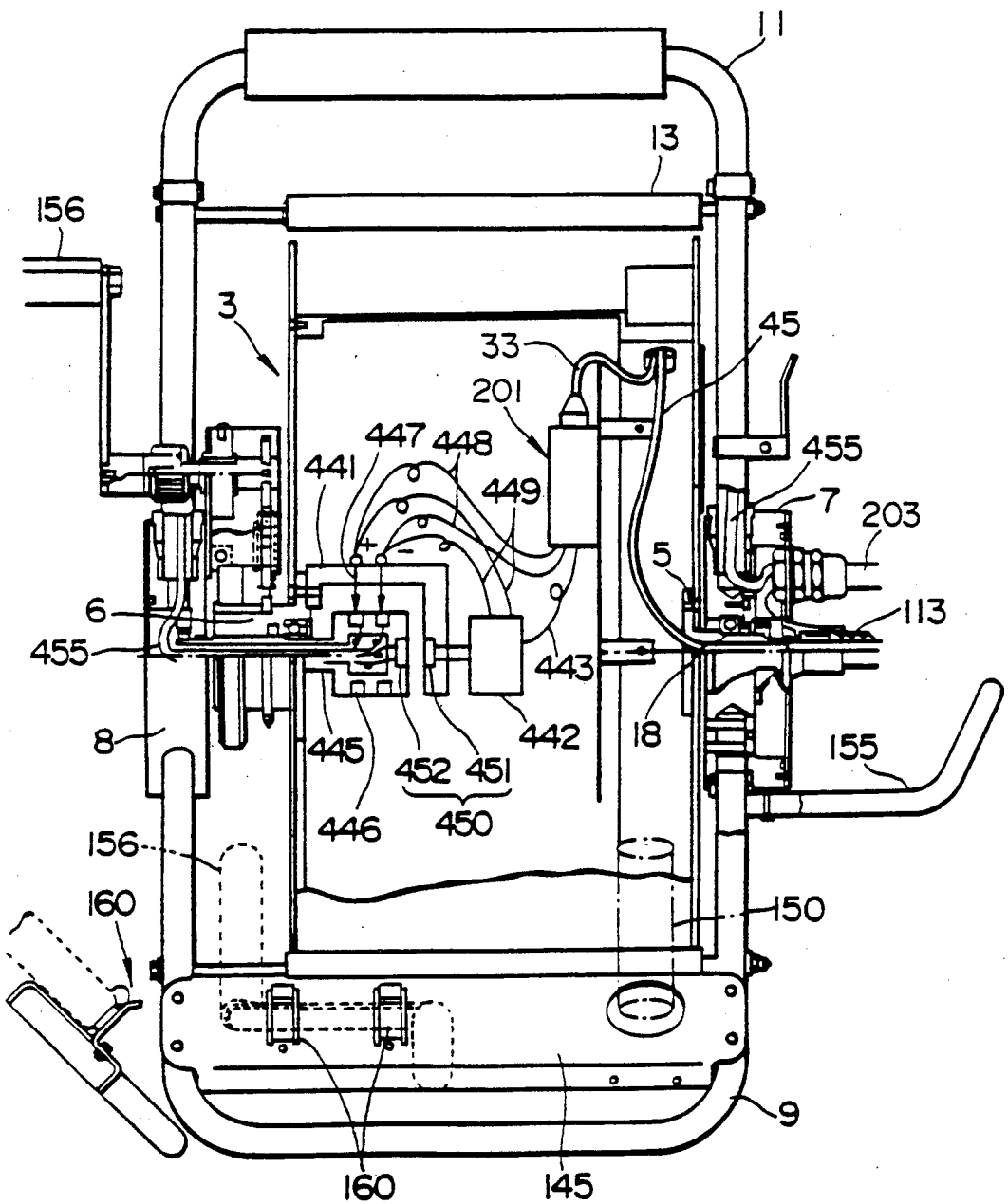
FIG. 48 is a sectional view of a drum in the seventeenth embodiment of the present invention.

The seventeenth embodiment is shown in FIG. 48.

In this embodiment, the photocoupler 450 used in the thirteenth embodiment is used as a means of transmitting the output signal of the video processor 201 in the sixteenth embodiment instead of the slip ring 90. The structure and operation of this photocoupler 450 and its periphery are explained in the thirteenth embodiment and therefore shall not be explained here again. The output signal of the above mentioned video processor 201 is input into the monitor 17 through the above mentioned photocoupler 450 and, as required, through an additional signal processing apparatus provided outside the drum 3.

The electric power for the above mentioned video processor 201 is fed through a slip ring 446, contact 447 and cable 488.

The other elements are the same as in the sixteenth or thirteenth embodiment.

The eighteenth embodiment of the present invention is shown in FIGS. 49 to 54.

Figure 49:
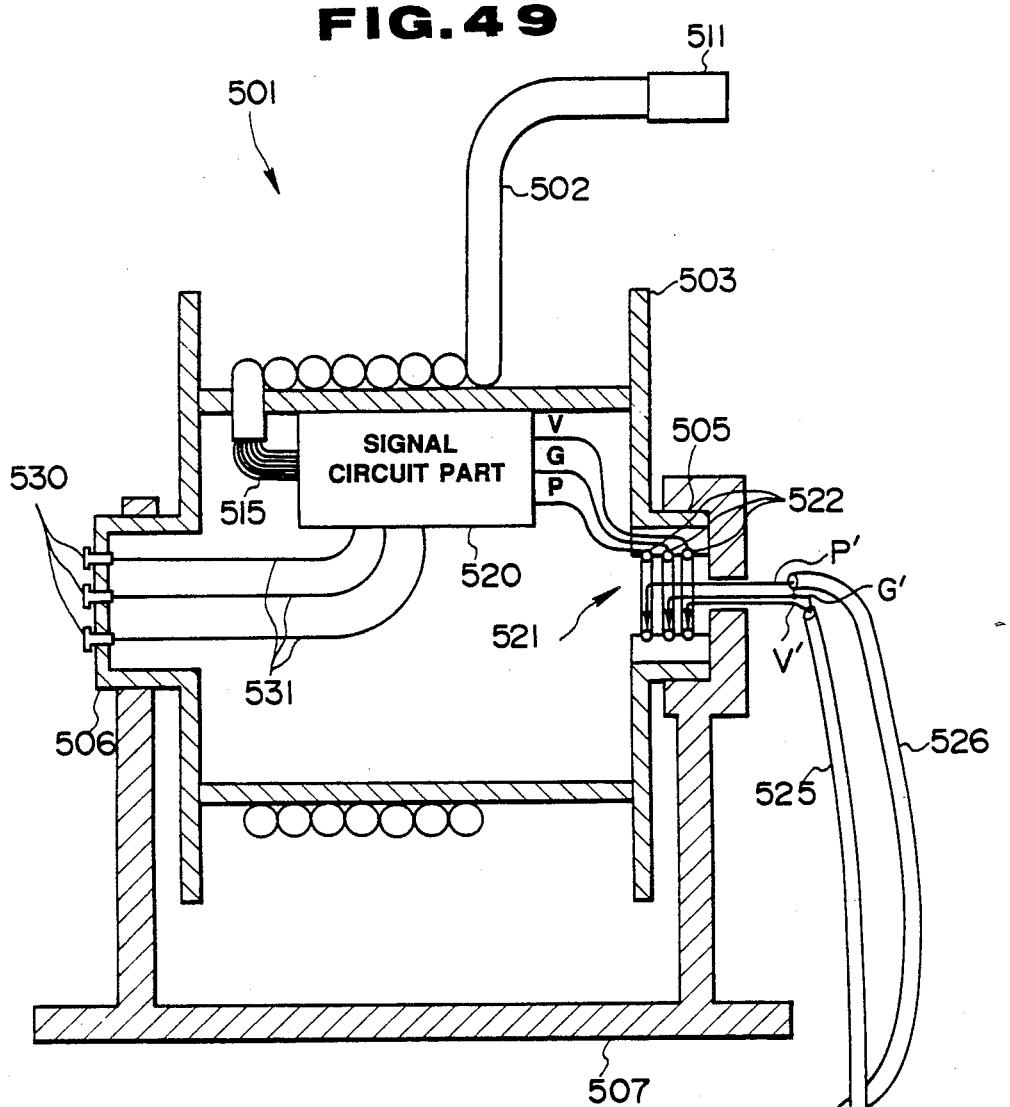
FIGS. 49 to 55 relate to the eighteenth embodiment of the present invention.

As shown in FIG. 49, a winding type endoscope apparatus 501 is provided with an elongate flexible insertable part 502 which is fixed at the base end to a drum 503 as a winding member and is to be wound up and housed on this drum 503. In this winding type endoscope apparatus 501, the above mentioned drum 503 is provided with a separate electric current source unit 529 and monitor television 528.

The above mentioned drum 503 is provided at both ends in the rotary axial direction with cylindrical rotary axial parts 505 and 506 which are rotatably supported by a stand 507 through bearings not illustrated.

Figure 50:
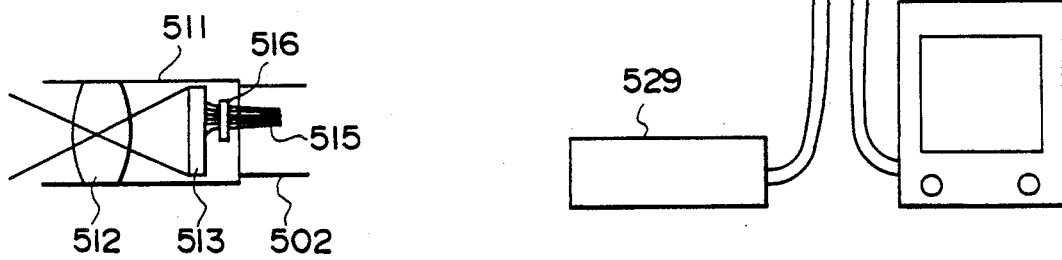

The above mentioned insertable part 502 is provided on the tip side with a rigid tip part 511. As shown in FIG. 50, an objective lens 512 and an imaging means 513 using a solid state imaging device arranged in the image forming position of this objective lens 512 are provided within the above mentioned tip part 511. Many signal lines 515 for operating the above mentioned imaging means 513 are inserted through the above mentioned insertable part 502 and are connected on one end to the above mentioned imaging means 513 through a miniature electric part 516.

An illuminating lens not illustrated or the like is provided as required in the above mentioned tip part 511. By the way, the illuminating system by such illuminating lens and light guide may be of the same formation as of the illuminating system shown in the first embodiment.

As shown in FIG. 49, the above mentioned signal lines 515 are led at the other ends into the drum 503 to be connected to a signal circuit part 520 fixed within this drum 503. As this signal circuit part 520 rotates together with the drum 503, the signal lines 515 are connected directly with the signal circuit Part 520 without using a slip ring.

The above mentioned signal circuit part 520 is provided with a driving circuit feeding driving pulses to the above mentioned imaging means 513 and a video signal processing circuit for processing the picture image signal from the above mentioned imaging means 513 so as to be a video signal so that all the electric imaging process may be made and, for example, an NTSC system video signal may be output. This NTSC video signal will be able to be transmitted if there are two poles of an electric line represented by V and an earthing line represented by G in FIG. 49. In order to operate the above mentioned signal circuit part, a current source is necessary. If there are two poles for the current source, signals can be transmitted. As the earthing line G can be utilized for one of the poles, one pole represented by P may be provided. These three electric lines V, G and P are connected to ring-like electrodes 522 of a slip ring 521. By the way, the above mentioned slip ring 521 is provided within the above mentioned rotary shaft part 505 and the above mentioned ring-like electrodes 522 rotate together with the above mentioned drum 503. This slip ring 521 may be small and cheap with only three poles. Brush-like electrodes respectively contact the above mentioned ring-like electrodes 522 and are connected with electric lines V', G' and P. The electric line V' is connected to an internal conductor of a cable 525, the electric line P' is connected to an internal conductor of a cable 526 and the electric line G' is connected to an external conductor of the cable 525 and an external conductor of the cable 526. The above mentioned cable 525 is connected to the above mentioned monitor television 528. The above mentioned cable 526 is connected to the above mentioned current source unit 529. Thus, the NTSC video signal from the above mentioned signal circuit part 520 is transmitted to the monitor television 528 by the cable 525. On the other hand, the current source is fed to the signal circuit part 520 by the cable 526 from the current source unit 529.

Also, as shown in FIG. 49, switches 530 for controlling the operation of the signal circuit part 520 are provided on the end surface of the rotary shaft part 506 of the drum 503 and are connected to the above mentioned signal circuit part 520 by the signal lines 531 to control such functions as, for example, white balancing and gain increasing.

By the way, as the switch is provided on the front panel of the camera control unit 15 in the apparatus shown in FIG. 1 but is fitted to the drum 503 in this embodiment, if the drum 503 is rotated, the switch 530 will also rotate together. However, in the case of operating the switch 530, the rotation of the drum 503 may be stopped for a while and there will be no inconvenience in practice.

Figure 51:
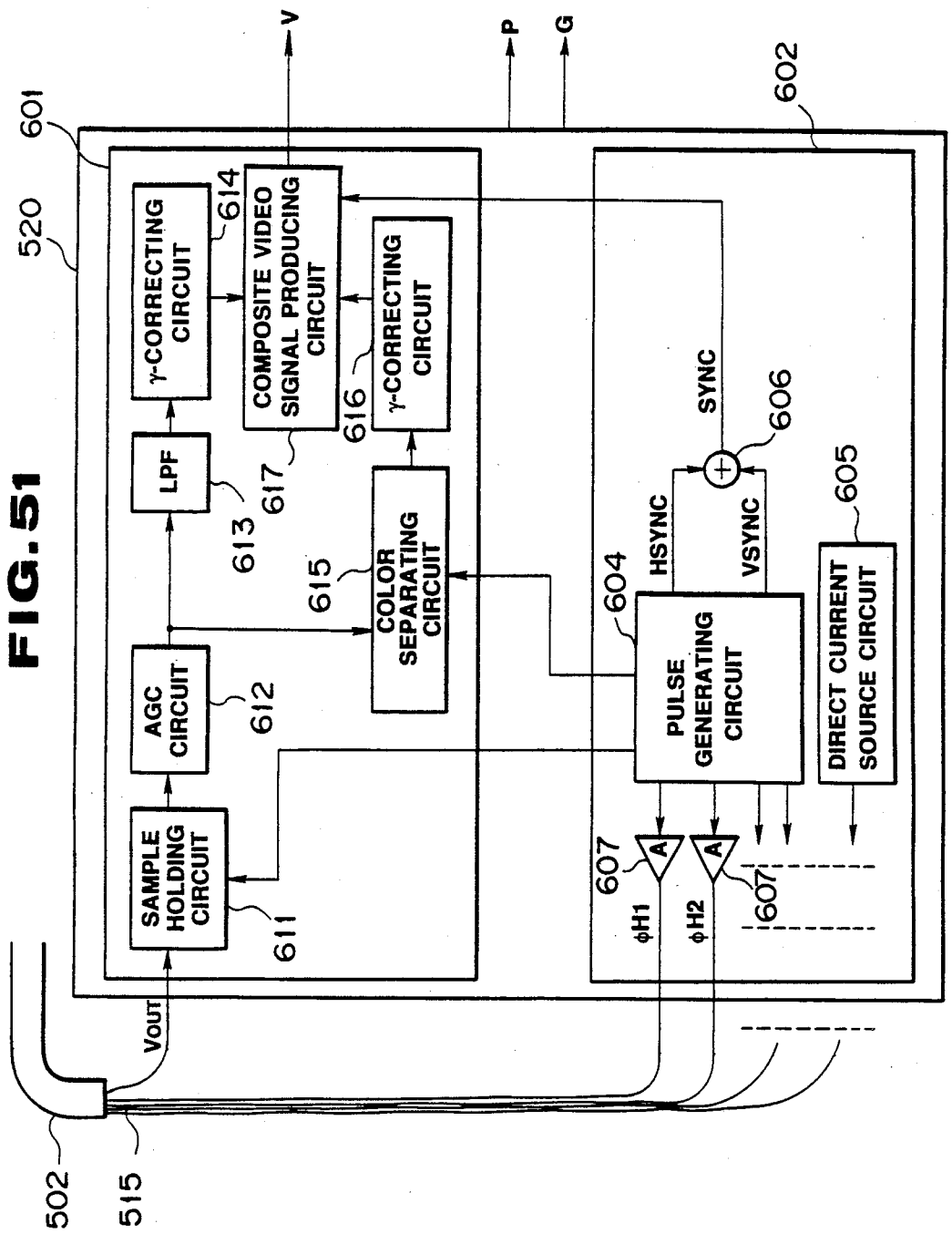

Now, the above mentioned signal circuit part 520 is formed as shown in FIG. 51.

That is to say, the signal circuit part 520 comprises a signal processing circuit 601 and a driving circuit 602. The driving circuit 602 is provided with a pulse generating circuit 604 for generating driving pulses required to operate the imaging means 513 and a direct current source circuit 605 for generating a direct current voltage required to also operate the imaging means 513. By the way, as explained by using FIG. 71, the above mentioned driving pulses are $\phi H_1$, $\phi H_2$, etc. and are output through amplifiers 607. The above mentioned pulse generating circuit 604 generates also pulses for operating a sample holding circuit 611 and color separating circuit 615 within the signal processing circuit 601 and also generates a horizontal synchronizing signal HSYNC and vertical synchronizing signal VSYNC which are compounded by a mixer 606 to be output as a synchronizing signal SYNC.

On the other hand, the above mentioned signal processing circuit 601 is provided with the above mentioned sample holding circuit 611 which inputs a video signal $V_{out}$ output from the imaging means 513, removes pulse components from it and makes it a continuous video signal. The output of this sample holding circuit 611 is input into an AGC circuit 612 which varies the amplitude in response to the brightness of the object to always keep the output substantially constant. The output of this AGC circuit 612 is input into a low-pass filter (LPF) 613 and color separating circuit 615. The above mentioned low-pass filter 613 removes a high band component which is a color signal component in the input signal and leaves only a luminance signal. The luminance signal output from this low-pass filter 613 is input into a gamma correcting circuit 614 and is gamma-corrected. On the other hand, the above mentioned color separating circuit 615 takes out only a color signal which is a high band component in the input signal. The color signal output from this color separating circuit 615 is input into a gamma correcting circuit 616 and is gamma-corrected. The luminance signal and color signal r corrected in the above mentioned gamma correcting circuits 614 and 616 are input into a composite video signal producing circuit 617 into which the above mentioned SYNC is also input. By using these signals, the above mentioned composite video signal producing circuit 617 outputs, for example, an NTSC system video signal.

Figure 52:
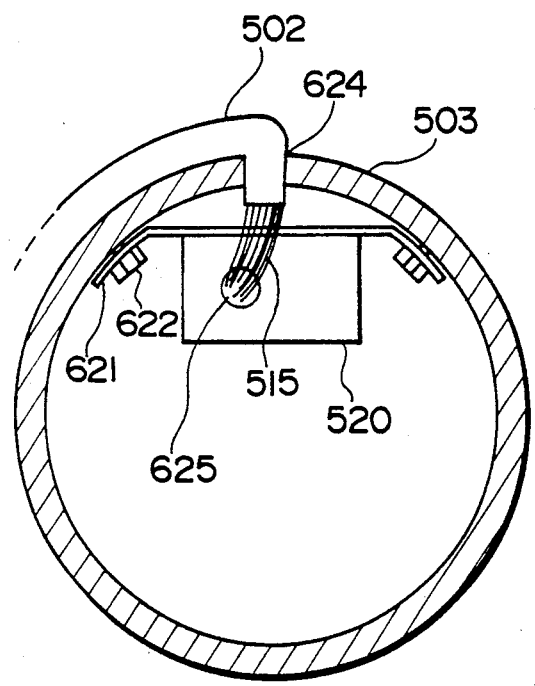

The above mentioned signal circuit part 520 is fitted to the drum 503 as shown, for example, in FIG. 52. That is to say, the outer fitting of the signal circuit part 520 is box-like and is fixed to a fitting plate 621 which is fixed to the drum 503 with bolts 622. Therefore, the signal circuit part 520 rotates integrally with the drum 503. The above mentioned drum 503 is provided with a hole 624 into which the insertable part 502 is led at the base end. The insertable part 502 is securely fixed to the drum 503 in this hole 624. The signal lines 515 inserted through the above mentioned insertable part 502 are led out of the end of the insertable part 502 within the drum 503 and are connected to the signal circuit part 520 by a connector 625. As the drum 503 and signal circuit part 520 are made integral, even if the drum 503 rotates, the signal lines 515 will never be forced to move. The operation of this embodiment of the above mentioned construction shall be explained in the following.

An electric current is fed to the signal circuit part 520 through the cable 526 and slip ring 521 from the current source unit 529. The driving pulses from the driving circuit within this signal circuit part 520 are fed to the imaging means 513 provided in the tip part 511 of the insertable part 502 through the signal lines 515 without passing through the slip ring. This imaging means 513 is driven by the above mentioned driving pulses to image the object image formed by the objective lens 512. The output signal of this imaging means 513 is input into the above mentioned signal circuit part 520 through the signal lines 515 without passing through the slip ring and, for example, an NTSC video signal is output from the signal processing circuit within this signal circuit part 520 and is input into the monitor television 528 through the slip ring 521 and cable 525 to display the object image in this monitor television 528.

Such functions as white balancing and gain increasing are controlled by the operation of the switch 530.

Thus, according to this embodiment, as the imaging means 513 is provided in the tip part 511 and no image guide is used, a favorable picture image is obtained at a high resolution.

Figure 68:
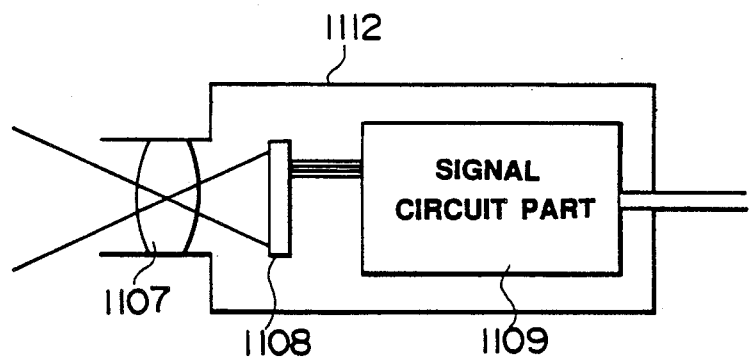
Figure 69:
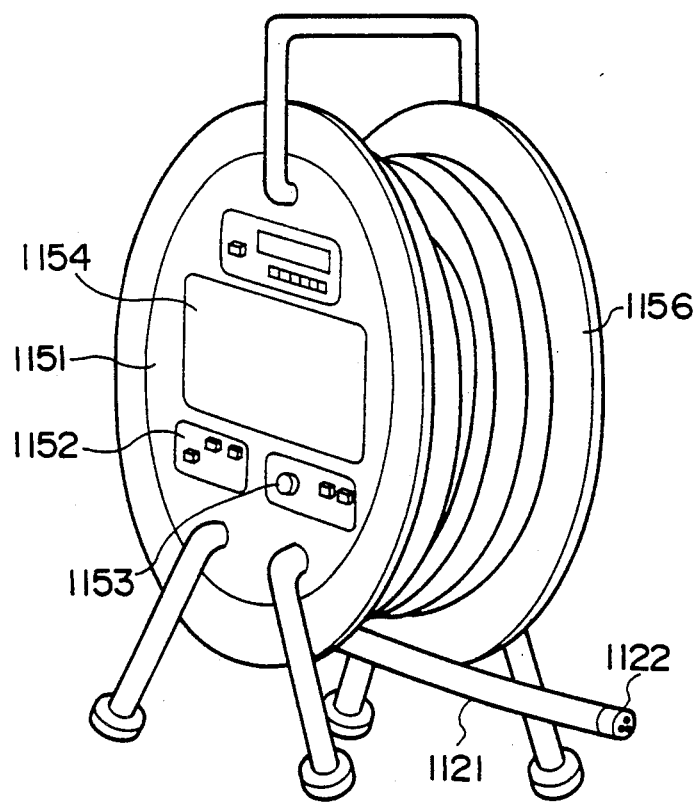
Figure 70:
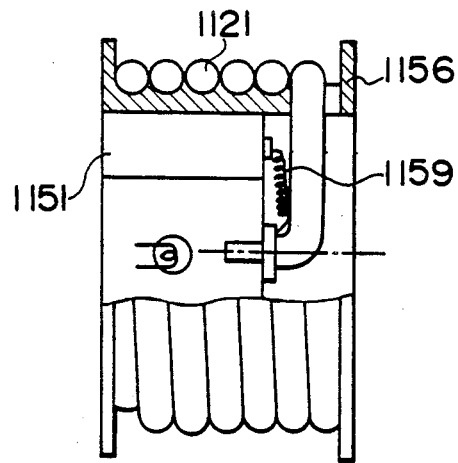

Also, the above mentioned tip part 511 does not contain such signal circuit part 1109 as is shown in FIG. 68 and therefore can be made so small as to be inserted into a fine tube.

If the camera controlling unit is separated from the drum, the signal lines connected to the imaging means will have to be connected to the camera controlling unit arranged outside the drum and therefore a slip ring of very many poles will be required. On the other hand, in this embodiment, as the signal circuit part 520 is fitted to the drum 503 and is rotated together with this drum 503, the imaging means 513 and signal circuit part 520 are directly connected with each other without the slip ring of many poles. Therefore, the large expensive slip ring of many poles is not required and nearby televisions, radios and wireless instruments will not be affected by the electromagnetic waves radiated in the space from the slip ring.

Figure 53:
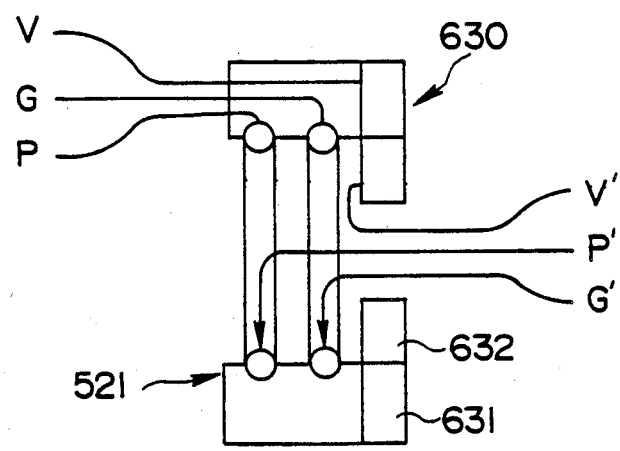
Figure 54:
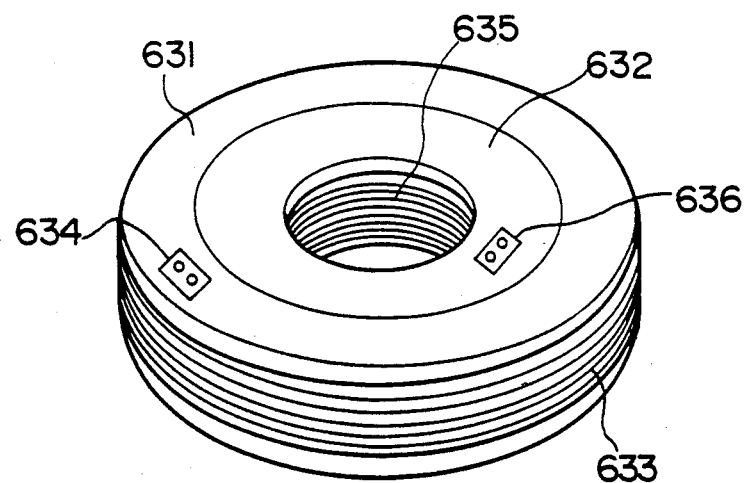
Figure 55:
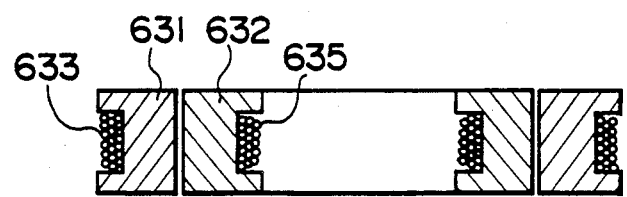

By the way, in FIG. 49, the slip ring 521 is of a three-pole structure. However, as shown in FIG. 53, if the signal V is modulated on a high frequency carrier signal and is transmitted through a rotary transformer 630, the slip ring 521 will be able to be of a two-pole structure of only the signals P and G. As shown in FIGS. 54 and 55, the above mentioned rotary transformer 630 has a cylindrical outside core 631 and a cylindrical inside core 632 arranged rotatably inside this outside core 631. The above mentioned outside core 631 is wound with an outside winding 633 connected to an outside terminal 634. Also, the above mentioned inside core 632 is wound with an inside winding 635 connected to an inside terminal 636. The high frequency signal carrying the above mentioned signal V is applied to the outside winding 633 through the outside terminal 634 and creates a magnetic field by this outside winding 633 to excite the inside winding 635 through the outside core 631 and inside core 632. Therefore, the same high frequency signal as is applied to the outside terminal 634 will be generated in the inside winding 635 to be taken out of the inside terminal 636. The outside core 631 and inside core 632 can be freely rotated with each other. Therefore, the electric circuit connected to the outside terminal 634 and the electric circuit connected to the inside terminal 636 in case they rotate with each other can be utilized to transmit the high frequency signal. In the slip ring 521 in FIG. 49, the signal V transmitting part can be replaced with the rotary transformer 630.

Figure 56:
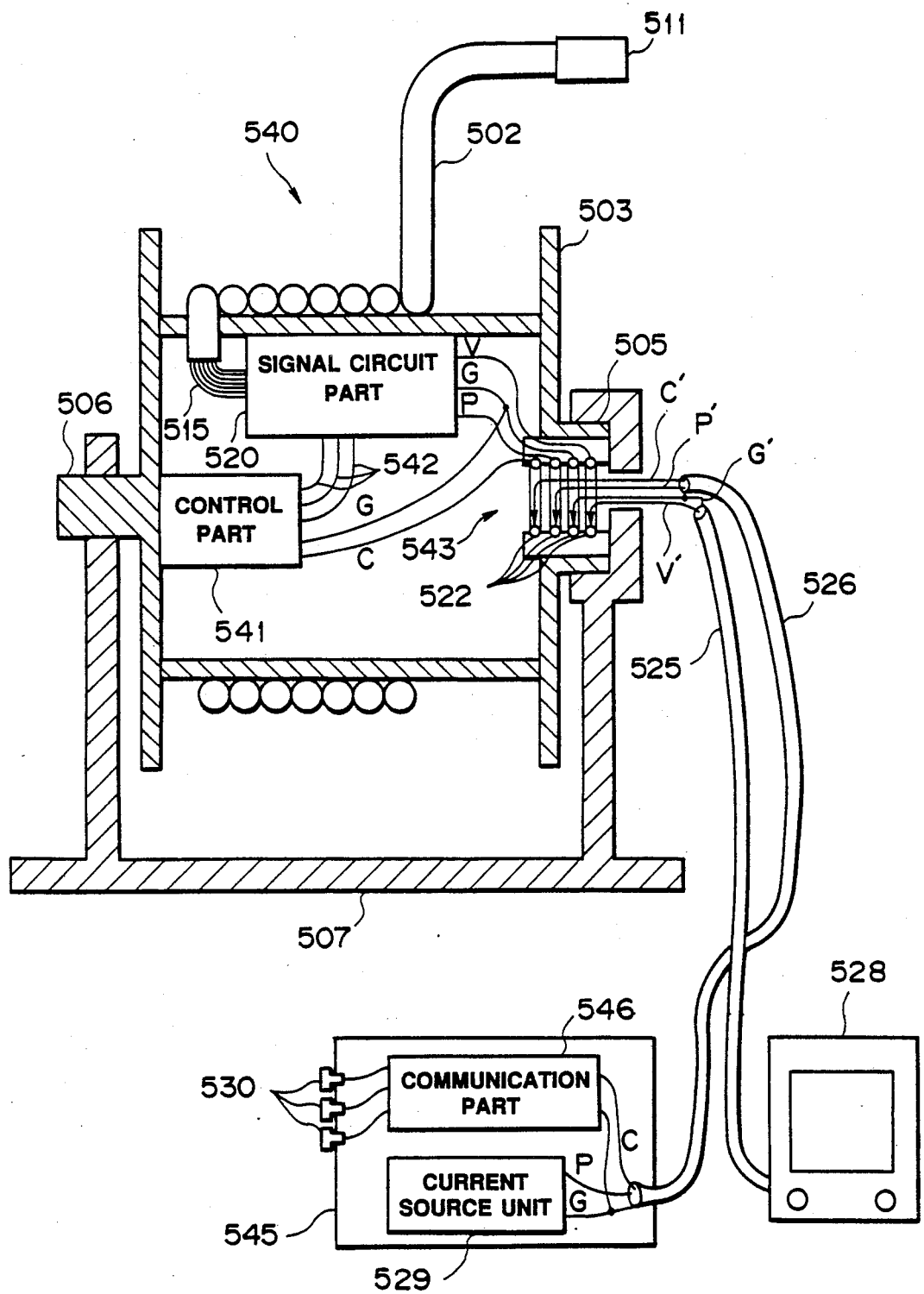
FIG. 56 is an explanatory view showing the structure of an endoscope apparatus of the nineteenth embodiment of the present invention.

The nineteenth embodiment of the present invention is shown in FIG. 56.

In the winding tyPe endoscope apparatus 540 of this embodiment, a control part 541 is further built-in within the drum 503, is fitted to rotate together with the drum 503 and is connected to the signal circuit part 520 by signal lines 542. A slip ring 543 in a four-pole structure with the addition of one pole is provided instead of the slip ring 521 to feed a control signal to the above mentioned control part 541 by utilizing the additional pole C and the earthing line G. The signal line C', earthing line G' and current source line P' corresponding to the additional pole C connected to the brush-like electrodes of the slip ring 543 are connected to the cable 526.

Also, an operator unit 545 to which the above mentioned cable 526 is connected is provided separately from the drum 503 and has a switch 530, a communication part 546 connected to this switch 530 and a current source unit 529. There is no such switch 530 as in the eighteenth embodiment. The signal circuit part 520 is controlled by operating the switch 530 of the above mentioned operator unit 545. That is to say, the operation of the above mentioned switch 530 is transmitted to the communication part 546 and control data are transmitted to the control part 541 within the drum 503 by such serial communication system as, for example, an RS-232C system by using the two poles of the signal line C and earthing line G connected to this communication part 546. The above mentioned control part 541 receives these data and controls the signal circuit part 520 through the signal line 542 in response to the contents to operate, for example, white balancing.

The other elements are the same as in the eighteenth embodiment.

According to this embodiment, as the switch 530 is provided not on the drum 503 but on the operator unit 545, even if the drum 503 is left rotating, the switch 530 will be able to be operated.

Figure 71:
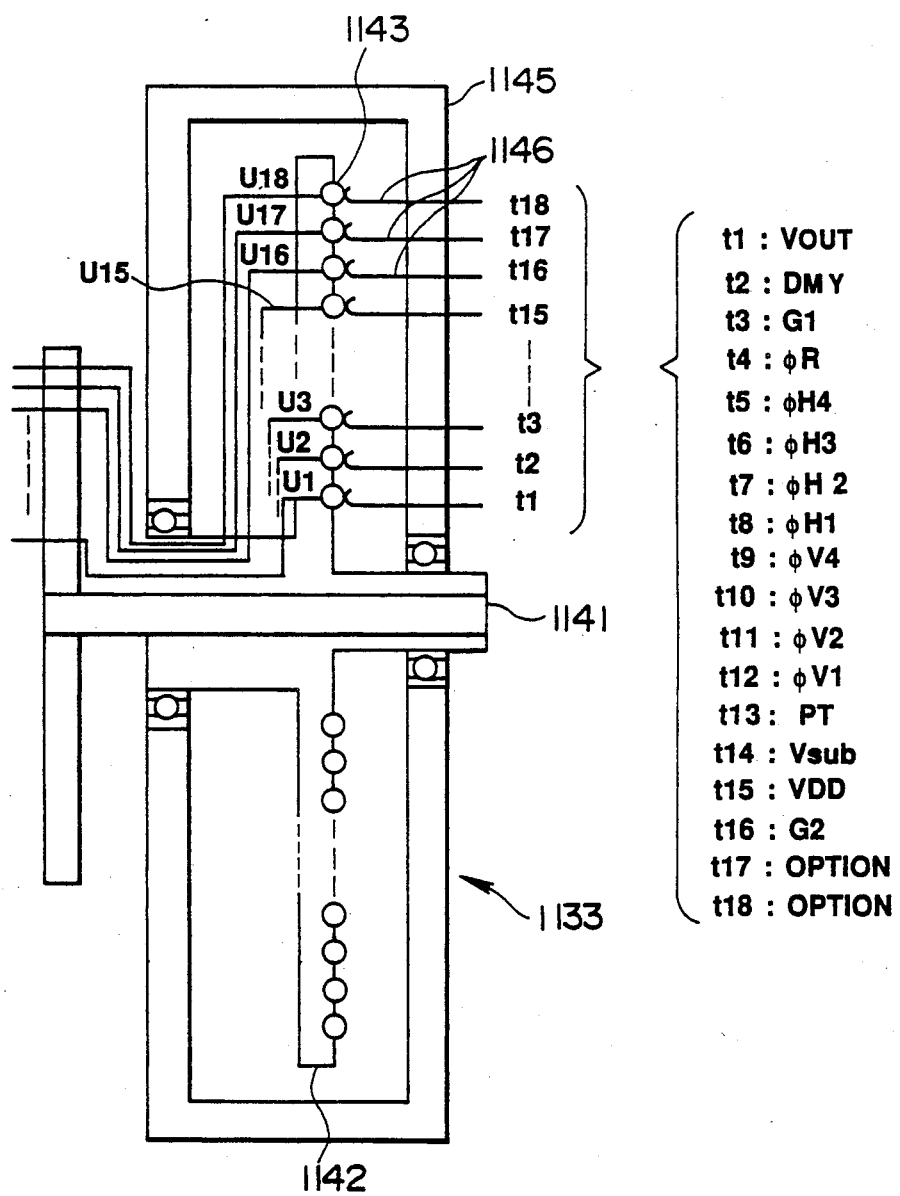

As the slip ring 543 is of four poles at most, there can be formed an apparatus still smaller, lighter and cheaper than such apparatus using a slip ring of many poles as is shown in FIG. 71.

The other elements are the same as in the eighteenth embodiment.

Figure 57:
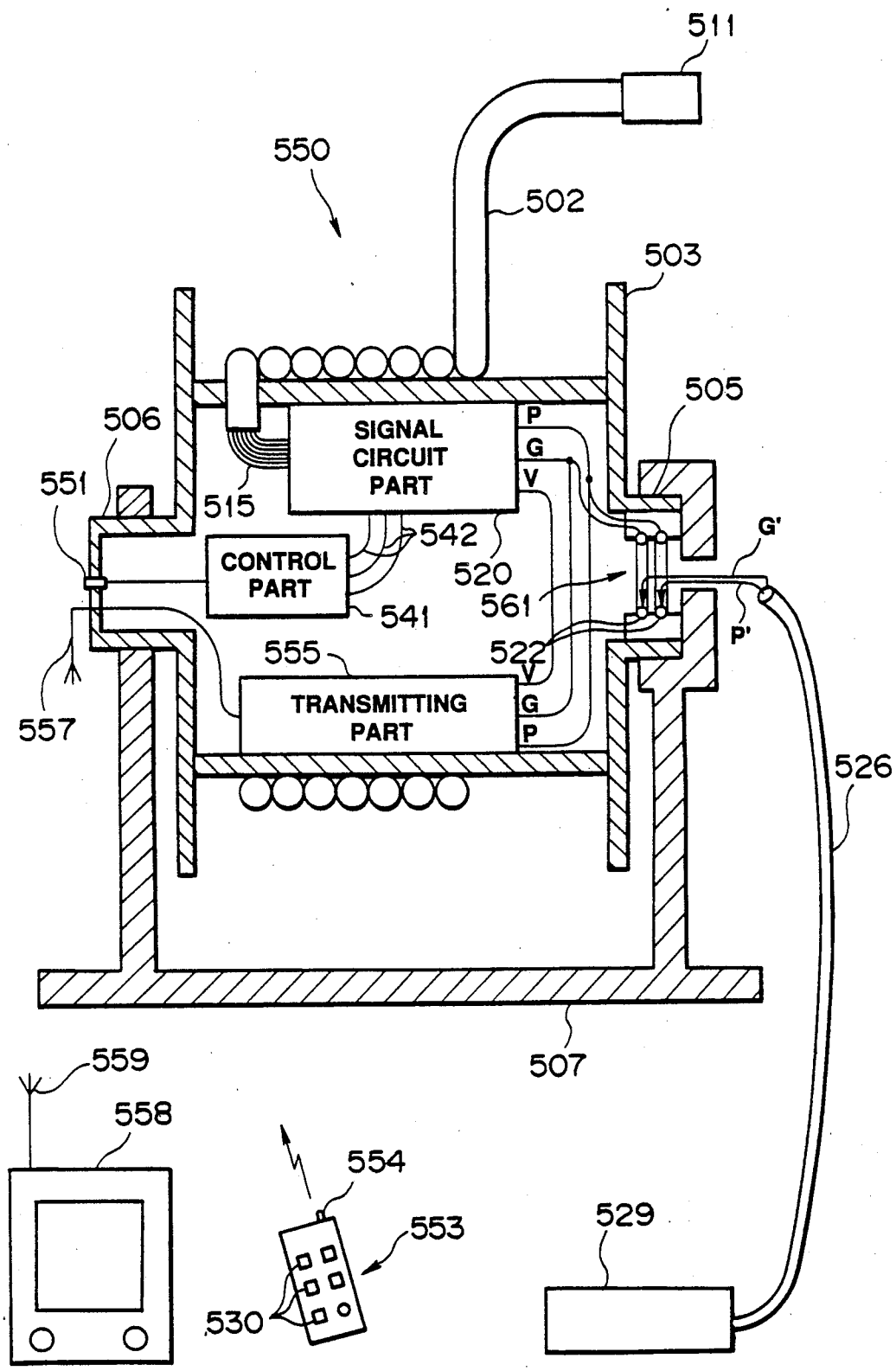
FIG. 57 is an explanatory view showing the structure of an endoscope apparatus of the twentieth embodiment of the present invention.

The twentieth embodiment of the present invention is shown FIG. 57.

In the winding type endoscope apparatus 550 of this embodiment, a control part 541 connected to the signal circuit part 520 is provided within the drum 503 and a light receiving device 551 is provided on the end surface of the rotary shaft part 506 of the drum 503 and is connected to the above mentioned control part 541. Also, a remote control unit 553 is provided separately from the drum 503 and is provided with a switch 530 and light emitting device 554 so that, when the above mentioned switch 530 is operated, the data corresponding to it will be encoded and infrared rays will be emitted from the light emitting device. These infrared rays are received by the above mentioned light receiving device 551 provided on the drum 503 and the signal circuit part 520 is controlled in response to the contents by the control part 541.

A transmitting part 555 is provided within the above mentioned drum 503 and is connected with the electric lines V, G and P. The NTSC video signal output from the signal circuit part 520 enters the transmitting part 555 through the signal line V, is converted to such electric wave as of the UHF band of the television and is transmitted from an antenna 557 provided on the end surface of the rotary axis part 506 of the drum 503. This electric wave is enough with a feeble wave recognized in the Electric Wave Law. In this embodiment, an antenna 559 is used instead of the monitor television 528 of the eighteenth and nineteenth embodiments and a monitor television 558 having a built-in tuner for receiving the general television broadcast is used. If the transmitting frequency of the transmitting part 555 is set in advance at a frequency not used in the television broadcast and the receiving frequency of the monitor television 558 is conformed to it, the video image imaged by the endoscope apparatus of this embodiment will be displayed in the monitor television 558.

In this embodiment, a slip ring 561 of two poles is provided instead of the slip ring 521 of the eighteenth embodiment and is fitted with the electric lines P and G connected with the signal circuit part 520 and transmitting part 555.

The other elements are the same as in the eighteenth embodiment.

Thus, in this embodiment, in the slip ring 561, as the current to be fed to the signal circuit part 520 and transmitting part 555 may be received from the current source unit 529 and may be led into the drum 503, the lines P and G may be of two poles and the structure is very simple and small.

Also, in this embodiment, the switch is operated from the remote control unit 553 and can be therefore brought to any free position to be convenient to operate.

Further, the monitor television 558 is different from that of the eighteenth and nineteenth embodiments, requires no video signal cable and therefore can be placed in any free position or can be carried by the user while seeing the video image by using a portable liquid crystal television popularized in recent years.

The other elements are the same as in the eighteenth embodiment.

Figure 58:
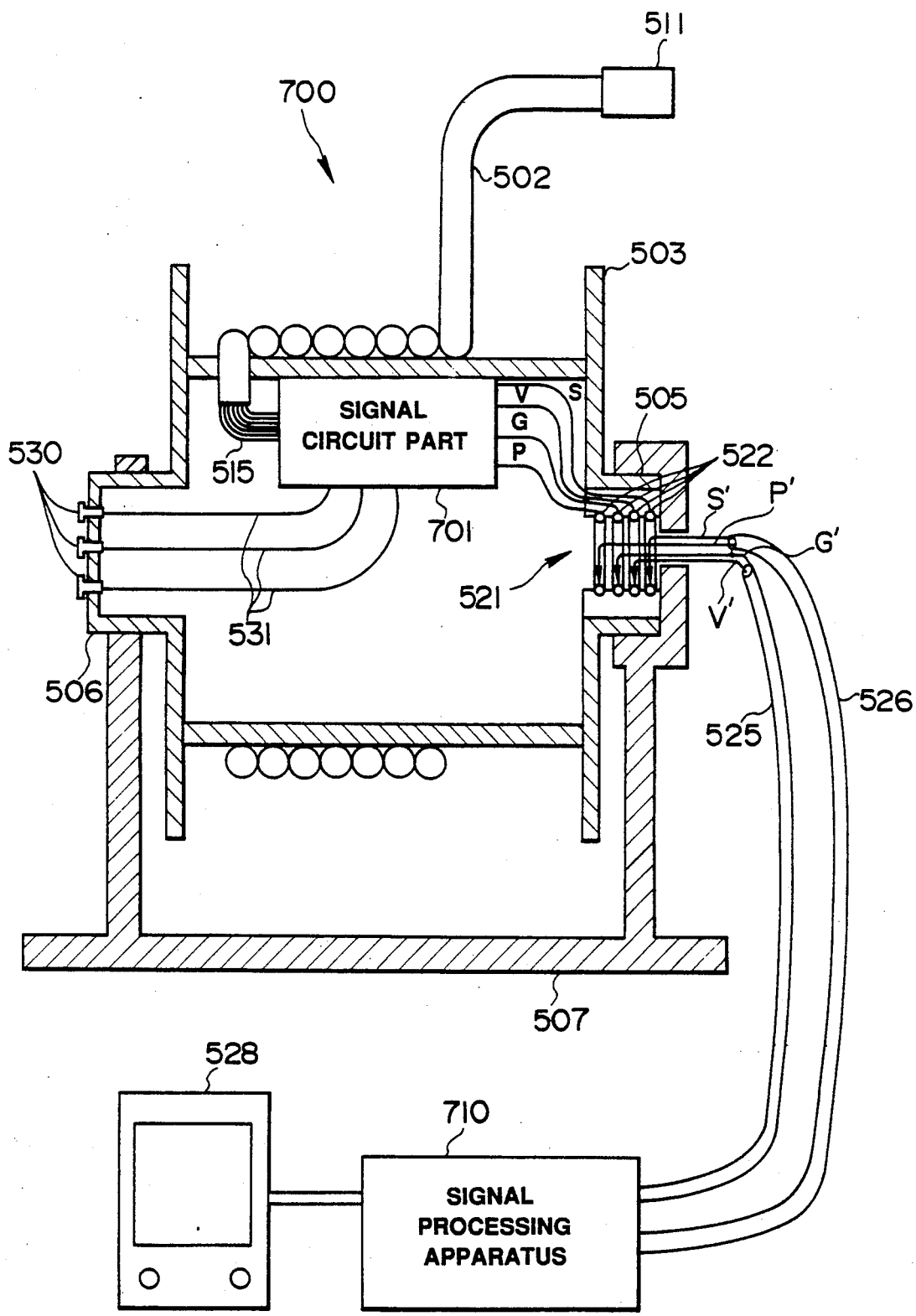
FIGS. 58 to 60 relate to the twenty-first embodiment of the present invention.
Figure 59:
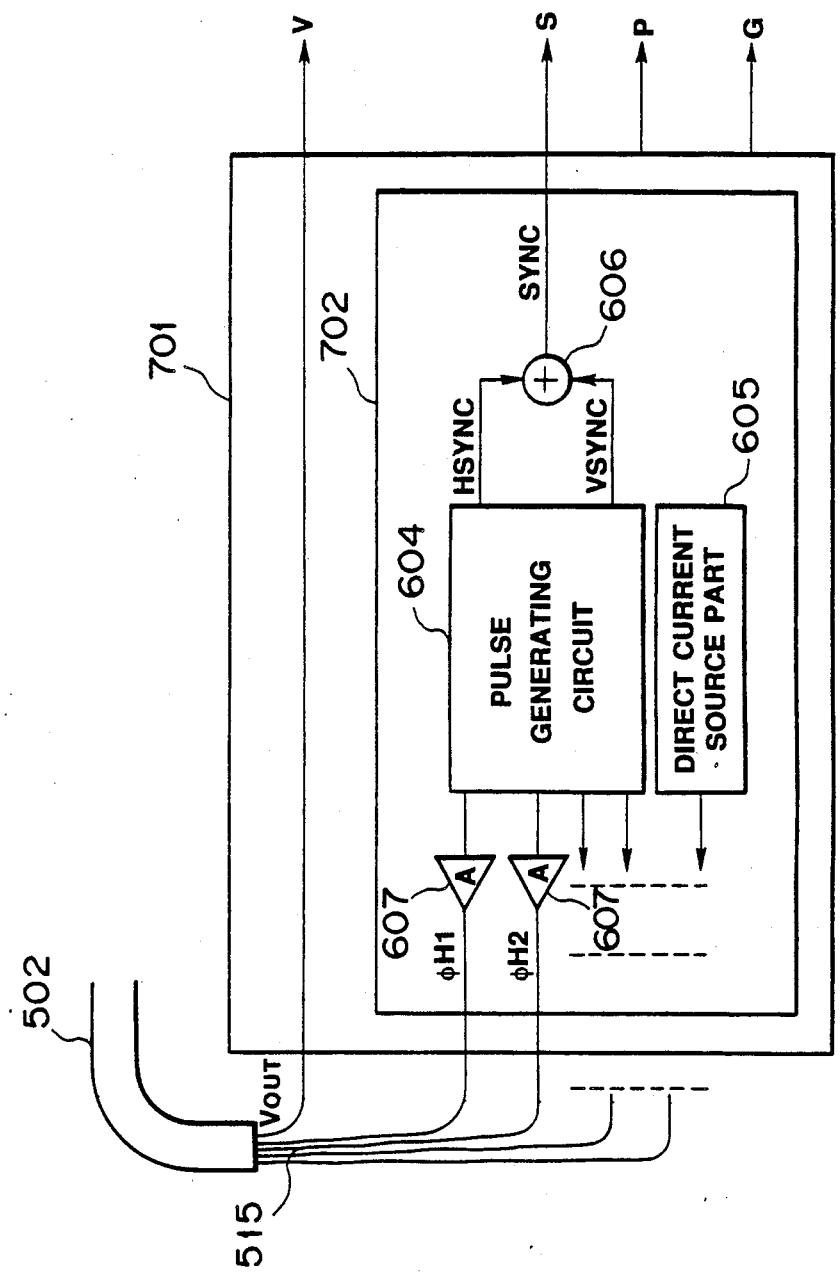
Figure 60:
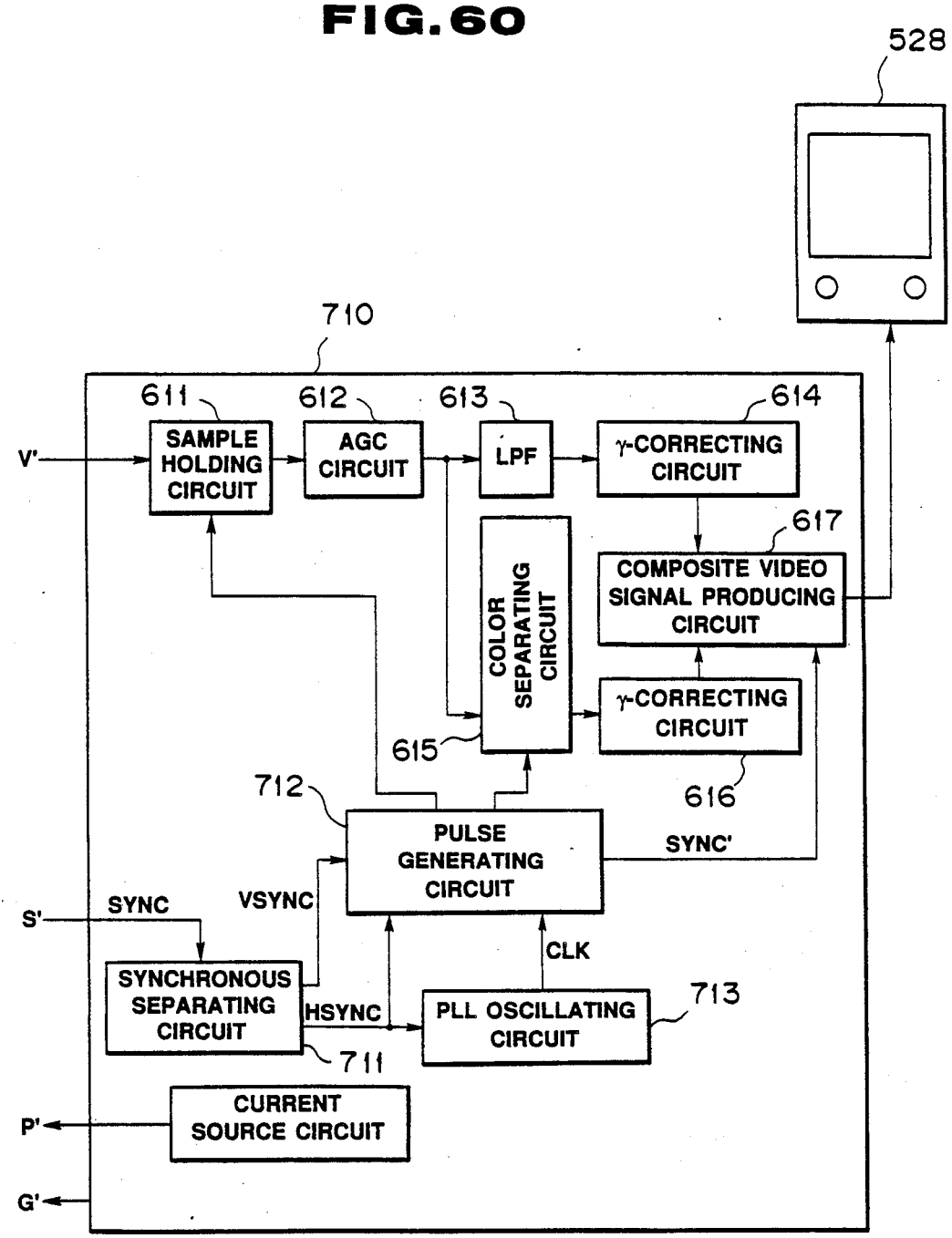

The twenty-first embodiment of the present invention is shown in FIGS. 58 to 60.

In this embodiment, only the driving circuit of is made integral with the drum.

In the winding type endoscope apparatus 700 in this embodiment, the signal circuit part 701 fixed to the drum 503 as shown in FIG. 58 includes only the driving circuit 702 as shown in FIG. 59. This driving circuit 702 is the same as the driving circuit 602 in the eighteenth embodiment except that the pulse generating circuit 604 does not generate the pulses for operating the sample holding circuit and color separating circuit. By the way, the horizontal synchronizing signal HSYNC and vertical synchronizing signal VSYNC from the pulse generating circuit 604 are compounded by the mixer 606 and are output as a synchronizing signal SYNC from the signal line S. The video signal $V_{OUT}$ output from the imaging means 513 is output as it is to the electric line V.

As shown in FIG. 58, the four signal lines S, V, G and P from the above mentioned signal circuit part 701 are connected to the signal processing apparatus 710 provided separately from the drum 3 through the slip ring 521 of four poles. By the way, the signal line S' connected to the signal line S through the slip ring 521 and the current source line P' are connected to the respective internal conductors of the cable 526.

The above mentioned signal processing apparatus 710 is formed as shown in FIG. 60.

The synchronizing signal SYNC input from the signal line S' is separated into a vertical synchronizing signal VSYNC and horizontal synchronizing signal HSYNC by the synchronizing separating circuit 711 and the separated signals VSYNC and HSYNC are input into the pulse generating circuit 712. The above mentioned horizontal synchronizing signal HSYNC is input also into the PLL oscillating circuit 713 which outputs a clock signal CLK synchronized with the horizontal synchronizing signal HSYNC. This clock signal CLK is input into the above mentioned pulse generating circuit 712 which can produce all the pulses required to operate the signal processing apparatus 710 by the respective signals of VSYNC, HSINC and CLK.

The other elements of this signal processing apparatus 710 are the same as of the signal processing circuit 601 in the first embodiment. That is to say, the video signal input from the signal line V' has the pulse component removed by the sample holding circuit 611, becomes a continued video signal and is adjusted by the AGC circuit 612 so as to be always of a substantially constant output. The output of this AGC circuit 612 is input into the low-pass filter 613 and color separating circuit 615. A luminance signal is extracted in the above mentioned low pass filter 613 and is gamma-corrected in the gamma correcting circuit. On the other hand, only color signals are taken out in the above mentioned color separating circuit 615 and are gamma-corrected in the gamma correcting circuit 616. The luminance signal and color signals γ- corrected in the above mentioned gamma correcting circuits 614 and 616 are input into the composite video signal producing circuit 617 into which the synchronizing signal SYNC' output from the above mentioned pulse generating circuit 712 is also input. By using these signals, a video signal, for example, of an NTSC system is output from the above mentioned composite video signal producing circuit 617. By the way, the above mentioned pulse generating circuit 712 generates pulses for operating the above mentioned sample holding circuit 611 and color separating circuit 615.

Thus, according to this embodiment, as the driving circuit 702 requiring many signal lines with the imaging means 513 is made integral with the drum 503, the same as in the eighteenth embodiment, no slip ring of many poles is required.

The other elements are the same as in the eighteenth embodiment.

The twenty-second embodiment of the present invention is shown in FIGS. 61 to 64.

In this embodiment, the driving circuit and a part of the signal processing circuit are made integral with the drum 503 and the picture image processing apparatus 725 is provided separately from the drum 503 so that a more complicated video signal may be processed.

Figure 61:
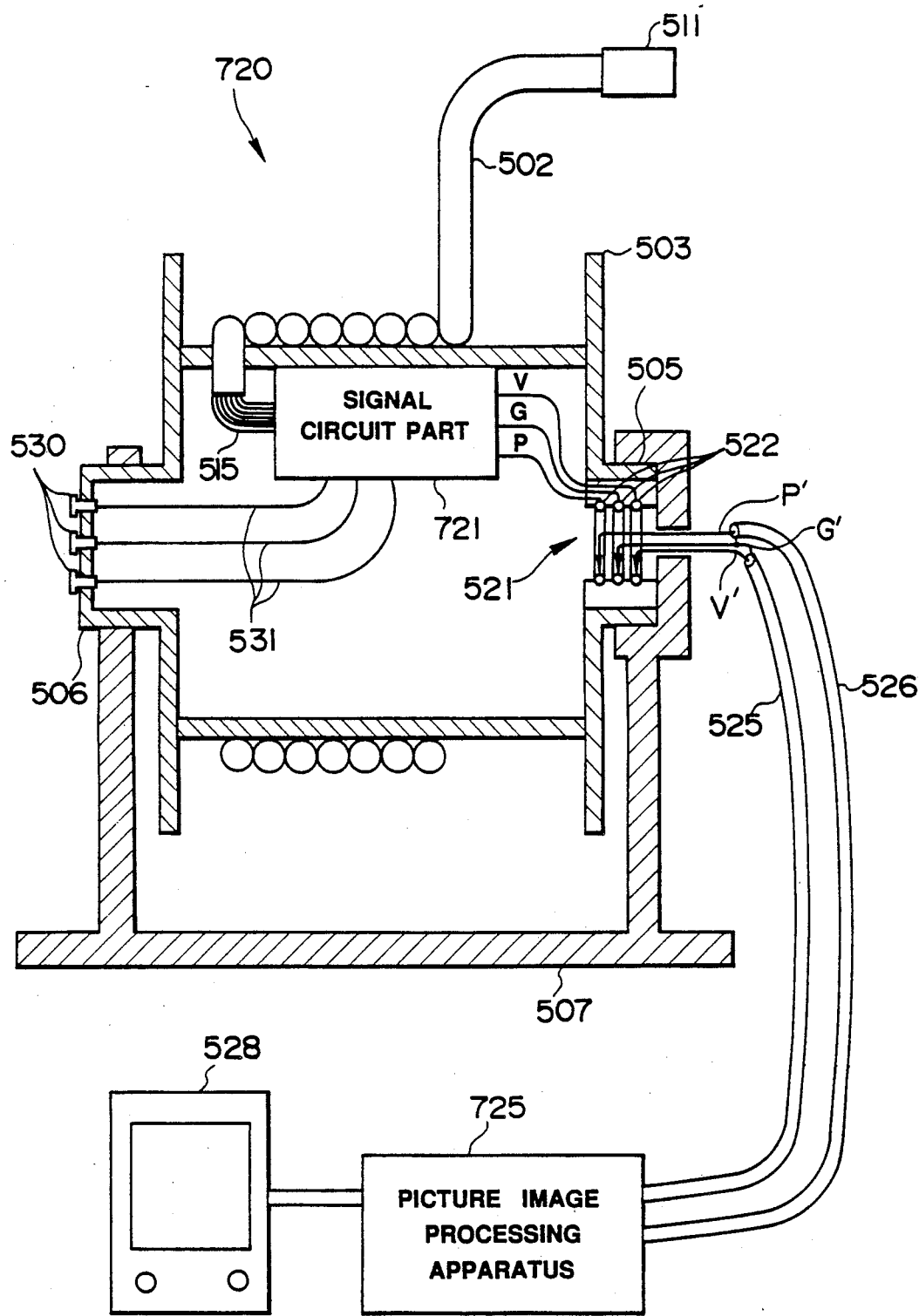
FIGS. 61 to 64 relate to the twenty-second embodiment of the present invention.

In the signal circuit part 520 in the eighteenth embodiment, the NTSC signal which is fed directly to the monitor television 528 to be able to display a video image is output to the electric line V but, in the winding type endoscope apparatus 720 in this embodiment, as shown in FIG. 61, the signal circuit part 721 fixed to the drum 503 outputs to V an optimum signal to be input into the above mentioned picture image processing apparatus 725.

Figure 62:
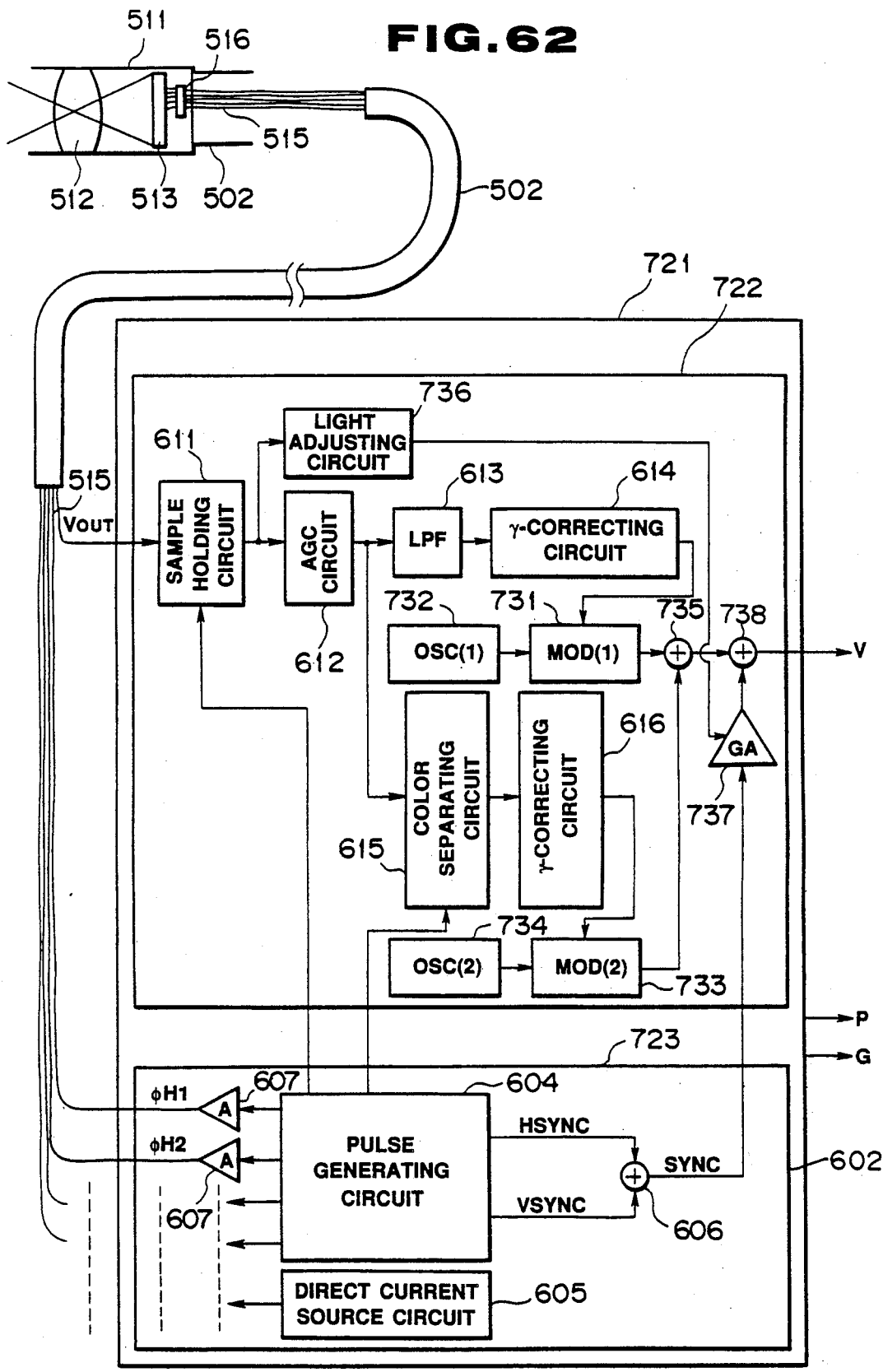

As shown in FIG. 62, the above mentioned signal circuit part 721 includes a signal processing circuit 722 and driving circuit 723.

The above mentioned driving circuit 723 is the same as the driving circuit 602 in the eighteenth embodiment. That is to say, the driving circuit 723 is provided with a pulse generating circuit 604 generating driving pulses required to operate the imaging means 513 and a direct current source circuit 605 generating a direct current voltage required to operate the same imaging means 513. The driving pulses $\phi H_1$, $\phi H_2$, etc. from the above mentioned pulse generating circuit 604 are output through the amplifiers 607. The above mentioned pulse generating circuit 604 generates pulses for operating the sample holding circuit 611 and color separating circuit 615 within the signal processing circuit 722. The above mentioned pulse generating circuit 604 generates a horizontal synchronizing signal HSYNC and vertical synchronizing signal VSYNC which are compounded by the mixer 606 to be output as a synchronizing signal SYNC.

On the other hand, the above mentioned signal processing circuit 722 is provided with the above mentioned sample holding circuit 611 which inputs the video signal V°''' output from the imaging means 13 and has the pulse component removed to make a continued video signal. The output of this sample holding circuit 611 is input into the AGC circuit 612 which varies the amplitude in response to the brightness of the object so that the output may be always substantially constant. The output of this AGC circuit 612 is input into the low-pass filter (LPF) 613 and color separating circuit 615. The above mentioned low-pass filter 613 removes the high band component which is the color signal component in the input signal to leave only the luminance signal. The luminance signal output from this low-Pass filter 613 is input into the gamma correcting circuit 614 and is gamma-corrected. The output of the above mentioned gamma correcting circuit 614 is input into a first modulating circuit (which shall be mentioned as MOD(1) hereinafter) 731 which modulates a carrier which is the output of the first oscillating circuit (which shall be mentioned as OSC(1) hereinafter) 732 by a luminance signal.

On the other hand, the above mentioned color separating circuit 615 takes out only the color signal which is a high band component in the input signal. The color signal output from this color separating circuit 615 is input into the gamma correcting circuit 616 to be gamma-corrected. The output of the above mentioned gamma correcting circuit 616 is input into a second modulating circuit (which shall be mentioned as MOD(2) hereinafter) 733. This MOD(2) 733 modulates by a color signal a carrier which is the output of a second oscillating circuit (which shall be mentioned as OSC(2) hereinafter) 734.

The output of the above mentioned MOD(1) 731 and the output of MOD(2) are compounded by the mixer 735. However, as the oscillating frequency of OSC(1) 732 and the oscillating frequency of OSC(2) 734 are different from each other, the luminance signal and color signals which are modulated signals will not be mixed and will be separately demodulated in the picture image processing apparatus 725.

The output of the above mentioned sample holding circuit 611 is input into the light adjusting circuit 736 which generates a light adjusting signal to be fed to a light source apparatus (such as is shown, for example, in the first embodiment) not illustrated for obtaining an illuminating light for illuminating the object. The above mentioned light adjusting signal controls the output light amount of the light source apparatus to make the brightness of the object optimum. The light adjusting signal output from the above mentioned light adjusting circuit 736 is input into the control terminal of a variable gain amplifier (mentioned as GA hereinafter) 737. The synchronizing signal SYNC output from the driving circuit 723 is input into the signal input terminal of this GA 737. Therefore, a synchronizing signal of an amplitude varied by the size of the light adjusting signal will appear at the output terminal of the GA 737.

Figure 63A:
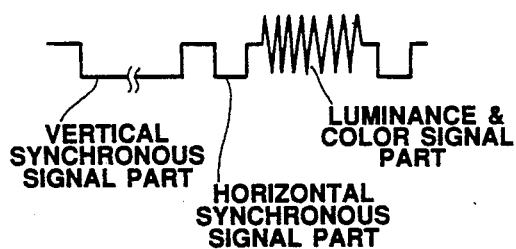
FIGS. 63(a) and (b) are waveform diagrams respectively showing composite signals.

This synchronizing signal is further compounded to a composite signal of the outputs of the MOD(1) 731 and MOD(2) 733 by the mixer 738 and is output as a composite signal to the electric line V. As shown in FIG. 63(a), this composite signal consists of a vertical synchronizing signal part, horizontal synchronizing signal part and luminance and color signal part.

As shown in FIG. 61, the same as in the eighteenth embodiment, the above mentioned electric line V is connected to the electric line V' through the slip ring 521 and this electric line V' is connected to the picture image processing apparatus 725.

Figure 64:
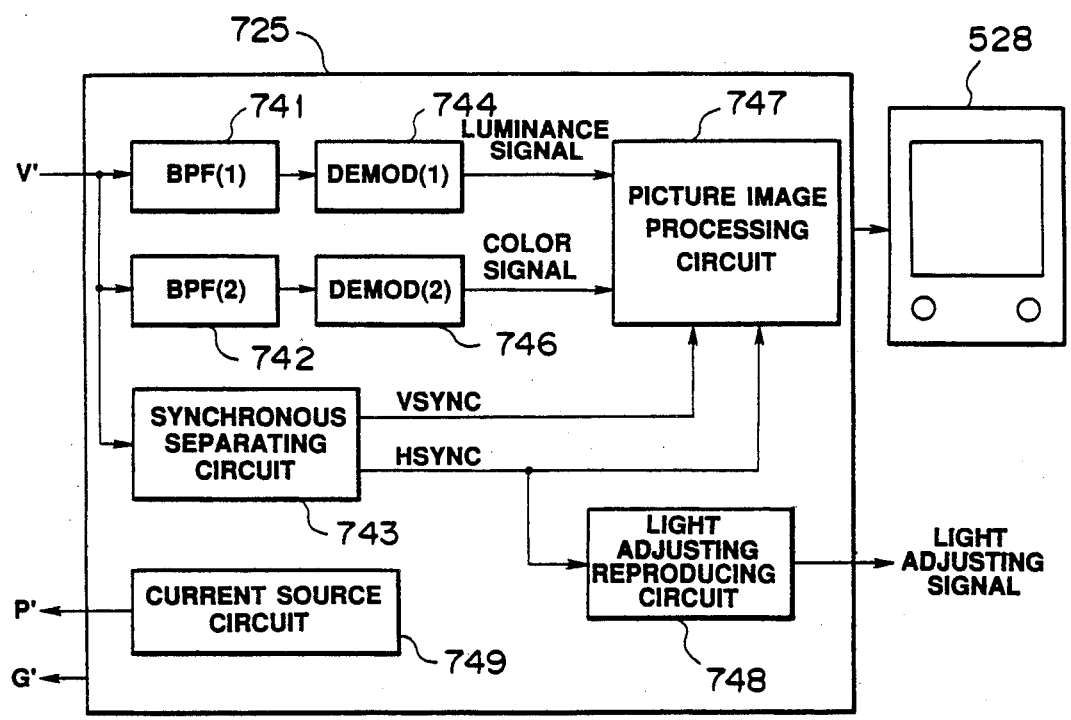

The above mentioned picture image Processing apparatus 725 is formed as shown in FIG. 64.

The composite signal input from the above mentioned electric line V' is input into a band pass filter (mentioned as BPF hereinafter)(1) 741, BPF(2) 742 and synchronizing separating circuit 743. The above mentioned BPF(1) 741 takes only the carrier modulated by the luminance component out of the composite signal and the output of this BPF(1) 741 is input into a first demodulating circuit (mentioned as DEMOD(1) hereinafter) 744 to demodulate the luminance signal. In the same manner, the color signals are demodulated by the BPF(2) 742 and second demodulating circuit (mentioned as DEMOD(2) hereinafter) 746. Also, the vertical synchronizing signal VSYNC and horizontal synchronizing signal HSYNC are separated and output by the synchronizing separating circuit 743.

The demodulated luminance signal and color signals are input into a picture image processing circuit 747, are variously processed as picture images and are then delivered as NTSC signals to the television monitor 528 to display the object image. For the picture image processing, the vertical synchronizing signal VSYNC and horizontal synchronizing signal HSYNC are necessary and are input also into the picture image processing circuit 747.

By the way, there are considered such many examples of the picture image processing in the above mentioned picture image processing circuit 747 as the still, enlargement, contraction, rotation and color enhancement of picture images.

Figure 63B:
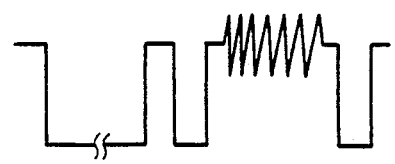

As described above, the vertical and horizontal synchronizing signals are varied in amplitude by the light adjusting signal. That is to say, the composite signal input into the picture image processing circuit 747 will be small in the amplitude of the vertical and horizontal synchronizing signals as shown in FIG. 63(a) in case the level of the light adjusting signal is small but will be large in the amplitude of the vertical and horizontal synchronizing signals as shown in FIG. 63(b) in case the level of the light adjusting signal is large. In this embodiment, a light adjusting signal reproducing circuit 748 is provided within the above mentioned picture image processing apparatus 725 and reproduces a light adjusting signal from its amplitude by using the horizontal synchronizing signal HSYNC. This light adjusting signal is delivered to a light source apparatus not illustrated to control the light amount and to make the brightness of the object optimum.

Thus, according to this embodiment, while using a slip ring of three poles the same as in the eighteenth embodiment, the picture image processing apparatus 725 for processing a complicated picture image can be combined.

The other elements are the same as in the eighteenth embodiment.

As explained above, according to the sixteenth to twenty-second embodiments, there are effects that a large expensive detrimental slip ring of many poles need not be used, the insertable part tip can be made small and a favorable video image high in the resolution is obtained.

Figure 65:
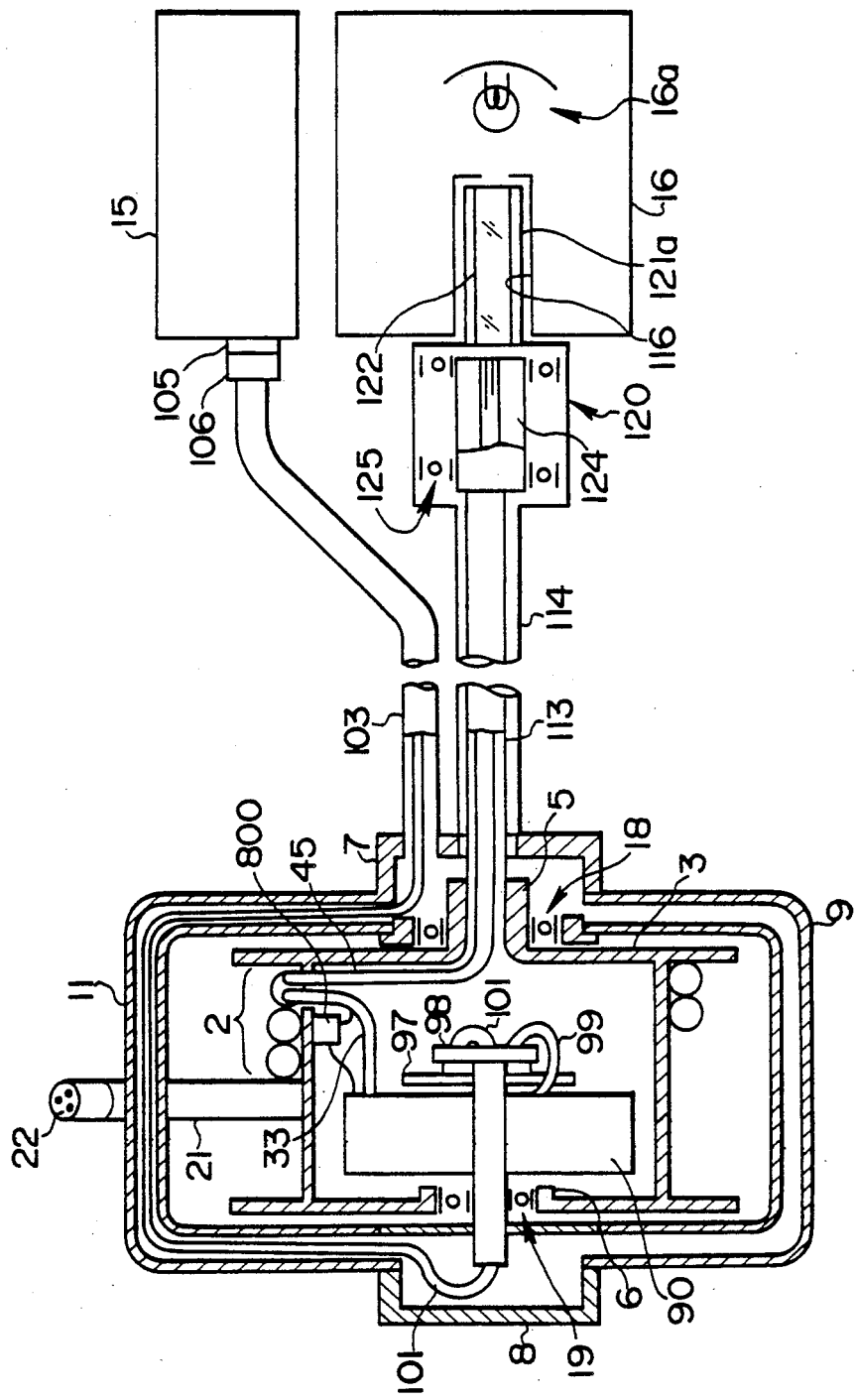
FIG. 65 is an explanatory view showing the structure of an endoscope apparatus of the twenty-third embodiment of the present invention.
Figure 66:
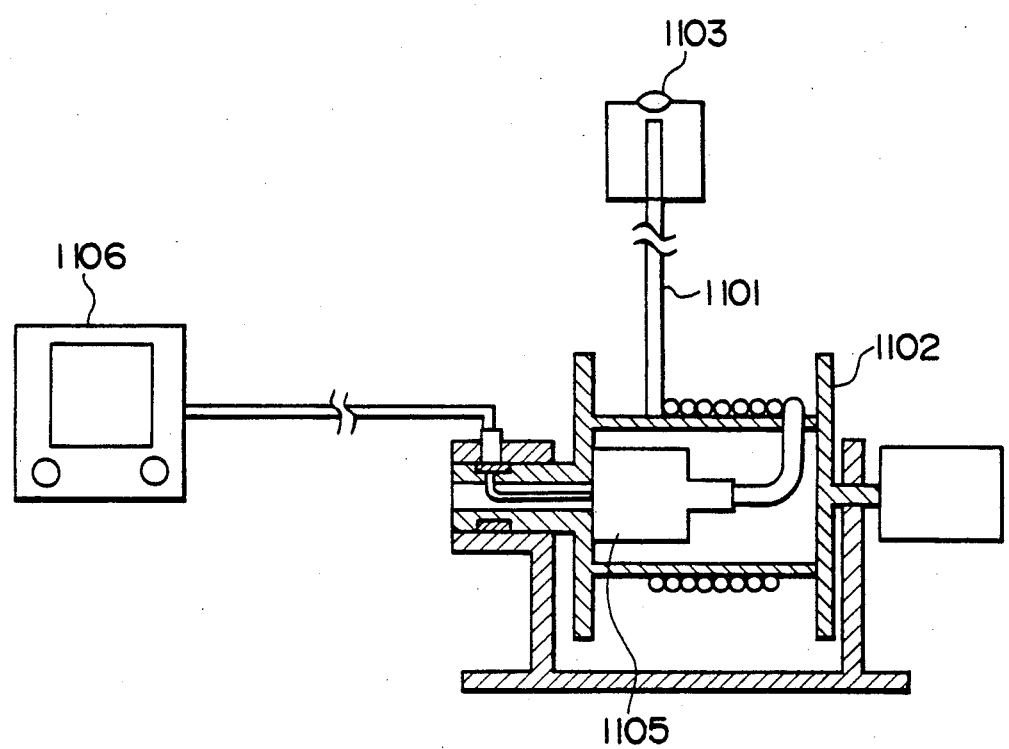
FIGS. 66 to 71 relate to related arts.
Figure 67:
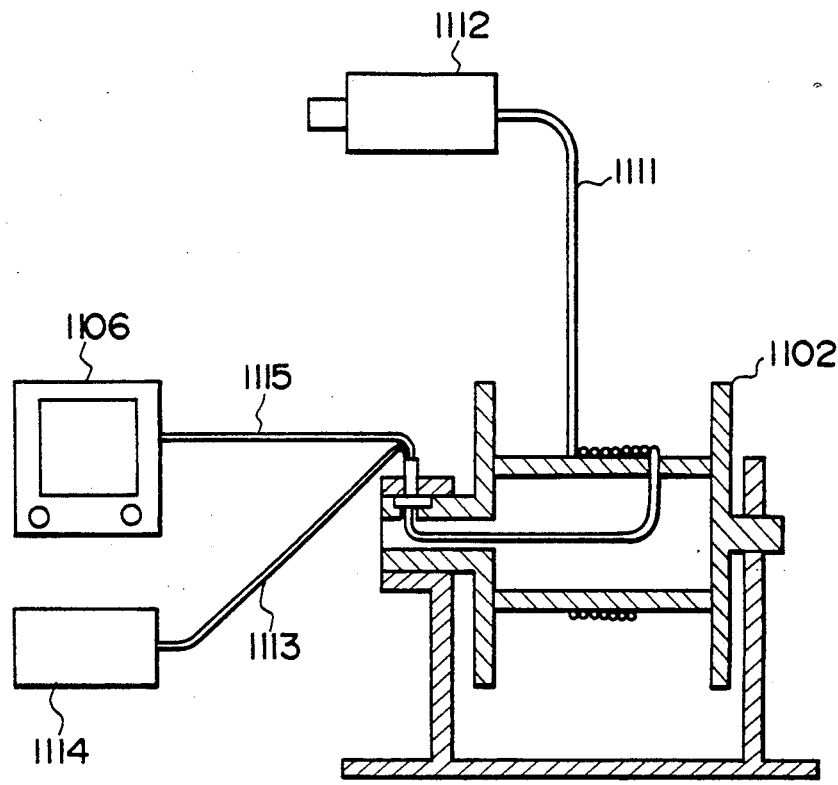

The twenty-third embodiment of the present invention is shown in FIG. 65.

In this embodiment, only a part of the signal processing circuit is made integral with the drum and the construction is substantially the same as in the third embodiment.

In this embodiment, a pre-amplifier 800 is fitted to the rotary part of the drum 3 and only the video signal output line $V_{OUT}$ from the solid state imaging device 30 of the signal line 33 is connected to the clip ring 90 through the above mentioned pre-amplifier 800. The other elements are the same as in the third embodiment.

According to this embodiment, as the $V_{OUT}$ signal is amplified by the pre-amplifier 800, the sensitivity of the endoscope apparatus can be increased without amplifying the noise mixed in by the slip ring 90. Thus, by the increase of the sensitivity, the light amount for the illumination of the object can be reduced and the light source apparatus 16 can be made small.

The other elements are the same as in the third embodiment.

By the way, the present invention can be applied to not only industrial but also medical endoscope apparatus.

In this invention, it is apparent that working modes different in a wide range can be formed on the basis of this invention without departing from the spirit and scope of the invention. This invention is not restricted by its specific working modes except as limited by the appended claims.

What is claimed is:

1. A winding type endoscope apparatus comprising:
   an elongate flexible insertable part having an illuminating window and observing window in a tip part thereof;
   a winding unit having a winding member fitted with said insertable part in a base end part and capable of winding up and housing said insertable part, and a supporting part rotatably supporting said winding member;
   an illuminating means for emitting an illuminating light out of said illuminating window;
   an observing means for receiving the light from an object incident from said observing window to make the object observable;
   an external apparatus provided separately from said winding member and forming at least one of said illuminating means and observing means; and
   a flexible lead-out means, forming at least one of said illuminating means and observing means, extending axially out of a side of said winding member and connected to said external apparatus,
   said winding member and said external apparatus being separated from each other and being connected by said lead-out means, and said lead-out means operatively connecting separate parts of at least one of said illuminating means and said observing means within said winding member and said external apparatus.

2. An endoscope apparatus according to claim 1 wherein said illuminating means has an illuminating light transmitting means inserted through said insertable part leading the illuminating light to said illuminating window; said observing means has an imaging means for receiving and imaging the light from the object incident from said observing window, a signal processing means for processing a signal for said imaging means and a displaying means for receiving a video signal output from said signal processing means and displaying the object image; said external apparatus includes a light source apparatus for feeding an illuminating light to said illuminating light transmitting means and a signal processing apparatus forming said signal processing means; and said lead-out means includes said illuminating light transmitting means connected to said light source apparatus and a signal connecting means connecting said imaging means and said signal processing apparatus with each other.

3. An endoscope apparatus according to claim 1 wherein said illuminating means has an illuminating light transmitting means inserted through said insertable part and leading the illuminating light to said illuminating window; said observing means has an imaging means for receiving and imaging the light from an object incident from said observing window; a signal processing means for processing the signal for said imaging means and a displaying means for receiving the video signal output from said signal processing means and displaying the object image; said external apparatus is a light source apparatus feeding an illuminating light to said illuminating light transmitting means; and said lead-out means includes said illuminating light transmitting means connected to said light source apparatus.

4. An endoscope apparatus according to claim 1 wherein said observing means has an imaging means for receiving and imaging the light from an object incident from said observing window, a signal processing means for processing a signal of said imaging means and a displaying means for receiving a video signal output from said signal processing means and displaying the object image; said external apparatus is a signal processing apparatus forming said signal processing means; and said lead-out means includes a signal connecting means connecting said imaging means and said signal processing apparatus with each other.

5. An endoscope apparatus according to claim 1 wherein said illuminating means has an illuminating light transmitting means inserted through said insertable part for leading the illuminating light to said illuminating window; said observing means has an imaging means for receiving and imaging the light from an object incident from said observing window, a signal processing means for processing a signal for said imaging means and a displaying means for receiving a video signal output from said signal processing means and disPlaying the object image; said external apparatus is an apparatus including a light source apparatus for feeding an illuminating light to said illuminating light transmitting means and a video signal processing apparatus forming said signal processing means combined together: and said lead-out means includes an illuminating light connecting means connecting said illuminating light transmitting means to said light source apparatus and a signal connecting means connecting said imaging means and said signal processing apparatus with each other.

6. An endoscope apparatus according to claim 1 wherein said illuminating means has an illuminating light transmitting means inserted through said insertable part for leading the illuminating light to said illuminating window; said external apparatus is a light source apparatus for feeding an illuminating light to said illumination light transmitting means; and said lead-out means includes said illuminating light transmitting means.

7. An endoscope apparatus according to claim 2, 3 or 6 further comprising a connecting means rotatably connecting said illuminating light transmitting means to said light source apparatus.

8. An endoscope apparatus according to claim 2, 3 or 6 further comprising a hollow first covering member housing the part of said illuminating light transmitting means extended out of the side of said winding member.

9. An endoscope apparatus according to claim 8 wherein said first covering member is fixed to said winding member and said connecting means is provided with a rotary part connected to said illuminating light transmitting means and to said first covering member and a holding part rotatably holding said rotary part and connected to said light source apparatus.

10. An endoscope apparatus according to claim 9 further comprising a second covering member covering said first covering member.

11. An endoscope apparatus according to claim 10 wherein said second covering member is fixed at the winding member end to the supporting part supporting said winding member and is fixed at the opposite end to the holding part of said connecting means.

12. An endoscope apparatus according to claim 11 wherein a means for reducing friction between said first covering member and said second covering member is further provided between said first covering member and second covering member.

13. An endoscope apparatus according to claim 8 wherein one end of said first covering member is fixed to said winding member and said connecting means is provided with a rotary part connected to said illuminating light transmitting means and to the opposite end of said first covering member and a holding part for holding said rotary part is provided rotatably with the axial direction as a center of rotation in said light source apparatus.

14. An endoscope apparatus according to claim 8 wherein said illuminating light transmitting means is formed of an optical fiber bundle 15. An endoscope apparatus according to claim 14 wherein said optical fiber bundle is not covered with a fiber protecting tube at least in an area in which said first covering member has flexibility.

16. An endoscope apparatus according to claim 2, 4 or 5 wherein said signal connecting means is provided with a first signal line connected to said imaging means and a second signal line extended in the axial direction out of the side of said winding member and connected to said signal processing apparatus, and rotary electric contacts are provided within said winding member to electrically connect said first signal line and second signal line with each other.

17. An endoscope apparatus according to claim 2 wherein said illuminating light transmitting means and said signal connecting means are both led out of one side of said winding member.

18. An endoscope apparatus according to claim 17 wherein said winding unit has a pipe extending between both sides of winding member, said illuminating light transmitting means is led out to said light source apparatus from one side of said winding member and said signal connecting means is inserted through said pipe from the other side of said winding member, is led to said one side of said winding member and is led to said signal processing apparatus out of said one side.

19. An endoscope apparatus according to claim 18 wherein said pipe is a handle for carrying said winding member.

20. An endoscope apparatus according to claim 18 wherein said pipe is a supporting pipe for supporting said winding member.

21. An endoscope apparatus according to claim 2, 3, 4 or 5 wherein a signal correcting circuit for at least one of said imaging means and said signal processing means is provided within said winding member.

22. An endoscope apparatus according to claim 2, 3, 4 or 5 wherein said imaging means has an image forming optical system for forming an image provided in said observing window and a solid state imaging device arranged in the image forming position of said image forming optical system.

23. An endoscope apparatus according to claim 3 wherein said signal processing means is provided within said winding member.

24. An endoscope apparatus according to claim 23 wherein a signal cable extended out of the side of said winding member and connecting said signal processing means and said displaying means with each other is provided.

25. An endoscope apparatus according to claim 2, 3 or 4 wherein said imaging means has an image forming optical system for forming an image provided opposite said observing window, an image transmitting means inserted through said insertable part for transmitting the image formed by said image forming optical system to said winding member and an imaging apparatus for imaging the image transmitted by this image transmitting means.

26. An endoscope apparatus according to claim 3 or 23 wherein a signal transmitting means for transmitting a picture image information signal from said imaging means and a signal receiving means for receiving said picture image information signal transmitted from said signal transmitting means and transmitting it to said displaying means are provided between said imaging means and said displaying means.

27. An endoscope apparatus according to claim 3 or 23 wherein a photocoupler for transmitting and receiving a signal between said imaging means and said displaying means by using a light is provided within said winding member.

28. An endoscope apparatus according to claim 5 further comprising a connecting means for connecting rotatably, with the axial direction of the winding member as a center of rotation, said illuminating light transmitting means and said signal connecting means to said light source apparatus and signal processing apparatus respectively.

29. An endoscope apparatus according to claim 28 further comprising a hollow first covering member housing parts of said illuminating light transmitting means and signal connecting means which are extended out of the side of said winding member.

30. An endoscope apparatus according to claim 29 wherein one end of said first covering member is fixed to said winding member and a single connecting means is provided with a rotary part connected to said illuminating light transmitting means, said signal connecting means and the other end of said first covering member including a holding part rotatably holding said rotary part and connected to said light source apparatus and signal processing apparatus which are combined together.

31. An endoscope apparatus according to claim 30 wherein said rotary part and said holding part are provided with rotary electric contacts electrically connecting said video signal processing apparatus and said connecting means with each other.

32. An endoscope apparatus according to claim 31 further comprising a second covering member covering said first covering member.

33. An endoscope apparatus according to claim 32 wherein said second covering member is fixed to the supporting part supporting said winding member and to the holding part of said connecting means.

34. An endoscope apparatus according to claim 6 wherein said observing means is provided with an image forming optical system at said observing window for forming an image, an image transmitting means inserted through said insertable part for transmitting the image formed by said image forming optical system to said winding member and an eyepiece means for making the image transmitted by said image transmitting means observable from outside the winding member.

35. An endoscope apparatus according to claim 34 further comprising a television camera removably connected to said eyepiece.

36. An endoscope apparatus according to claim 34 further comprising a still camera removably connected to said eyepiece.

37. An endoscope apparatus according to claim 34 further comprising a viewing apparatus removably connected to said eyepiece.

38. An endoscope apparatus according to claim 2, 3 or 6 wherein said illuminating light transmitting means has a first light guide in which an exit end is arranged opposite said illuminating window and an entrance end is fixed to the rotation center of the side of said winding member and a second light guide in which an exit end is fixed to the supporting part supporting said winding member so that an exit end surface is opposite an entrance end surface of said first light guide and an entrance end is connected to said light source apparatus.

39. An endoscope apparatus according to claim 2, 3, 4 or 5 wherein said illuminating means emits a white light, said imaging means is a color imaging means for synchronously imaging an object image and said signal processing means synchronously processes a signal corresponding to the image.

40. An endoscope apparatus according to claim 2, 3, 4 or 5 wherein said illuminating means emits a field sequential light, said imaging means is a color imaging means for field sequentially imaging an object image and said signal processing means field sequentially processes a signal corresponding to the image.

41. An endoscope apparatus according to claim 1 further comprising expansion limiting members for preventing said insertable part wound up on said winding member from expanding in the outer peripheral direction.

42. An endoscope apparatus according to claim 41 wherein said members are rollers fitted to frames rotatably supporting said winding member and to a handle for carrying the winding member so as to be opposed to the periphery of said winding member.

43. An endoscope apparatus according to claim 42 further comprising a means for pressing said rollers to said winding member.

44. An endoscope apparatus according to claim 42 wherein at least three of said rollers are provided about the periphery of said winding member.

45. An endoscope apparatus according to claim 1 wherein housing hooks for winding up and housing said lead-out means are further provided on the side of said winding member.

46. An endoscope apparatus according to claim 1 or 45 further comprising a guard for protecting said lead-out means.

47. An endoscope apparatus according to claim 1 further comprising a protecting member in which the tip part of said insertable part is inserted to be protected.

48. A winding type endoscope apparatus comprising:
a winding drum having a rotary axis;
a supporting member for rotatably supporting said winding drum;
an elongate flexible tube connected to said winding drum for winding up said elongate flexible tube, said elongate flexible tube having therein an observing means and an optical fiber bundle for transmitting illuminating light;
a light source apparatus;
said optical fiber bundle having an extending part extending in a side direction from the rotary axis of said drum; and
a connecting means rotatably connected to said extending part for connecting said extending part to said light source apparatus.

49. An endoscope apparatus according to claim 48, further comprising a tube member housing said optical fiber bundle, and end of the tube member being connected to said connecting means and the other end being connected to said supporting member, and said connecting means being connected to said light source apparatus.

50. An endoscope apparatus according to claim 49, further comprising a covering member provided in said tube member for covering said extending part, an end of said covering member being connected to said rotary axis of said drum and the other end of said covering member being rotatably connected to said tube member at an end of said tube member adjacent said light source apparatus.

51. An endoscope apparatus according to claim 50, further comprising a protecting member for covering said extending part in said covering member except for the center part of said extending part.

52. An endoscope apparatus according to claim 51, further comprising a tube provided between said tube member and said covering member for reducing friction between said tube member and said covering member.

53. An endoscope apparatus according to claim 48, wherein said observing means has a cable for transmitting an observing image, a proximal side of said cable is led out from said rotary axis of said winding drum to an outside of said winding drum through said supporting member and is led out to the outside of said supporting member.

54. An endoscope apparatus according to claim 53, wherein said supporting member has a guide path for guiding said cable and the proximal side of said cable is led out from the side of said connecting means of said supporting member to the outside through said guide path.

* * * * *